US012642664B2

(12) United States Patent
Yager

(10) Patent No.: US 12,642,664 B2
(45) **Date of Patent: *Jun. 2, 2026**

(54) IMPLANTS FOR ADDING JOINT INCLINATION TO A KNEE ARTHROPLASTY

(71) Applicant: Zimmer, Inc., Warsaw, IN (US)

(72) Inventor: Edward R. Yager, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 892 days.

This patent is subject to a terminal disclaimer.

(21) Appl. No.: 17/866,151

(22) Filed: Jul. 15, 2022

(65) Prior Publication Data

US 2022/0346962 A1     Nov. 3, 2022

Related U.S. Application Data

(63) Continuation of application No. 16/179,201, filed on Nov. 2, 2018, now Pat. No. 11,426,282.

(Continued)

(51) Int. Cl.
| | |
|---|---|
| *A61F 2/38* | (2006.01) |
| *A61F 2/46* | (2006.01) |
| A61F 2/30 | (2006.01) |

(52) U.S. Cl.
CPC ............ *A61F 2/389* (2013.01); *A61F 2/4684* (2013.01); *A61F 2002/30324* (2013.01);
(Continued)

(58) Field of Classification Search
CPC ........ A61F 2/38; A61F 2/3836; A61F 2/3886; A61F 2/389
See application file for complete search history.

(56) References Cited

U.S. PATENT DOCUMENTS

| | | |
|---|---|---|
| 3,774,244 A | 11/1973 | Walker |
| 4,016,606 A | 4/1977 | Murray et al. |
| | (Continued) | |

FOREIGN PATENT DOCUMENTS

| | | |
|---|---|---|
| AU | 2011343440 B2 | 4/2014 |
| AU | 2011286306 B2 | 10/2014 |
| | (Continued) | |

OTHER PUBLICATIONS

"U.S. Appl. No. 16/179,201, Supplemental Notice of Allowability mailed Aug. 2, 2022", 2 pgs.
(Continued)

*Primary Examiner* — Marcia L Watkins
(74) *Attorney, Agent, or Firm* — Schwegman Lundberg & Woessner, P.A.

(57) ABSTRACT

According to one example, a bearing component for a knee arthroplasty is disclosed. The bearing component can optionally comprise any one or combination of: a medial compartment having an medial articular surface with a medial articular track and having a first thickness as measured at the medial articular track between the medial articular surface a medial distal surface; and a lateral compartment having a lateral articular surface with a lateral articular track and having a second thickness as measured at the lateral articular track between the lateral articular surface a lateral distal surface; wherein the medial articular surface at the medial articular track and the lateral articular surface at the lateral articular track each have an inclination so as to form an acute angle with respect to a resected proximal surface of a tibia.

18 Claims, 8 Drawing Sheets

Related U.S. Application Data

(60) Provisional application No. 62/587,192, filed on Nov. 16, 2017.

(52) U.S. Cl.
CPC ............... *A61F 2002/30326* (2013.01); *A61F 2002/30604* (2013.01); *A61F 2002/30607* (2013.01); *A61F 2002/30616* (2013.01); *A61F 2002/30621* (2013.01); *A61F 2/38* (2013.01); *A61F 2/385* (2013.01); *A61F 2/3886* (2013.01); *A61F 2002/3895* (2013.01)

(56) References Cited

U.S. PATENT DOCUMENTS

| | | |
|---|---|---|
| 4,257,129 A | 3/1981 | Volz |
| 4,301,553 A | 11/1981 | Noiles |
| 4,340,978 A | 7/1982 | Buechel et al. |
| 4,501,266 A | 2/1985 | McDaniel |
| 4,568,348 A | 2/1986 | Johnson et al. |
| 4,673,408 A | 6/1987 | Grobbelaar |
| 4,711,639 A | 12/1987 | Grundei |
| 4,714,474 A | 12/1987 | Brooks, Jr. et al. |
| 4,759,767 A | 7/1988 | Lacey |
| 4,769,040 A | 9/1988 | Wevers |
| 4,770,661 A | 9/1988 | Oh |
| 4,795,468 A | 1/1989 | Hodorek et al. |
| 4,822,365 A | 4/1989 | Walker et al. |
| 4,936,853 A | 6/1990 | Fabian et al. |
| 4,944,756 A | 7/1990 | Kenna |
| 4,944,757 A | 7/1990 | Martinez et al. |
| 4,950,298 A | 8/1990 | Gustilo et al. |
| 4,959,071 A | 9/1990 | Brown et al. |
| 4,963,152 A | 10/1990 | Hofmann et al. |
| 4,999,119 A | 3/1991 | Norman et al. |
| 5,007,933 A | 4/1991 | Sidebotham et al. |
| 5,047,057 A | 9/1991 | Lawes |
| 5,047,058 A | 9/1991 | Roberts et al. |
| 5,059,216 A | 10/1991 | Winters |
| 5,061,271 A | 10/1991 | Van Zile |
| 5,071,438 A | 12/1991 | Jones et al. |
| 5,108,442 A | 4/1992 | Smith |
| 5,116,375 A | 5/1992 | Hofmann |
| 5,133,758 A | 7/1992 | Hollister |
| 5,137,536 A | 8/1992 | Koshino |
| 5,147,405 A | 9/1992 | Van Zile |
| 5,171,283 A | 12/1992 | Pappas et al. |
| 5,192,328 A | 3/1993 | Winters |
| 5,194,066 A | 3/1993 | Van Zile |
| 5,197,488 A | 3/1993 | Kovacevic |
| 5,218,021 A | 6/1993 | Clark et al. |
| 5,219,362 A | 6/1993 | Tuke et al. |
| 5,226,915 A | 7/1993 | Bertin |
| 5,236,461 A | 8/1993 | Forte |
| 5,246,459 A | 9/1993 | Elias |
| 5,271,737 A | 12/1993 | Baldwin et al. |
| 5,275,603 A | 1/1994 | Ferrante et al. |
| 5,282,861 A | 2/1994 | Kaplan |
| 5,282,868 A | 2/1994 | Bahler |
| 5,282,870 A | 2/1994 | Moser et al. |
| 5,290,313 A | 3/1994 | Heldreth |
| 5,310,480 A | 5/1994 | Vidueira |
| 5,326,361 A | 7/1994 | Hollister |
| 5,344,460 A | 9/1994 | Turanyi et al. |
| 5,344,461 A | 9/1994 | Phlipot |
| 5,360,016 A | 11/1994 | Kovacevic |
| 5,364,402 A | 11/1994 | Mumme et al. |
| 5,370,699 A | 12/1994 | Hood et al. |
| 5,370,701 A | 12/1994 | Finn |
| 5,387,239 A | 2/1995 | Bianco et al. |
| 5,387,240 A | 2/1995 | Pottenger et al. |
| 5,391,721 A | 2/1995 | Hanen et al. |
| 5,395,401 A | 3/1995 | Bahler |
| 5,405,396 A | 4/1995 | Heldreth et al. |
| 5,413,604 A | 5/1995 | Hodge |
| 5,413,605 A | 5/1995 | Ashby et al. |
| 5,425,775 A | 6/1995 | Kovacevic et al. |
| 5,445,642 A | 8/1995 | McNulty et al. |
| 5,458,637 A | 10/1995 | Hayes |
| 5,470,354 A | 11/1995 | Hershberger et al. |
| 5,489,311 A | 2/1996 | Cipolletti |
| 5,507,820 A | 4/1996 | Pappas |
| 5,549,688 A | 8/1996 | Ries et al. |
| 5,556,433 A | 9/1996 | Gabriel et al. |
| 5,571,194 A | 11/1996 | Gabriel |
| 5,597,384 A | 1/1997 | Walker |
| 5,609,639 A | 3/1997 | Walker |
| 5,609,641 A | 3/1997 | Johnson et al. |
| 5,609,643 A | 3/1997 | Colleran et al. |
| 5,609,645 A | 3/1997 | Vinciuerra |
| 5,613,970 A | 3/1997 | Houston et al. |
| 5,616,273 A | 4/1997 | Clark et al. |
| 5,656,785 A | 8/1997 | Trainor et al. |
| 5,658,341 A | 8/1997 | Delfosse |
| 5,658,342 A | 8/1997 | Draganich et al. |
| 5,658,344 A | 8/1997 | Hurlburt |
| 5,683,470 A | 11/1997 | Johnson et al. |
| 5,702,463 A | 12/1997 | Pothier et al. |
| 5,702,464 A | 12/1997 | Lackey et al. |
| 5,702,466 A | 12/1997 | Pappas et al. |
| 5,733,292 A | 3/1998 | Gustilo et al. |
| 5,755,801 A | 5/1998 | Walker et al. |
| 5,755,802 A | 5/1998 | Gerber |
| 5,776,200 A | 7/1998 | Johnson et al. |
| 5,782,925 A | 7/1998 | Collazo et al. |
| 5,824,100 A | 10/1998 | Kester et al. |
| 5,824,102 A | 10/1998 | Buscayret |
| 5,824,103 A | 10/1998 | Williams et al. |
| 5,871,539 A | 2/1999 | Pappas |
| 5,871,541 A | 2/1999 | Gerber |
| 5,871,543 A | 2/1999 | Hofmann |
| 5,871,545 A | 2/1999 | Goodfellow et al. |
| 5,871,546 A | 2/1999 | Colleran et al. |
| 5,879,394 A | 3/1999 | Ashby et al. |
| 5,906,643 A | 5/1999 | Walker |
| 5,911,723 A | 6/1999 | Ashby et al. |
| 5,928,286 A | 7/1999 | Ashby et al. |
| 5,964,808 A | 10/1999 | Blaha et al. |
| 5,968,099 A | 10/1999 | Badorf et al. |
| 5,976,147 A | 11/1999 | LaSalle et al. |
| 6,004,351 A | 12/1999 | Tomita et al. |
| 6,004,352 A | 12/1999 | Buni |
| 6,010,534 A | 1/2000 | O'neil et al. |
| 6,013,103 A | 1/2000 | Kaufman et al. |
| 6,039,764 A | 3/2000 | Pottenger et al. |
| 6,068,658 A | 5/2000 | Insall et al. |
| 6,074,425 A | 6/2000 | Pappas |
| 6,080,195 A | 6/2000 | Colleran et al. |
| 6,090,144 A | 7/2000 | Letot et al. |
| 6,102,954 A | 8/2000 | Albrektsson et al. |
| 6,102,955 A | 8/2000 | Mendes et al. |
| 6,123,728 A | 9/2000 | Brosnahan et al. |
| 6,123,729 A | 9/2000 | Insall et al. |
| 6,126,692 A | 10/2000 | Robie et al. |
| 6,143,034 A | 11/2000 | Burrows |
| 6,197,064 B1 | 3/2001 | Haines et al. |
| 6,203,576 B1 | 3/2001 | Afriat et al. |
| 6,206,927 B1 | 3/2001 | Fell et al. |
| 6,210,443 B1 | 4/2001 | Marceaux et al. |
| 6,217,618 B1 | 4/2001 | Hileman |
| RE37,277 E | 7/2001 | Baldwin et al. |
| 6,258,127 B1 | 7/2001 | Schmotzer |
| 6,306,172 B1 | 10/2001 | O'Neil et al. |
| 6,325,828 B1 | 12/2001 | Dennis et al. |
| 6,379,388 B1 | 4/2002 | Ensign et al. |
| 6,406,497 B2 | 6/2002 | Takei et al. |
| 6,413,279 B1 | 7/2002 | Metzger et al. |
| 6,428,577 B1 | 8/2002 | Evans |
| 6,436,145 B1 | 8/2002 | Miller |
| 6,485,519 B2 | 11/2002 | Meyers et al. |
| 6,491,726 B2 | 12/2002 | Pappas |
| 6,506,215 B1 | 1/2003 | Letot et al. |
| 6,506,216 B1 | 1/2003 | McCue et al. |
| 6,558,426 B1 | 5/2003 | Masini |

(56) References Cited

U.S. PATENT DOCUMENTS

| | | |
|---|---|---|
| 6,607,559 B2 | 8/2003 | Ralph et al. |
| 6,623,526 B1 | 9/2003 | Lloyd |
| 6,632,225 B2 | 10/2003 | Sanford et al. |
| 6,660,039 B1 | 12/2003 | Evans et al. |
| 6,702,821 B2 | 3/2004 | Bonutti |
| 6,709,461 B2 | 3/2004 | O'neil et al. |
| 6,743,258 B1 | 6/2004 | Keller |
| 6,755,864 B1 | 6/2004 | Brack et al. |
| 6,770,078 B2 | 8/2004 | Bonutti |
| 6,869,448 B2 | 3/2005 | Tuke |
| 6,916,340 B2 | 7/2005 | Metzger et al. |
| 6,923,832 B1 | 8/2005 | Sharkey et al. |
| 6,942,670 B2 | 9/2005 | Heldreth et al. |
| 6,953,479 B2 | 10/2005 | Carson et al. |
| 6,974,481 B1 | 12/2005 | Carson |
| 6,986,791 B1 | 1/2006 | Metzger |
| 7,025,788 B2 | 4/2006 | Metzger et al. |
| 7,060,074 B2 | 6/2006 | Rosa et al. |
| 7,081,137 B1 | 7/2006 | Servidio |
| 7,083,652 B2 | 8/2006 | McCue et al. |
| 7,153,326 B1 | 12/2006 | Metzger |
| 7,160,330 B2 | 1/2007 | Axelson, Jr. et al. |
| 7,189,262 B2 | 3/2007 | Hayes, Jr. et al. |
| 7,261,740 B2 | 8/2007 | Tuttle |
| 7,264,635 B2 | 9/2007 | Suguro |
| 7,294,149 B2 | 11/2007 | Hozack et al. |
| 7,309,362 B2 | 12/2007 | Yasuda et al. |
| 7,309,363 B2 | 12/2007 | Dietz |
| 7,326,252 B2 | 2/2008 | Otto et al. |
| 7,351,263 B2 | 4/2008 | Afriat |
| 7,364,581 B2 | 4/2008 | Michalowicz |
| 7,412,897 B2 | 8/2008 | Crottet et al. |
| 7,413,577 B1 | 8/2008 | Servidio |
| 7,442,196 B2 | 10/2008 | Fisher et al. |
| 7,445,639 B2 | 11/2008 | Metzger et al. |
| 7,488,330 B2 | 2/2009 | Stad |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,547,327 B2 | 6/2009 | Collazo |
| 7,575,602 B2 | 8/2009 | Amirouche et al. |
| 7,578,821 B2 | 8/2009 | Fisher et al. |
| 7,585,328 B2 | 9/2009 | Haas |
| 7,587,945 B2 | 9/2009 | Crottet et al. |
| 7,591,854 B2 | 9/2009 | Wasielewski |
| 7,625,407 B2 | 12/2009 | Akizuki |
| 7,628,818 B2 | 12/2009 | Hazebrouck et al. |
| 7,632,283 B2 | 12/2009 | Heldreth |
| 7,632,314 B2 | 12/2009 | Dietz |
| 7,635,390 B1 | 12/2009 | Bonutti |
| 7,678,152 B2 | 3/2010 | Suguro et al. |
| 7,695,519 B2 | 4/2010 | Collazo |
| 7,695,520 B2 | 4/2010 | Metzger et al. |
| 7,731,755 B2 | 6/2010 | Wyss et al. |
| 7,776,085 B2 | 8/2010 | Bernero et al. |
| 7,837,691 B2 | 11/2010 | Cordes et al. |
| 7,850,698 B2 | 12/2010 | Straszheim-Morley et al. |
| 8,012,216 B2 | 9/2011 | Metzger |
| 8,065,927 B2 | 11/2011 | Crottet et al. |
| 8,105,386 B2 | 1/2012 | Perrone, Jr. et al. |
| 8,141,437 B2 | 3/2012 | Amirouche et al. |
| 8,152,853 B2 | 4/2012 | Belcher |
| 8,163,028 B2 | 4/2012 | Metzger et al. |
| 8,187,280 B2 | 5/2012 | May et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,268,006 B2 | 9/2012 | Meyers et al. |
| 8,317,870 B2 | 11/2012 | Wagner et al. |
| 8,328,873 B2 | 12/2012 | Metzger et al. |
| 8,366,782 B2 | 2/2013 | Wright |
| 8,491,589 B2 | 7/2013 | Fisher et al. |
| 8,506,571 B2 | 8/2013 | Chana et al. |
| RE44,476 E | 9/2013 | Meyers et al. |
| 8,568,486 B2 | 10/2013 | Wentorf et al. |
| 8,574,304 B2 | 11/2013 | Wentorf et al. |
| 8,591,594 B2 | 11/2013 | Parisi et al. |
| 8,603,101 B2 | 12/2013 | Claypool et al. |
| 8,613,775 B2 | 12/2013 | Wentorf et al. |
| 8,617,250 B2 | 12/2013 | Metzger |
| 8,628,580 B2 | 1/2014 | Sanford et al. |
| 8,690,954 B2 | 4/2014 | Parisi et al. |
| 8,740,984 B2 | 6/2014 | Hartdegen et al. |
| 8,758,444 B2 | 6/2014 | Wentorf et al. |
| 8,764,838 B2 | 7/2014 | Parisi et al. |
| 8,764,840 B2 | 7/2014 | Sanford et al. |
| 8,795,282 B2 | 8/2014 | Earl et al. |
| 8,808,387 B2 | 8/2014 | Hawkins et al. |
| 8,858,643 B2 | 10/2014 | Parisi et al. |
| 8,932,298 B2 | 1/2015 | Colquhoun et al. |
| 8,932,365 B2 | 1/2015 | Parisi et al. |
| 8,979,847 B2 | 3/2015 | Belcher et al. |
| 8,979,936 B2 | 3/2015 | White et al. |
| 8,998,997 B2 | 4/2015 | Ries et al. |
| 9,011,459 B2 | 4/2015 | Claypool et al. |
| 9,060,866 B2 | 6/2015 | Fankhauser et al. |
| 9,072,607 B2 | 7/2015 | Parisi et al. |
| 9,131,945 B2 | 9/2015 | Aram et al. |
| 9,149,206 B2 | 10/2015 | Claypool et al. |
| 9,173,744 B2 | 11/2015 | Donno et al. |
| 9,186,255 B2 | 11/2015 | Parisi |
| 9,192,480 B2 | 11/2015 | Wentorf et al. |
| 9,204,970 B2 | 12/2015 | Parisi et al. |
| 9,283,082 B2 | 3/2016 | Sanford et al. |
| 9,295,557 B2 | 3/2016 | Wentorf et al. |
| 9,295,558 B2 | 3/2016 | Parisi et al. |
| 9,308,095 B2 | 4/2016 | Parisi et al. |
| 9,308,096 B2 | 4/2016 | Wentorf et al. |
| 9,314,343 B2 | 4/2016 | Parisi et al. |
| 9,381,090 B2 | 7/2016 | Wentorf et al. |
| 9,427,337 B2 | 8/2016 | Claypool et al. |
| 9,492,290 B2 | 11/2016 | Claypool et al. |
| 9,539,116 B2 | 1/2017 | Claypool |
| 9,592,133 B2 | 3/2017 | Toler et al. |
| 9,597,090 B2 | 3/2017 | Claypool et al. |
| 9,655,728 B2 | 5/2017 | Parisi et al. |
| 9,655,729 B2 | 5/2017 | Parisi et al. |
| 9,707,089 B2 | 7/2017 | Grey et al. |
| 9,763,794 B2 | 9/2017 | Sanford et al. |
| 9,763,795 B2 | 9/2017 | Parisi et al. |
| 9,763,796 B2 | 9/2017 | Wentorf et al. |
| 9,763,807 B2 | 9/2017 | Claypool et al. |
| 9,788,954 B2 | 10/2017 | Parisi et al. |
| 9,861,490 B2 | 1/2018 | Wentorf et al. |
| 9,901,331 B2 | 2/2018 | Toler et al. |
| 9,918,844 B2 | 3/2018 | Sanford et al. |
| 9,925,050 B2 | 3/2018 | Parisi et al. |
| 9,925,052 B2 | 3/2018 | Dai et al. |
| 10,010,330 B2 | 7/2018 | Claypool et al. |
| 10,092,407 B2 | 10/2018 | Faccioli et al. |
| 10,188,530 B2 | 1/2019 | Claypool et al. |
| 10,195,041 B2 | 2/2019 | Wentorf et al. |
| 10,195,056 B2 | 2/2019 | Wogoman et al. |
| 10,265,181 B2 | 4/2019 | Wentorf et al. |
| 10,278,827 B2 | 5/2019 | Drury et al. |
| 10,413,415 B2 | 9/2019 | Parisi et al. |
| 10,470,889 B2 | 11/2019 | Wentorf et al. |
| 10,500,054 B2 | 12/2019 | Croll |
| 10,517,735 B2 | 12/2019 | Lloyd et al. |
| 10,537,445 B2 | 1/2020 | Wogoman et al. |
| 10,543,099 B2 | 1/2020 | Sanford et al. |
| 10,575,956 B2 | 3/2020 | Dai et al. |
| 10,675,153 B2 | 6/2020 | Byrd et al. |
| 10,835,380 B2 | 11/2020 | Drury et al. |
| 10,898,337 B2 | 1/2021 | Parisi et al. |
| 11,051,948 B2 | 7/2021 | Arnold et al. |
| 11,160,659 B2 | 11/2021 | Drury et al. |
| 11,207,198 B2 | 12/2021 | Oh et al. |
| 11,224,519 B2 | 1/2022 | Wentorf et al. |
| 11,324,598 B2 | 5/2022 | Dai et al. |
| 11,324,599 B2 | 5/2022 | Croll |
| 11,426,282 B2 | 8/2022 | Yager |
| 11,471,288 B2 | 10/2022 | Parisi et al. |
| 11,547,571 B2 | 1/2023 | Byrd et al. |

(56)          References Cited

U.S. PATENT DOCUMENTS

| | | | |
|---|---|---|---|
| 11,911,279 | B2 | 2/2024 | Drury et al. |
| 12,239,540 | B2 | 3/2025 | Wentorf et al. |
| 12,383,407 | B2 | 8/2025 | Parisi et al. |
| 12,458,502 | B2 | 11/2025 | Byrd et al. |
| 2001/0001478 | A1 | 5/2001 | Dams et al. |
| 2001/0047210 | A1 | 11/2001 | Wolf |
| 2002/0058997 | A1 | 5/2002 | O'connor et al. |
| 2002/0072802 | A1 | 6/2002 | O'Neil et al. |
| 2002/0103541 | A1 | 8/2002 | Meyers et al. |
| 2002/0120340 | A1 | 8/2002 | Metzger et al. |
| 2002/0161448 | A1 | 10/2002 | Hayes, Jr. et al. |
| 2003/0055509 | A1 | 3/2003 | Mccue et al. |
| 2003/0199985 | A1 | 10/2003 | Masini |
| 2004/0019382 | A1 | 1/2004 | Amirouche et al. |
| 2004/0019383 | A1 | 1/2004 | Beguec |
| 2004/0034432 | A1 | 2/2004 | Hughes et al. |
| 2004/0059340 | A1 | 3/2004 | Serra et al. |
| 2004/0064191 | A1 | 4/2004 | Wasielewski |
| 2004/0122441 | A1 | 6/2004 | Muratsu |
| 2004/0153066 | A1 | 8/2004 | Coon et al. |
| 2004/0162620 | A1 | 8/2004 | Wyss |
| 2004/0167537 | A1 | 8/2004 | Errico et al. |
| 2004/0186582 | A1 | 9/2004 | Yasuda et al. |
| 2004/0204765 | A1 | 10/2004 | Fenning et al. |
| 2004/0225368 | A1 | 11/2004 | Plumet et al. |
| 2004/0236429 | A1 | 11/2004 | Ensign et al. |
| 2004/0243244 | A1 | 12/2004 | Otto et al. |
| 2004/0267371 | A1 | 12/2004 | Hayes, Jr. et al. |
| 2005/0055102 | A1 | 3/2005 | Tornier et al. |
| 2005/0075736 | A1 | 4/2005 | Collazo |
| 2005/0096747 | A1 | 5/2005 | Tuttle et al. |
| 2005/0143831 | A1 | 6/2005 | Justin et al. |
| 2005/0143832 | A1 | 6/2005 | Carson |
| 2005/0177170 | A1 | 8/2005 | Fisher et al. |
| 2005/0197710 | A1 | 9/2005 | Naegerl |
| 2005/0209701 | A1 | 9/2005 | Suguro et al. |
| 2005/0209702 | A1 | 9/2005 | Todd et al. |
| 2005/0246030 | A1 | 11/2005 | Yao |
| 2005/0267485 | A1 | 12/2005 | Cordes et al. |
| 2005/0267584 | A1 | 12/2005 | Burdulis, Jr. et al. |
| 2005/0278035 | A1 | 12/2005 | Wyss et al. |
| 2006/0004460 | A1 | 1/2006 | Engh et al. |
| 2006/0020343 | A1 | 1/2006 | Ek |
| 2006/0025866 | A1 | 2/2006 | Serafin, Jr. et al. |
| 2006/0030945 | A1 | 2/2006 | Wright |
| 2006/0052782 | A1 | 3/2006 | Morgan et al. |
| 2006/0069436 | A1 | 3/2006 | Sutton et al. |
| 2006/0089653 | A1 | 4/2006 | Auger et al. |
| 2006/0111726 | A1 | 5/2006 | Felt et al. |
| 2006/0142869 | A1 | 6/2006 | Gross |
| 2006/0161259 | A1 | 7/2006 | Cheng et al. |
| 2006/0184176 | A1 | 8/2006 | Straszheim-Morley et al. |
| 2006/0189864 | A1 | 8/2006 | Paradis et al. |
| 2006/0190087 | A1 | 8/2006 | O'Connor |
| 2006/0195195 | A1 | 8/2006 | Burstein et al. |
| 2006/0224244 | A1 | 10/2006 | Thomas et al. |
| 2006/0265080 | A1 | 11/2006 | Mcminn |
| 2007/0010890 | A1 | 1/2007 | Collazo |
| 2007/0123992 | A1 | 5/2007 | Sanford |
| 2007/0129808 | A1 | 6/2007 | Justin et al. |
| 2007/0135924 | A1 | 6/2007 | Verhoogen |
| 2007/0135926 | A1 | 6/2007 | Walker |
| 2007/0185581 | A1 | 8/2007 | Akizuki et al. |
| 2007/0198022 | A1 | 8/2007 | Lang et al. |
| 2007/0233269 | A1 | 10/2007 | Steines et al. |
| 2007/0234819 | A1 | 10/2007 | Amirouche et al. |
| 2007/0239165 | A1 | 10/2007 | Amirouche |
| 2008/0021566 | A1 | 1/2008 | Peters et al. |
| 2008/0051908 | A1 | 2/2008 | Angibaud et al. |
| 2008/0058945 | A1 | 3/2008 | Hajaj et al. |
| 2008/0058947 | A1 | 3/2008 | Earl et al. |
| 2008/0058948 | A1 | 3/2008 | Biegun et al. |
| 2008/0091271 | A1 | 4/2008 | Bonitati et al. |
| 2008/0091272 | A1 | 4/2008 | Aram et al. |
| 2008/0091273 | A1 | 4/2008 | Hazebrouck |
| 2008/0103603 | A1 | 5/2008 | Hintermann |
| 2008/0114462 | A1 | 5/2008 | Guidera et al. |
| 2008/0119938 | A1 | 5/2008 | Oh |
| 2008/0119940 | A1 | 5/2008 | Otto et al. |
| 2008/0140212 | A1 | 6/2008 | Metzger et al. |
| 2008/0161918 | A1 | 7/2008 | Fankhauser et al. |
| 2008/0167722 | A1 | 7/2008 | Metzger et al. |
| 2008/0215156 | A1 | 9/2008 | Duggal et al. |
| 2008/0243258 | A1 | 10/2008 | Sancheti |
| 2008/0262624 | A1 | 10/2008 | White et al. |
| 2008/0281426 | A1 | 11/2008 | Fitz et al. |
| 2008/0288080 | A1 | 11/2008 | Sancheti |
| 2008/0300689 | A1 | 12/2008 | Mc Kinnon et al. |
| 2008/0300690 | A1 | 12/2008 | Burstein et al. |
| 2009/0005708 | A1 | 1/2009 | Johanson et al. |
| 2009/0036992 | A1 | 2/2009 | Tsakonas |
| 2009/0043395 | A1 | 2/2009 | Hotokebuchi et al. |
| 2009/0043396 | A1 | 2/2009 | Komistek |
| 2009/0062806 | A1 | 3/2009 | Scott et al. |
| 2009/0082873 | A1 | 3/2009 | Hazebrouck et al. |
| 2009/0088862 | A1 | 4/2009 | Thomas et al. |
| 2009/0125114 | A1 | 5/2009 | May et al. |
| 2009/0149963 | A1 | 6/2009 | Sekel |
| 2009/0149964 | A1 | 6/2009 | May et al. |
| 2009/0204221 | A1 | 8/2009 | Walker |
| 2009/0204222 | A1 | 8/2009 | Burstein et al. |
| 2009/0210066 | A1 | 8/2009 | Jasty |
| 2009/0222103 | A1 | 9/2009 | Fitz et al. |
| 2009/0259314 | A1 | 10/2009 | Linder-ganz et al. |
| 2009/0264894 | A1 | 10/2009 | Wasielewski |
| 2009/0265011 | A1 | 10/2009 | Mandell |
| 2009/0265013 | A1 | 10/2009 | Mandell |
| 2009/0287310 | A1 | 11/2009 | Fisher et al. |
| 2009/0306786 | A1 | 12/2009 | Samuelson |
| 2009/0306787 | A1 | 12/2009 | Crabtree et al. |
| 2009/0319047 | A1 | 12/2009 | Walker |
| 2009/0319048 | A1 | 12/2009 | Shah et al. |
| 2009/0319049 | A1 | 12/2009 | Shah et al. |
| 2009/0326663 | A1 | 12/2009 | Dun |
| 2009/0326665 | A1 | 12/2009 | Wyss et al. |
| 2009/0326666 | A1 | 12/2009 | Wyss et al. |
| 2009/0326668 | A1 | 12/2009 | Dun |
| 2010/0010494 | A1 | 1/2010 | Quiro |
| 2010/0016976 | A1 | 1/2010 | Siebel |
| 2010/0016977 | A1 | 1/2010 | Masini |
| 2010/0016978 | A1 | 1/2010 | Williams et al. |
| 2010/0016979 | A1 | 1/2010 | Wyss et al. |
| 2010/0036499 | A1 | 2/2010 | Pinskerova |
| 2010/0036500 | A1 | 2/2010 | Heldreth et al. |
| 2010/0063594 | A1 | 3/2010 | Hazebrouck et al. |
| 2010/0063595 | A1 | 3/2010 | Dietz |
| 2010/0076563 | A1 | 3/2010 | Otto et al. |
| 2010/0082111 | A1 | 4/2010 | Thomas |
| 2010/0100011 | A1 | 4/2010 | Roche |
| 2010/0100189 | A1 | 4/2010 | Metzger |
| 2010/0100191 | A1 | 4/2010 | May et al. |
| 2010/0125339 | A1 | 5/2010 | Earl et al. |
| 2010/0152858 | A1 | 6/2010 | Lu et al. |
| 2010/0191298 | A1 | 7/2010 | Earl et al. |
| 2010/0191341 | A1 | 7/2010 | Byrd |
| 2010/0198275 | A1 | 8/2010 | Chana et al. |
| 2010/0222890 | A1 | 9/2010 | Barnett et al. |
| 2010/0249660 | A1 | 9/2010 | Sherman et al. |
| 2010/0249789 | A1 | 9/2010 | Rock et al. |
| 2010/0262253 | A1 | 10/2010 | Cipolletti et al. |
| 2010/0286788 | A1 | 11/2010 | Komistek |
| 2010/0292804 | A1 | 11/2010 | Samuelson |
| 2010/0305708 | A1 | 12/2010 | Lang |
| 2010/0329530 | A1 | 12/2010 | Lang et al. |
| 2011/0022179 | A1 | 1/2011 | Andriacchi et al. |
| 2011/0029091 | A1 | 2/2011 | Bojarski et al. |
| 2011/0040387 | A1 | 2/2011 | Ries et al. |
| 2011/0066246 | A1 | 3/2011 | Ries et al. |
| 2011/0082558 | A1 | 4/2011 | Kim et al. |
| 2011/0082559 | A1 | 4/2011 | Hartdegen et al. |
| 2011/0087332 | A1 | 4/2011 | Bojarski et al. |
| 2011/0098824 | A1 | 4/2011 | Jukes et al. |
| 2011/0100011 | A1 | 5/2011 | Staffend |
| 2011/0125278 | A1 | 5/2011 | Bercovy et al. |

(56) References Cited

U.S. PATENT DOCUMENTS

| | | |
|---|---|---|
| 2011/0144760 A1 | 6/2011 | Wong et al. |
| 2011/0153026 A1 | 6/2011 | Heggendorn et al. |
| 2011/0190898 A1 | 8/2011 | Lenz et al. |
| 2011/0202139 A1 | 8/2011 | Metzger et al. |
| 2011/0251695 A1 | 10/2011 | Lenz et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford |
| 2012/0095563 A1 | 4/2012 | Sanford et al. |
| 2012/0101585 A1 | 4/2012 | Parisi et al. |
| 2012/0158152 A1 | 6/2012 | Claypool et al. |
| 2012/0179069 A1 | 7/2012 | Amirouche |
| 2012/0185054 A1 | 7/2012 | Maloney et al. |
| 2012/0185055 A1 | 7/2012 | Maloney et al. |
| 2012/0232429 A1 | 9/2012 | Fischer et al. |
| 2012/0290088 A1 | 11/2012 | Amirouche et al. |
| 2012/0296437 A1 | 11/2012 | Wyss et al. |
| 2012/0310246 A1 | 12/2012 | Belcher et al. |
| 2012/0310361 A1 | 12/2012 | Zubok et al. |
| 2012/0323335 A1 | 12/2012 | Parisi et al. |
| 2012/0323336 A1 | 12/2012 | Parisi et al. |
| 2013/0013076 A1 | 1/2013 | Fisher et al. |
| 2013/0024001 A1 | 1/2013 | Wentorf et al. |
| 2013/0079671 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0131816 A1 | 5/2013 | Parisi et al. |
| 2013/0131817 A1 | 5/2013 | Parisi et al. |
| 2013/0131818 A1 | 5/2013 | Parisi et al. |
| 2013/0131819 A1 | 5/2013 | Parisi et al. |
| 2013/0131820 A1 | 5/2013 | Wentorf et al. |
| 2013/0173010 A1 | 7/2013 | Irwin |
| 2013/0226305 A1 | 8/2013 | Donno et al. |
| 2013/0253378 A1 | 9/2013 | Claypool et al. |
| 2013/0261504 A1 | 10/2013 | Claypool et al. |
| 2013/0261757 A1 | 10/2013 | Claypool et al. |
| 2013/0261758 A1 | 10/2013 | Claypool et al. |
| 2013/0345820 A1 | 12/2013 | Maloney et al. |
| 2014/0025175 A1 | 1/2014 | Wentorf et al. |
| 2014/0025176 A1 | 1/2014 | Wentorf |
| 2014/0025177 A1 | 1/2014 | Wentorf et al. |
| 2014/0052268 A1 | 2/2014 | Sanford et al. |
| 2014/0052269 A1 | 2/2014 | Claypool et al. |
| 2014/0156015 A1 | 6/2014 | Parisi et al. |
| 2014/0163687 A1 | 6/2014 | Parisi et al. |
| 2014/0249641 A1 | 9/2014 | Wentorf et al. |
| 2014/0257505 A1 | 9/2014 | Parisi et al. |
| 2014/0257506 A1 | 9/2014 | Sanford et al. |
| 2014/0296859 A1 | 10/2014 | Claypool et al. |
| 2015/0005890 A1 | 1/2015 | Parisi et al. |
| 2015/0025644 A1 | 1/2015 | Heggendorn et al. |
| 2015/0066150 A1 | 3/2015 | Dai et al. |
| 2015/0088140 A1 | 3/2015 | Toler et al. |
| 2015/0190243 A1 | 7/2015 | Claypool et al. |
| 2015/0257889 A1 | 9/2015 | Kang |
| 2015/0282936 A1 | 10/2015 | Parisi et al. |
| 2015/0320564 A1 | 11/2015 | Parisi et al. |
| 2015/0359642 A1 | 12/2015 | Claypool et al. |
| 2016/0030053 A1 | 2/2016 | Yager et al. |
| 2016/0038294 A1 | 2/2016 | Parisi et al. |
| 2016/0045322 A1 | 2/2016 | Parisi et al. |
| 2016/0135959 A1 | 5/2016 | Sanford et al. |
| 2016/0158019 A1 | 6/2016 | Grey et al. |
| 2016/0184107 A1 | 6/2016 | Parisi et al. |
| 2016/0287397 A1 | 10/2016 | Wentorf |
| 2016/0324647 A1 | 11/2016 | Claypool et al. |
| 2017/0079801 A1 | 3/2017 | Drury et al. |
| 2017/0143324 A1 | 5/2017 | Toler et al. |
| 2017/0156736 A1 | 6/2017 | Claypool et al. |
| 2017/0231773 A1 | 8/2017 | Lu |
| 2017/0266011 A1 | 9/2017 | Wentorf et al. |
| 2017/0281354 A1 | 10/2017 | Soffiatti et al. |
| 2018/0000601 A1 | 1/2018 | Sanford et al. |
| 2018/0000602 A1 | 1/2018 | Wentorf et al. |
| 2018/0000612 A1 | 1/2018 | Claypool et al. |
| 2018/0021143 A1 | 1/2018 | Parisi et al. |
| 2018/0021144 A1 | 1/2018 | Parisi et al. |
| 2018/0085225 A1 | 3/2018 | Wentorf et al. |
| 2018/0161166 A1 | 6/2018 | Dai et al. |
| 2018/0256346 A1 | 9/2018 | Byrd et al. |
| 2018/0325684 A1 | 11/2018 | Croll |
| 2019/0142594 A1 | 5/2019 | Yager |
| 2019/0209333 A1 | 7/2019 | Drury et al. |
| 2019/0328535 A1 | 10/2019 | Drury et al. |
| 2019/0350718 A1 | 11/2019 | Parisi et al. |
| 2020/0030106 A1 | 1/2020 | Wentorf et al. |
| 2020/0060833 A1 | 2/2020 | Arnold et al. |
| 2020/0069433 A1 | 3/2020 | Croll |
| 2020/0113702 A1 | 4/2020 | Sanford et al. |
| 2020/0146830 A1 | 5/2020 | Dai et al. |
| 2020/0237518 A1 | 7/2020 | Byrd et al. |
| 2021/0022875 A1 | 1/2021 | Drury et al. |
| 2021/0113340 A1 | 4/2021 | Parisi et al. |
| 2022/0096243 A1 | 3/2022 | Wentorf et al. |
| 2022/0233321 A1 | 7/2022 | Croll |
| 2022/0241081 A1 | 8/2022 | Garino |
| 2023/0113335 A1 | 4/2023 | Byrd et al. |
| 2024/0000575 A1 | 1/2024 | Drury et al. |
| 2025/0169959 A1 | 5/2025 | Wentorf et al. |

FOREIGN PATENT DOCUMENTS

| | | |
|---|---|---|
| CA | 2190029 A1 | 11/1995 |
| CA | 2856070 C | 7/2016 |
| CH | 687584 A5 | 1/1997 |
| CN | 1087506 A | 6/1994 |
| CN | 1174498 A | 2/1998 |
| CN | 1179709 A | 4/1998 |
| CN | 1440262 A | 9/2003 |
| CN | 1549695 A | 11/2004 |
| CN | 2768715 Y | 4/2006 |
| CN | 1780594 A | 5/2006 |
| CN | 1874738 A | 12/2006 |
| CN | 101214175 A | 7/2008 |
| CN | 101222886 A | 7/2008 |
| CN | 101288597 A | 10/2008 |
| CN | 101347359 A | 1/2009 |
| CN | 201175391 Y | 1/2009 |
| CN | 101361684 A | 2/2009 |
| CN | 101401750 A | 4/2009 |
| CN | 101426453 A | 5/2009 |
| CN | 101522136 A | 9/2009 |
| CN | 101646392 A | 2/2010 |
| CN | 101658446 A | 3/2010 |
| CN | 101683289 A | 3/2010 |
| CN | 101711701 A | 5/2010 |
| CN | 101795643 A | 8/2010 |
| CN | 101835441 A | 9/2010 |
| CN | 102018584 A | 4/2011 |
| CN | 102048594 A | 5/2011 |
| CN | 102058446 A | 5/2011 |
| CN | 102058448 A | 5/2011 |
| CN | 102917670 A | 2/2013 |
| CN | 103118634 A | 5/2013 |
| CN | 103118635 A | 5/2013 |
| CN | 103118636 A | 5/2013 |
| CN | 103370025 A | 10/2013 |
| CN | 103379880 A | 10/2013 |
| CN | 103732186 A | 4/2014 |
| CN | 104039273 A | 9/2014 |
| CN | 104066402 A | 9/2014 |
| CN | 104093380 A | 10/2014 |
| CN | 104135968 A | 11/2014 |
| CN | 104135969 A | 11/2014 |
| CN | 104203160 A | 12/2014 |
| CN | 104321263 A | 1/2015 |
| CN | 104379094 A | 2/2015 |
| CN | 104736105 A | 6/2015 |
| CN | 105055052 A | 11/2015 |
| CN | 105167889 A | 12/2015 |
| CN | 103118634 B | 8/2016 |

(56) References Cited

FOREIGN PATENT DOCUMENTS

| CN | 103118636 B | 8/2016 |
| CN | 104093380 B | 8/2016 |
| CN | 106037997 A | 10/2016 |
| CN | 103370025 B | 11/2016 |
| CN | 106073949 A | 11/2016 |
| CN | 106214292 A | 12/2016 |
| CN | 108135701 A | 6/2018 |
| CN | 106073949 B | 12/2018 |
| CN | 109310504 A | 2/2019 |
| CN | 110022798 A | 7/2019 |
| CN | 110402123 A | 11/2019 |
| CN | 110636818 A | 12/2019 |
| CN | 113317912 A | 8/2021 |
| CN | 113317912 B | 6/2024 |
| EP | 0021421 A1 | 1/1981 |
| EP | 0303467 A2 | 2/1989 |
| EP | 0327495 A2 | 8/1989 |
| EP | 0340919 A1 | 11/1989 |
| EP | 0372811 A1 | 6/1990 |
| EP | 0306744 B1 | 4/1992 |
| EP | 0495340 A1 | 7/1992 |
| EP | 0636353 A1 | 2/1995 |
| EP | 0672397 A1 | 9/1995 |
| EP | 0552950 B1 | 9/1996 |
| EP | 0536457 B1 | 1/1997 |
| EP | 0642328 B1 | 12/1998 |
| EP | 0592750 B1 | 1/1999 |
| EP | 0903125 A1 | 3/1999 |
| EP | 0956836 A1 | 11/1999 |
| EP | 0956836 B1 | 11/1999 |
| EP | 1025818 A2 | 8/2000 |
| EP | 1097679 A1 | 5/2001 |
| EP | 0709074 B1 | 12/2002 |
| EP | 1327424 A1 | 7/2003 |
| EP | 1378216 A2 | 1/2004 |
| EP | 1477143 A1 | 11/2004 |
| EP | 1568336 A1 | 8/2005 |
| EP | 1719478 A2 | 11/2006 |
| EP | 1722721 A1 | 11/2006 |
| EP | 1354571 B1 | 6/2007 |
| EP | 1396240 B1 | 4/2008 |
| EP | 1604623 B1 | 6/2008 |
| EP | 1996122 A1 | 12/2008 |
| EP | 0927009 B1 | 1/2009 |
| EP | 2011455 A1 | 1/2009 |
| EP | 1696835 B1 | 2/2009 |
| EP | 1132063 A2 | 9/2009 |
| EP | 1591082 B1 | 9/2009 |
| EP | 2140838 A2 | 1/2010 |
| EP | 2140839 A1 | 1/2010 |
| EP | 2143403 A1 | 1/2010 |
| EP | 2237177 A1 | 10/2010 |
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| EP | 2595573 A1 | 5/2013 |
| EP | 2782525 A1 | 10/2014 |
| EP | 2830543 A1 | 2/2015 |
| EP | 2830544 A1 | 2/2015 |
| EP | 2830544 B1 | 9/2016 |
| EP | 2918235 B1 | 1/2017 |
| EP | 3143964 A2 | 3/2017 |
| EP | 2595574 B1 | 5/2017 |
| EP | 3111894 B1 | 12/2018 |
| EP | 3241527 B1 | 10/2024 |
| EP | 3621558 B1 | 1/2025 |
| EP | 3848005 B1 | 4/2025 |
| EP | 4014930 B1 | 4/2025 |
| EP | 4014929 B1 | 6/2025 |
| FR | 2728782 A1 | 7/1996 |
| FR | 2736819 A1 | 1/1997 |
| FR | 2747914 A1 | 10/1997 |
| FR | 2773059 A1 | 7/1999 |
| FR | 2778332 A1 | 11/1999 |
| FR | 2788964 A1 | 8/2000 |
| FR | 2824260 A1 | 11/2002 |
| FR | 2852819 A1 | 10/2004 |
| FR | 2926719 A1 | 7/2009 |
| GB | 225347 A | 12/1924 |
| GB | 2253147 A | 9/1992 |
| GB | 2296443 A | 7/1996 |
| GB | 2345446 A | 7/2000 |
| IN | 7145DELNP2014 A | 4/2015 |
| JP | 61247449 A | 11/1986 |
| JP | 62270153 A | 11/1987 |
| JP | 06203576 A | 7/1994 |
| JP | 09289998 A | 11/1997 |
| JP | 09511668 A | 11/1997 |
| JP | 2000000255 A | 1/2000 |
| JP | 2000245758 A | 9/2000 |
| JP | 2003516183 A | 5/2003 |
| JP | 2004166802 A | 6/2004 |
| JP | 2004254811 A | 9/2004 |
| JP | 3734270 B2 | 1/2006 |
| JP | 2007054488 A | 3/2007 |
| JP | 2007509709 A | 4/2007 |
| JP | 2007222616 A | 9/2007 |
| JP | 2009082713 A | 4/2009 |
| JP | 2009245619 A | 10/2009 |
| JP | 2010022827 A | 2/2010 |
| JP | 2010188051 A | 9/2010 |
| JP | 2010240406 A | 10/2010 |
| JP | 2010259808 A | 11/2010 |
| JP | 2011004848 A | 1/2011 |
| JP | 2011092738 A | 5/2011 |
| JP | 2012500667 A | 1/2012 |
| JP | 2012531265 A | 12/2012 |
| JP | 2015512307 A | 4/2013 |
| JP | 2013535276 A | 9/2013 |
| JP | 2013536005 A | 9/2013 |
| JP | 2013536006 A | 9/2013 |
| JP | 2013536007 A | 9/2013 |
| JP | 2014505517 A | 3/2014 |
| JP | 2014508554 A | 4/2014 |
| JP | 2014522292 A | 9/2014 |
| JP | 2014239900 A | 12/2014 |
| JP | 2015502203 A | 1/2015 |
| JP | 2015504333 A | 2/2015 |
| JP | 2015504759 A | 2/2015 |
| JP | 2015513966 A | 5/2015 |
| JP | 2015231566 A | 12/2015 |
| JP | 2016028729 A | 3/2016 |
| JP | 5980341 B2 | 8/2016 |
| JP | 2016195841 A | 11/2016 |
| JP | 2017221732 A | 12/2017 |
| JP | 2021142355 A | 9/2021 |
| KR | 20150096186 A | 8/2015 |
| WO | WO-9305729 A2 | 4/1993 |
| WO | WO-9409725 A1 | 5/1994 |
| WO | WO-9514444 A1 | 6/1995 |
| WO | WO-9514446 A1 | 6/1995 |
| WO | WO-9530389 A1 | 11/1995 |
| WO | WO-9535074 A1 | 12/1995 |
| WO | WO-9934755 A1 | 7/1999 |
| WO | WO-0141680 A1 | 6/2001 |
| WO | WO-200141680 A1 | 6/2001 |
| WO | WO-03099106 A2 | 12/2003 |
| WO | WO-2004058108 A1 | 7/2004 |
| WO | WO-2005037147 A1 | 4/2005 |
| WO | WO-2005051240 A1 | 6/2005 |
| WO | WO-2005122967 A1 | 12/2005 |
| WO | WO-2006058057 A2 | 6/2006 |
| WO | WO-2006092167 A1 | 9/2006 |
| WO | WO-2007108804 A1 | 9/2007 |
| WO | WO-2007109641 A2 | 9/2007 |
| WO | WO-2007119173 A2 | 10/2007 |
| WO | WO-2009029631 A1 | 3/2009 |
| WO | WO-2009088235 A2 | 7/2009 |
| WO | WO-2009088236 A2 | 7/2009 |
| WO | WO-2009088238 A2 | 7/2009 |
| WO | WO-2009105495 A1 | 8/2009 |

(56) References Cited

FOREIGN PATENT DOCUMENTS

| WO | WO-2010001010 A1 | 1/2010 |
| WO | WO-2010008803 A2 | 1/2010 |
| WO | WO-2010011590 A1 | 1/2010 |
| WO | WO-2010022272 A1 | 2/2010 |
| WO | WO-2010023062 A2 | 3/2010 |
| WO | WO-2010045537 A1 | 4/2010 |
| WO | WO-2010075365 A2 | 7/2010 |
| WO | WO-2011043955 A1 | 4/2011 |
| WO | WO-2011063123 A2 | 5/2011 |
| WO | WO-2011071979 A2 | 6/2011 |
| WO | WO-2011072235 A2 | 6/2011 |
| WO | WO-2011110865 A2 | 9/2011 |
| WO | WO-2012004580 A1 | 1/2012 |
| WO | WO-2012018563 A1 | 2/2012 |
| WO | WO-2012018564 A1 | 2/2012 |
| WO | WO-2012018565 A1 | 2/2012 |
| WO | WO-2012018566 A1 | 2/2012 |
| WO | WO-2012018567 A1 | 2/2012 |
| WO | WO-2012020460 A1 | 2/2012 |
| WO | WO-2012082628 A1 | 6/2012 |
| WO | WO-2012083280 A1 | 6/2012 |
| WO | WO-2012112698 A2 | 8/2012 |
| WO | WO-2012173704 A1 | 12/2012 |
| WO | WO-2012173706 A1 | 12/2012 |
| WO | WO-2013003433 A1 | 1/2013 |
| WO | WO-2013013094 A1 | 1/2013 |
| WO | WO-2013041905 A1 | 3/2013 |
| WO | WO-2013074142 A1 | 5/2013 |
| WO | WO-2013074143 A1 | 5/2013 |
| WO | WO-2013074144 A1 | 5/2013 |
| WO | WO-2013074145 A1 | 5/2013 |
| WO | WO-2013077919 A1 | 5/2013 |
| WO | WO-2013115849 A1 | 8/2013 |
| WO | WO-2013148954 A1 | 10/2013 |
| WO | WO-2013148960 A1 | 10/2013 |
| WO | WO-2017053196 A1 | 3/2017 |
| WO | WO-2018165442 A1 | 9/2018 |
| WO | WO-2018208612 A1 | 11/2018 |

OTHER PUBLICATIONS

"U.S. Appl. No. 16/849,394, Examiner Interview Summary mailed Aug. 29, 2022", 2 pgs.
"U.S. Appl. No. 16/849,394, Notice of Allowance mailed Sep. 15, 2022", 8 pgs.
"U.S. Appl. No. 16/849,394, Response filed Aug. 24, 2022 to Non Final Office Action mailed Jun. 3, 2022", 15 pgs.
"U.S. Appl. No. 18/081,481, Preliminary Amendment filed Jan. 11, 2023", 6 pgs.
"European Application Serial No. 18726670.5, Communication Pursuant to Article 94(3) EPC mailed Dec. 15, 2022", 5 pgs.
"European Application Serial No. 21177256.1, Response filed Dec. 21, 2022 to Extended European Search Report mailed May 17, 2022", 35 pgs.
"European Application Serial No. 21178298.2, Response filed Dec. 21, 2022 to Extended European Search Report mailed Mar. 1, 2022", 23 pgs.
"Japanese Application Serial No. 2021-097369, Response filed Sep. 12, 2022 to Notification of Reasons for Rejection mailed Jun. 14, 2022", w/ English claims, 17 pgs.
"U.S. Appl. No. 13/087,610, Non Final Office Action mailed Feb. 26, 2013", 7 pgs.
"U.S. Appl. No. 13/087,610, Notice of Allowance mailed Jun. 28, 2013", 6 pgs.
"U.S. Appl. No. 13/087,610, Notice of Allowance mailed Oct. 8, 2013", 7 pgs.
"U.S. Appl. No. 13/087,610, Response filed May 24, 2013 to Non Final Office Action mailed Feb. 26, 2013", 15 pgs.
"U.S. Appl. No. 13/189,324, Examiner Interview Summary mailed Jan. 13, 2014", 4 pgs.
"U.S. Appl. No. 13/189,324, Final Office Action mailed Jul. 16, 2013", 19 pgs.
"U.S. Appl. No. 13/189,324, Non Final Office Action mailed Dec. 11, 2012", 19 pgs.
"U.S. Appl. No. 13/189,324, Notice of Allowance mailed Feb. 20, 2014", 8 pgs.
"U.S. Appl. No. 13/189,324, PTO Response to 312 Amendment mailed May 29, 2014", 2 pgs.
"U.S. Appl. No. 13/189,324, Response filed Jan. 15, 2014 to Final Office Action dated Jul. 16, 2013", 23 pgs.
"U.S. Appl. No. 13/189,324, Response filed Jun. 10, 2013 to Non Final Office Action mailed Dec. 11, 2012", 24 pgs.
"U.S. Appl. No. 13/189,328, Non Final Office Action mailed Mar. 19, 2013", 10 pgs.
"U.S. Appl. No. 13/189,328, Notice of Allowance mailed Oct. 8, 2013", 12 pgs.
"U.S. Appl. No. 13/189,328, PTO Response to 312 Amendment mailed Dec. 13, 2013", 2 pgs.
"U.S. Appl. No. 13/189,328, Response filed Jan. 10, 2013 to Restriction Requirement mailed Dec. 10, 2012", 9 pgs.
"U.S. Appl. No. 13/189,328, Response filed Jul. 18, 2013 to Non Final Office Action mailed Mar. 19, 2013", 16 pgs.
"U.S. Appl. No. 13/189,328, Restriction Requirement mailed Dec. 10, 2012", 6 pgs.
"U.S. Appl. No. 13/189,336, Notice of Allowance mailed Sep. 13, 2013", 30 pgs.
"U.S. Appl. No. 13/189,336, PTO Response to 312 Amendment mailed Nov. 25, 2013", 2 pgs.
"U.S. Appl. No. 13/189,336, Response filed Apr. 15, 2013 to Restriction Requirement mailed Jan. 30, 2013", 21 pgs.
"U.S. Appl. No. 13/189,336, Response filed Jul. 17, 2013 to Restriction Requirement mailed Jun. 17, 2013", 20 pgs.
"U.S. Appl. No. 13/189,336, Restriction Requirement mailed Jan. 30, 2013", 5 pgs.
"U.S. Appl. No. 13/189,336, Restriction Requirement mailed Jun. 17, 2013", 6 pgs.
"U.S. Appl. No. 13/189,338, Notice of Allowance mailed Sep. 23, 2013", 23 pgs.
"U.S. Appl. No. 13/189,338, Response filed Apr. 15, 2013 to Restriction Requirement mailed Feb. 14, 2013", 18 pgs.
"U.S. Appl. No. 13/189,338, Response filed Jul. 17, 2013 to Restriction Requirement mailed Jun. 17, 2013", 16 pgs.
"U.S. Appl. No. 13/189,338, Restriction Requirement mailed Feb. 14, 2013", 5 pgs.
"U.S. Appl. No. 13/189,338, Restriction Requirement mailed Jun. 17, 2013", 6 pgs.
"U.S. Appl. No. 13/189,339, Notice of Allowance mailed Sep. 20, 2013", 16 pgs.
"U.S. Appl. No. 13/189,339, Response filed Apr. 15, 2013 to Restriction Requirement mailed Mar. 6, 2013", 11 pgs.
"U.S. Appl. No. 13/189,339, Response filed Jul. 17, 2013 to Restriction Requirement mailed Jun. 17, 2013", 10 pgs.
"U.S. Appl. No. 13/189,339, Restriction Requirement mailed Mar. 6, 2013", 6 pgs.
"U.S. Appl. No. 13/189,339, Restriction Requirement mailed Jun. 17, 2013", 7 pgs.
"U.S. Appl. No. 13/229,103, Applicant Interview Summary mailed Sep. 23, 2013", 2 pgs.
"U.S. Appl. No. 13/229,103, Examiner Interview Summary mailed Sep. 13, 2013", 3 pgs.
"U.S. Appl. No. 13/229,103, Non Final Office Action mailed Apr. 1, 2013", 18 pgs.
"U.S. Appl. No. 13/229,103, Notice of Allowance mailed Sep. 18, 2013", 9 pgs.
"U.S. Appl. No. 13/229,103, Response filed Jul. 1, 2013 to Non Final Office Action mailed Apr. 1, 2013", 19 pgs.
"U.S. Appl. No. 13/229,103, Supplemental Notice of Allowability mailed Oct. 18, 2013", 2 pgs.
"U.S. Appl. No. 13/459,037, Final Office Action mailed Sep. 23, 2013", 9 pgs.
"U.S. Appl. No. 13/459,037, Non Final Office Action mailed Apr. 23, 2013", 10 pgs.
"U.S. Appl. No. 13/459,037, Notice of Allowance mailed Jun. 13, 2014", 9 pgs.

(56)　　　　　　References Cited

OTHER PUBLICATIONS

"U.S. Appl. No. 13/459,037, Preliminary Amendment filed Apr. 27, 2012", 3 pgs.

"U.S. Appl. No. 13/459,037, Response filed Mar. 21, 2014 to Final Office Action mailed Sep. 23, 2013", 15 pgs.

"U.S. Appl. No. 13/459,037, Response filed Mar. 28, 2013 to Restriction Requirement mailed Feb. 26, 2013", 9 pgs.

"U.S. Appl. No. 13/459,037, Response filed Jul. 23, 2013 to Non Final Office Action mailed Apr. 23, 2013", 19 pgs.

"U.S. Appl. No. 13/459,037, Restriction Requirement mailed Feb. 26, 2013", 6 pgs.

"U.S. Appl. No. 13/459,041, Non Final Office Action mailed Jan. 15, 2014", 16 pgs.

"U.S. Appl. No. 13/459,041, Non Final Office Action mailed Sep. 9, 2014", 14 pgs.

"U.S. Appl. No. 13/459,041, Notice of Allowance mailed Apr. 2, 2015", 10 pgs.

"U.S. Appl. No. 13/459,041, Preliminary Amendment mailed Apr. 27, 2012", 7 pgs.

"U.S. Appl. No. 13/459,041, PTO Response to Rule 312 Communication mailed Jun. 9, 2015", 2 pgs.

"U.S. Appl. No. 13/459,041, Response filed May 15, 2014 to Non-Final Office Action dated Jan. 15, 2014", 24 pgs.

"U.S. Appl. No. 13/459,041, Response filed Sep. 23, 2013 to Restriction Requirement mailed Jul. 25, 2013", 18 pgs.

"U.S. Appl. No. 13/459,041, Response filed Dec. 9, 2014 to Non-Final Office Action mailed Sep. 9, 2014", 23 pgs.

"U.S. Appl. No. 13/459,041, Restriction Requirement mailed Jul. 25, 2013", 9 pgs.

"U.S. Appl. No. 13/459,048, Non Final Office Action malled Jul. 11, 2013", 6 pgs.

"U.S. Appl. No. 13/459,048, Notice of Allowance mailed Nov. 26, 2013", 10 pgs.

"U.S. Appl. No. 13/459,048, Preliminary Amendment filed Apr. 27, 2012", 7 pgs.

"U.S. Appl. No. 13/459,048, Response filed Nov. 11, 2013 to Non-Final Office Action mailed Jul. 11, 2013", 16 pgs.

"U.S. Appl. No. 13/459,056, Examiner Interview Summary mailed Dec. 26, 2013", 3 pgs.

"U.S. Appl. No. 13/459,056, Non Final Office Action mailed Jul. 25, 2013", 11 pgs.

"U.S. Appl. No. 13/459,056, Notice of Allowance mailed Feb. 20, 2014", 5 pgs.

"U.S. Appl. No. 13/459,056, Preliminary Amendment filed Apr. 27, 2012", 7 pgs.

"U.S. Appl. No. 13/459,056, PTO Response to Rule 312 Communication mailed May 22, 2014", 2 pgs.

"U.S. Appl. No. 13/459,056, Response filed Jan. 24, 2014 to Non-Final office Action mailed Jul. 25, 2013", 27 pgs.

"U.S. Appl. No. 13/459,056, Response filed Apr. 8, 2013 to Restriction Requirement mailed Mar. 6, 2013", 15 pgs.

"U.S. Appl. No. 13/459,056, Restriction Requirement mailed Mar. 6, 2013", 6 pgs.

"U.S. Appl. No. 13/593,339, Non Final Office Action mailed Oct. 4, 2013", 7 pgs.

"U.S. Appl. No. 13/593,339, Notice of Allowance mailed Feb. 14, 2014", 9 pgs.

"U.S. Appl. No. 13/593,339, Preliminary Amendment filed Aug. 23, 2012", 6 pgs.

"U.S. Appl. No. 13/593,339, Response filed Jan. 31, 2014 to Non-Final Office Action dated Oct. 4, 2013", 19 pgs.

"U.S. Appl. No. 13/593,339, Response filed Aug. 30, 2013 to Restriction Requirement mailed Aug. 1, 2013", 14 pgs.

"U.S. Appl. No. 13/593,339, Restriction Requirement mailed Aug. 1, 2013", 5 pgs.

"U.S. Appl. No. 13/593,339, Supplemental Notice of Allowability mailed Mar. 31, 2014", 2 pgs.

"U.S. Appl. No. 13/594,543, Corrected Notice of Allowance mailed Mar. 16, 2016", 2 pgs.

"U.S. Appl. No. 13/594,543, Examiner Interview Summary mailed Jan. 22, 2016", 3 pgs.

"U.S. Appl. No. 13/594,543, Final Office Action mailed Jul. 17, 2014", 12 pgs.

"U.S. Appl. No. 13/594,543, Final Office Action mailed Nov. 20, 2015", 28 pgs.

"U.S. Appl. No. 13/594,543, Non Final Office Action mailed Jun. 19, 2015", 30 pgs.

"U.S. Appl. No. 13/594,543, Non Final Office Action mailed Dec. 26, 2013", 15 pgs.

"U.S. Appl. No. 13/594,543, Non-Final Office Action mailed Jan. 9, 2015", 23 pgs.

"U.S. Appl. No. 13/594,543, Notice of Allowance mailed Mar. 1, 2016", 9 pgs.

"U.S. Appl. No. 13/594,543, Preliminary Amendment filed Aug. 24, 2012", 4 pgs.

"U.S. Appl. No. 13/594,543, Response filed Feb. 8, 2016 to Final Office Action mailed Nov. 20, 2015", 17 pgs.

"U.S. Appl. No. 13/594,543, Response filed Apr. 7, 2015 to Non-Final Office Action mailed Jan. 9, 2015", 27 pgs.

"U.S. Appl. No. 13/594,543, Response filed May 7, 2014 to Non-Final office Action mailed Dec. 26, 2013", 17 pgs.

"U.S. Appl. No. 13/594,543, Response filed Sep. 21, 2015 to Non-Final Office Action mailed Jun. 19, 2015", 25 pgs.

"U.S. Appl. No. 13/594,543, Response filed Oct. 11, 2013 to Restriction Requirement mailed Sep. 12, 2013", 8 pgs.

"U.S. Appl. No. 13/594,543, Response filed Dec. 17, 2014 to Final Office Action mailed Jul. 17, 2014", 15 pgs.

"U.S. Appl. No. 13/594,543, Restriction Requirement mailed Sep. 12, 2013", 5 pgs.

"U.S. Appl. No. 13/819,116, Advisory Action mailed Jan. 5, 2016", 3 pgs.

"U.S. Appl. No. 13/819,116, Corrected Notice of Allowance mailed Oct. 21, 2016", 2 pgs.

"U.S. Appl. No. 13/819,116, Examiner Interview Summary mailed Apr. 18, 2016", 11 pgs.

"U.S. Appl. No. 13/819,116, Final Office Action mailed Jul. 26, 2016", 6 pgs.

"U.S. Appl. No. 13/819,116, Final Office Action mailed Oct. 21, 2015", 15 pgs.

"U.S. Appl. No. 13/819,116, Non Final Office Action mailed Feb. 17, 2016", 15 pgs.

"U.S. Appl. No. 13/819,116, Non Final Office Action mailed Jun. 2, 2015", 14 pgs.

"U.S. Appl. No. 13/819,116, Notice of Allowance mailed Sep. 29, 2016", 5 pgs.

"U.S. Appl. No. 13/819,116, Preliminary Amendment filed Feb. 26, 2013", 8 pgs.

"U.S. Appl. No. 13/819,116, Response filed Mar. 27, 2015 to Restriction Requirement mailed Feb. 12, 2015", 11 pgs.

"U.S. Appl. No. 13/819,116, Response filed Apr. 29, 2016 to Non Final Office Action mailed Feb. 17, 2016", 17 pgs.

"U.S. Appl. No. 13/819,116, Response filed Jul. 16, 2015 to Non Final Office Action mailed Jun. 2, 2015", 22 pgs.

"U.S. Appl. No. 13/819,116, Response filed Sep. 14, 2016 Final Office Action mailed Jul. 26, 2016", 10 pgs.

"U.S. Appl. No. 13/819,116, Response filed Dec. 15, 2015 to Final Office Action mailed Oct. 21, 2015", 16 pgs.

"U.S. Appl. No. 13/819,116, Restriction Requirement mailed Feb. 12, 2015", 7 pgs.

"U.S. Appl. No. 13/836,586, Express Abandonment filed May 30, 2014", 1 pg.

"U.S. Appl. No. 13/836,665, Examiner Interview Summary mailed Jul. 17, 2014", 4 pgs.

"U.S. Appl. No. 13/836,665, Final Office Action mailed Jul. 25, 2014", 25 pgs.

"U.S. Appl. No. 13/836,665, Non Final Office Action mailed Jan. 30, 2014", 21 pgs.

"U.S. Appl. No. 13/836,665, Notice of Allowance mailed Jun. 9, 2015", 10 pgs.

"U.S. Appl. No. 13/836,665, Response filed Jan. 23, 2015 to Final Office Action mailed Jul. 25, 2014", 25 pgs.

(56) References Cited

OTHER PUBLICATIONS

"U.S. Appl. No. 13/836,665, Response filed May 30, 2014 to Non-Final Office Action mailed Jan. 30, 2014", 21 pgs.

"U.S. Appl. No. 13/837,294, Final Office Action mailed Apr. 25, 2016", 7 pgs.

"U.S. Appl. No. 13/837,294, Final Office Action mailed Jun. 2, 2016", 7 pgs.

"U.S. Appl. No. 13/837,294, Non Final Office Action mailed Dec. 10, 2015", 8 pgs.

"U.S. Appl. No. 13/837,294, Notice of Allowance mailed Aug. 25, 2016", 5 pgs.

"U.S. Appl. No. 13/837,294, Response filed Mar. 4, 2016 to Non Final Office Action mailed Dec. 10, 2015", 16 pgs.

"U.S. Appl. No. 13/837,294, Response filed Aug. 3, 2016 to Final Office Action mailed Jun. 2, 2016", 7 pgs.

"U.S. Appl. No. 13/837,294, Response filed Oct. 12, 2015 to Restriction Requirement mailed Aug. 24, 2015", 9 pgs.

"U.S. Appl. No. 13/837,294, Restriction Requirement mailed Aug. 24, 2015", 6 pgs.

"U.S. Appl. No. 13/837,774, Examiner Interview Summary mailed Jul. 22, 2014", 4 pgs.

"U.S. Appl. No. 13/837,774, Final Office Action mailed Mar. 17, 2016", 14 pgs.

"U.S. Appl. No. 13/837,774, Final Office Action mailed Jul. 28, 2014", 17 pgs.

"U.S. Appl. No. 13/837,774, Non Final Office Action mailed Feb. 10, 2014", 33 pgs.

"U.S. Appl. No. 13/837,774, Non Final Office Action mailed Sep. 18, 2015", 16 pgs.

"U.S. Appl. No. 13/837,774, Response filed Jan. 28, 2015 to Final Office Action mailed Jul. 28, 2014", 16 pgs.

"U.S. Appl. No. 13/837,774, Response filed Jun. 10, 2014 to Non-Final Office Action mailed Feb. 20, 2014", 29 pgs.

"U.S. Appl. No. 13/837,774, Response filed Jul. 7, 2015 to Restriction Requirement mailed May 20, 2015", 10 pgs.

"U.S. Appl. No. 13/837,774, Response filed Dec. 16, 2015 to Non Final Office Action mailed Sep. 18, 2015", 17 pgs.

"U.S. Appl. No. 13/837,774, Restriction Requirement mailed May 20, 2015", 6 pgs.

"U.S. Appl. No. 14/034,076, Appeal Brief Filed Apr. 18, 2016", 21 pgs.

"U.S. Appl. No. 14/034,076, Final Office Action mailed Dec. 21, 2015", 11 pgs.

"U.S. Appl. No. 14/034,076, Non Final Office Action mailed Jun. 24, 2015", 11 pgs.

"U.S. Appl. No. 14/034,076, Notice of Allowance mailed Oct. 28, 2016", 7 pgs.

"U.S. Appl. No. 14/034,076, Response filed Nov. 16, 2015 to Non Final Office Action mailed Jun. 24, 2015", 13 pgs.

"U.S. Appl. No. 14/034,937, Appeal Brief Filed Sep. 9, 2015", 41 pgs.

"U.S. Appl. No. 14/034,937, Appeal Decision mailed May 30, 2017", 34 pgs.

"U.S. Appl. No. 14/034,937, Final Office Action mailed Jun. 5, 2015", 22 pgs.

"U.S. Appl. No. 14/034,937, Non Final Office Action mailed Jan. 2, 2015", 21 pgs.

"U.S. Appl. No. 14/034,937, Notice of Allowance mailed Aug. 30, 2017", 14 pgs.

"U.S. Appl. No. 14/034,937, Preliminary Amendment filed Sep. 24, 2013", 3 pgs.

"U.S. Appl. No. 14/034,937, PTO Response to Rule 312 Communication mailed Oct. 10, 2017", 2 pgs.

"U.S. Appl. No. 14/034,937, Response filed Mar. 30, 2015 to Non-Final Office Action", 24 pgs.

"U.S. Appl. No. 14/034,937, Response filed Oct. 27, 2014 to Restriction Requirement mailed Sep. 11, 2014", 12 pgs.

"U.S. Appl. No. 14/034,937, Restriction Requirement mailed Sep. 11, 2014", 6 pgs.

"U.S. Appl. No. 14/034,937, Supplemental Preliminary Amendment filed Oct. 24, 2013", 11 pgs.

"U.S. Appl. No. 14/034,944, Non Final Office Action mailed Mar. 3, 2015", 16 pgs.

"U.S. Appl. No. 14/034,944, Notice of Allowance mailed Aug. 28, 2015", 7 pgs.

"U.S. Appl. No. 14/034,944, Preliminary Amendment filed Sep. 24, 2013", 3 pgs.

"U.S. Appl. No. 14/034,944, Response filed Jun. 23, 2015 to Non Final Office Action mailed Mar. 3, 2015", 15 pgs.

"U.S. Appl. No. 14/034,944, Response filed Dec. 15, 2014 to Restriction Requirement mailed Oct. 14, 2014", 12 pgs.

"U.S. Appl. No. 14/034,944, Restriction Requirement mailed Oct. 14, 2014", 6 pgs.

"U.S. Appl. No. 14/034,944, Supplemental Preliminary Amendment filed Oct. 24, 2013", 11 pgs.

"U.S. Appl. No. 14/034,954, Advisory Action mailed Aug. 25, 2015", 3 pgs.

"U.S. Appl. No. 14/034,954, Final Office Action mailed Jun. 1, 2015", 26 pgs.

"U.S. Appl. No. 14/034,954, Non Final Office Action mailed Dec. 19, 2014", 25 pgs.

"U.S. Appl. No. 14/034,954, Notice of Allowance mailed Nov. 20, 2015", 11 pgs.

"U.S. Appl. No. 14/034,954, Preliminary Amendment filed Sep. 24, 2013", 3 pgs.

"U.S. Appl. No. 14/034,954, Response filed Mar. 17, 2015 to Non Final Office Action mailed Dec. 19, 2014", 21 pgs.

"U.S. Appl. No. 14/034,954, Response filed Aug. 3, 2015 to Final Office Action mailed Jun. 1, 2015", 19 pgs.

"U.S. Appl. No. 14/034,954, Response filed Aug. 31, 2015 to Advisory Action mailed Aug. 25, 2015", 21 pgs.

"U.S. Appl. No. 14/034,954, Response filed Oct. 27, 2014 to Restriction Requirement mailed Aug. 25, 2014", 11 pgs.

"U.S. Appl. No. 14/034,954, Restriction Requirement mailed Aug. 25, 2014", 7 pgs.

"U.S. Appl. No. 14/034,954, Supplemental Preliminary Amendment filed Oct. 25, 2013", 8 pgs.

"U.S. Appl. No. 14/034,963, Final Office Action mailed Apr. 13, 2015", 22 pgs.

"U.S. Appl. No. 14/034,963, Final Office Action mailed Oct. 13, 2015", 11 pgs.

"U.S. Appl. No. 14/034,963, Non Final Office Action mailed Jul. 1, 2015", 15 pgs.

"U.S. Appl. No. 14/034,963, Non Final Office Action mailed Nov. 21, 2014", 19 pgs.

"U.S. Appl. No. 14/034,963, Notice of Allowance mailed Dec. 18, 2015", 5 pgs.

"U.S. Appl. No. 14/034,963, Preliminary Amendment filed Sep. 24, 2013", 3 pgs.

"U.S. Appl. No. 14/034,963, Response filed Mar. 20, 2015 to Non-Final Office Action mailed Nov. 21, 2014", 20 pgs.

"U.S. Appl. No. 14/034,963, Response filed Jun. 19, 2015 to Final Office Action mailed Apr. 13, 2015", 17 pgs.

"U.S. Appl. No. 14/034,963, Response filed Sep. 30, 2015 to Non Final Office Action mailed Jul. 1, 2015", 14 pgs.

"U.S. Appl. No. 14/034,963, Response filed Nov. 20, 2015 to Final Office Action mailed Oct. 13, 2015", 12 pgs.

"U.S. Appl. No. 14/063,032, Non Final Office Action mailed Jun. 20, 2014", 6 pgs.

"U.S. Appl. No. 14/063,032, Notice of Allowance mailed Dec. 19, 2014", 6 pgs.

"U.S. Appl. No. 14/063,032, Preliminary Amendment filed Oct. 25, 2013", 3 pgs.

"U.S. Appl. No. 14/063,032, Response filed Oct. 20, 2014 to Non-Final Office Action mailed Jun. 20, 2014", 9 pgs.

"U.S. Appl. No. 14/063,593, Advisory Action mailed Aug. 19, 2016", 3 pgs.

"U.S. Appl. No. 14/063,593, Final Office Action mailed Jun. 9, 2016", 10 pgs.

"U.S. Appl. No. 14/063,593, Non Final Office Action mailed Jan. 25, 2016", 9 pgs.

(56) References Cited

OTHER PUBLICATIONS

"U.S. Appl. No. 14/063,593, Non Final Office Action mailed Nov. 30, 2016", 12 pgs.

"U.S. Appl. No. 14/063,593, Notice of Allowance mailed May 2, 2017", 5 pgs.

"U.S. Appl. No. 14/063,593, Notice of Allowance mailed May 25, 2017", 5 pgs.

"U.S. Appl. No. 14/063,593, Preliminary Amendment filed Oct. 25, 2013", 3 pgs.

"U.S. Appl. No. 14/063,593, Response filed Jan. 4, 2016 to Restriction Requirement mailed Nov. 6, 2015", 6 pgs.

"U.S. Appl. No. 14/063,593, Response filed Feb. 24, 2017 to Non Final Office Action mailed Nov. 30, 2016", 17 pgs.

"U.S. Appl. No. 14/063,593, Response filed Apr. 20, 2016 to Non Final Office Action mailed Jan. 25, 2016", 17 pgs.

"U.S. Appl. No. 14/063,593, Response filed Aug. 11, 2016 to Final Office Action mailed Jun. 9, 2016", 10 pgs.

"U.S. Appl. No. 14/063,593, Restriction Requirement mailed Nov. 6, 2015", 6 pgs.

"U.S. Appl. No. 14/181,033, Non Final Office Action mailed May 1, 2015", 5 pgs.

"U.S. Appl. No. 14/181,033, Notice of Allowance mailed Jul. 17, 2015", 10 pgs.

"U.S. Appl. No. 14/181,033, Response filed Jun. 22, 2015 to Non-Final Office Action mailed May 1, 2015", 11 pgs.

"U.S. Appl. No. 14/278,805, Notice of Allowance mailed Dec. 1, 2015", 8 pgs.

"U.S. Appl. No. 14/278,805, Supplemental Notice of Allowability mailed Jan. 21, 2016", 2 pgs.

"U.S. Appl. No. 14/284,028, Non Final Office Action mailed Jul. 7, 2015", 17 pgs.

"U.S. Appl. No. 14/284,028, Notice of Allowance mailed Nov. 6, 2015", 5 pgs.

"U.S. Appl. No. 14/284,028, Response filed Oct. 6, 2015 to Non Final Office Action mailed Jul. 7, 2015", 15 pgs.

"U.S. Appl. No. 14/284,028, Supplemental Notice of Allowability mailed Feb. 26, 2016", 5 pgs.

"U.S. Appl. No. 14/284,028, Supplemental Preliminary Amendment filed Jul. 8, 2014", 13 pgs.

"U.S. Appl. No. 14/284,144, Final Office Action mailed Aug. 7, 2015", 13 pgs.

"U.S. Appl. No. 14/284,144, Non Final Office Action mailed Mar. 25, 2015", 26 pgs.

"U.S. Appl. No. 14/284,144, Notice of Allowance mailed Oct. 29, 2015", 8 pgs.

"U.S. Appl. No. 14/284,144, Preliminary Amendment filed May 21, 2014", 3 pgs.

"U.S. Appl. No. 14/284,144, Response filed Oct. 9, 2015 to Final Office Action mailed Aug. 7, 2015", 13 pgs.

"U.S. Appl. No. 14/284,144, Response filed Jun. 23, 2015 to Non Final Office Action mailed Mar. 25, 2015", 22 pgs.

"U.S. Appl. No. 14/284,144, Supplemental Preliminary Amendment filed Jul. 3, 2014", 10 pgs.

"U.S. Appl. No. 14/304,009, Notice of Allowance mailed Nov. 16, 2016", 7 pgs.

"U.S. Appl. No. 14/304,009, Preliminary Amendment Filed Jul. 31, 2014", 7 pgs.

"U.S. Appl. No. 14/471,440, Notice of Allowance mailed Nov. 13, 2017", 9 pgs.

"U.S. Appl. No. 14/471,440, Response filed Aug. 16, 2017 to Restriction Requirement mailed Jun. 30, 2017", 8 pgs.

"U.S. Appl. No. 14/471,440, Restriction Requirement mailed Jun. 30, 2017", 6 pgs.

"U.S. Appl. No. 14/490,153, Final Office Action mailed Apr. 15, 2015", 18 pgs.

"U.S. Appl. No. 14/490,153, Non Final Office Action mailed Nov. 12, 2014", 9 pgs.

"U.S. Appl. No. 14/490,153, Notice of Allowance mailed Aug. 14, 2015", 10 pgs.

"U.S. Appl. No. 14/490,153, Preliminary Amendment filed Sep. 18, 2014", 3 pgs.

"U.S. Appl. No. 14/490,153, Response filed Feb. 18, 2015 to Non-Final Office Action mailed Nov. 12, 2014", 14 pgs.

"U.S. Appl. No. 14/490,153, Response filed Jul. 7, 2015 to Final Office Action mailed Apr. 15, 2015", 14 pgs.

"U.S. Appl. No. 14/660,217, Corrected Notice of Allowance mailed May 26, 2016", 3 pgs.

"U.S. Appl. No. 14/660,217, Non Final Office Action mailed Dec. 17, 2015", 8 pgs.

"U.S. Appl. No. 14/660,217, Notice of Allowance mailed Apr. 26, 2016", 5 pgs.

"U.S. Appl. No. 14/660,217, Preliminary Amendment filed Mar. 18, 2015", 9 pgs.

"U.S. Appl. No. 14/660,217, Response filed Mar. 23, 2016 to Non Final Office Action malled Dec. 17, 2015", 14 pgs.

"U.S. Appl. No. 14/740,690, Non Final Office Action mailed Dec. 7, 2016", 19 pgs.

"U.S. Appl. No. 14/740,690, Notice of Allowability mailed Aug. 29, 2017", 2 pgs.

"U.S. Appl. No. 14/740,690, Notice of Allowance mailed Jun. 13, 2017", 9 pgs.

"U.S. Appl. No. 14/740,690, Response filed Mar. 3, 2017 to Non Final Office Action mailed Dec. 7, 2016", 14 pgs.

"U.S. Appl. No. 14/791,952, Corrected Notice of Allowance mailed Jul. 21, 2017", 2 pgs.

"U.S. Appl. No. 14/791,952, Final Office Action mailed Mar. 31, 2017", 8 pgs.

"U.S. Appl. No. 14/791,952, Final Office Action mailed Sep. 1, 2016", 17 pgs.

"U.S. Appl. No. 14/791,952, Non Final Office Action mailed Apr. 21, 2016", 12 pgs.

"U.S. Appl. No. 14/791,952, Non Final Office Action mailed Dec. 29, 2016", 12 pgs.

"U.S. Appl. No. 14/791,952, Notice of Allowance mailed May 30, 2017", 7 pgs.

"U.S. Appl. No. 14/791,952, Preliminary Amendment filed Jul. 7, 2015", 7 pgs.

"U.S. Appl. No. 14/791,952, Response filed Mar. 20, 2017 to Non Final Office Action mailed Dec. 29, 2016", 12 pgs.

"U.S. Appl. No. 14/791,952, Response filed May 17, 2017—to Final Office Action mailed Mar. 31, 2017", 10 pgs.

"U.S. Appl. No. 14/791,952, Response filed Jul. 15, 2016 to Non Final Office Action mailed Apr. 21, 2016", 18 pgs.

"U.S. Appl. No. 14/791,952, Response filed Nov. 21, 2016 to Final Office Action mailed Sep. 1, 2016", 15 pgs.

"U.S. Appl. No. 14/833,385, Examiner Interview Summary mailed Dec. 27, 2017", 3 pgs.

"U.S. Appl. No. 14/833,385, Final Office Action mailed Nov. 13, 2017", 9 pgs.

"U.S. Appl. No. 14/833,385, Non Final Office Action mailed Jun. 19, 2017", 10 pgs.

"U.S. Appl. No. 14/833,385, Preliminary Amendment filed Aug. 25, 2015", 6 pgs.

"U.S. Appl. No. 14/833,385, Response filed May 12, 2017 to Restriction Requirement mailed Mar. 17, 2017", 8 pgs.

"U.S. Appl. No. 14/833,385, Response filed Sep. 18, 2017 to Non Final Office Action mailed Jun. 19, 2017", 14 pgs.

"U.S. Appl. No. 14/833,385, Restriction Requirement mailed Mar. 17, 2017", 6 pgs.

"U.S. Appl. No. 14/918,721, Final Office Action mailed Oct. 20, 2016", 5 pgs.

"U.S. Appl. No. 14/918,721, Non Final Office Action mailed Jun. 16, 2016", 6 pgs.

"U.S. Appl. No. 14/918,721, Notice of Allowance mailed Feb. 1, 2017", 9 pgs.

"U.S. Appl. No. 14/918,721, Preliminary Amendment filed Oct. 23, 2015", 8 pgs.

"U.S. Appl. No. 14/918,721, PTO Response to Rule 312 Communication mailed Mar. 17, 2017", 2 pgs.

"U.S. Appl. No. 14/918,721, Response filed Sep. 12, 2016 to Non Final Office Action mailed Jun. 16, 2016", 12 pgs.

(56) References Cited

OTHER PUBLICATIONS

"U.S. Appl. No. 14/918,721, Response filed Dec. 13, 2016 to Final Office Action mailed Oct. 20, 2016", 9 pgs.
"U.S. Appl. No. 14/926,281, Non Final Office Action mailed Jun. 21, 2017", 17 pgs.
"U.S. Appl. No. 14/926,281, Notice of Allowance mailed Nov. 16, 2017", 9 pgs.
"U.S. Appl. No. 14/926,281, Preliminary Amendment filed Oct. 30, 2015", 8 pgs.
"U.S. Appl. No. 14/926,281, Response filed Sep. 18, 2017 to Non Final Office Action mailed Jun. 21, 2017", 11 pgs.
"U.S. Appl. No. 15,003/091, Preliminary Amendment filed Jan. 22, 2016", 12 pgs.
"U.S. Appl. No. 15/003,091, Non Final Office Action mailed Jun. 20, 2017", 14 pgs.
"U.S. Appl. No. 15/003,091, Notice of Allowance mailed Nov. 6, 2017", 8 pgs.
"U.S. Appl. No. 15/003,091, PTO Response to Rule 312 Communication mailed Jan. 23, 2018", 2 pgs.
"U.S. Appl. No. 15/003,091, Response filed Sep. 20, 2017 to Non Final Office Action mailed Jun. 20, 2017", 17 pgs.
"U.S. Appl. No. 15/045,799, Non Final Office Action mailed Nov. 1, 2016", 8 pgs.
"U.S. Appl. No. 15/045,799, Notice of Allowance mailed Mar. 10, 2017", 10 pgs.
"U.S. Appl. No. 15/045,799, Preliminary Amendment filed Feb. 18, 2016", 9 pgs.
"U.S. Appl. No. 15/045,799, PTO Response to Rule 312 Communication mailed Apr. 18, 2017", 2 pgs.
"U.S. Appl. No. 15/045,799, Response filed Feb. 1, 2017 to Non Final Office Action mailed Nov. 1, 2016", 15 pgs.
"U.S. Appl. No. 15/062,252, Preliminary Amendment filed Mar. 9, 2016", 8 pgs.
"U.S. Appl. No. 15/062,262, Non Final Office Action mailed Jul. 22, 2016", 12 pgs.
"U.S. Appl. No. 15/062,262, Notice of Allowance mailed Jan. 31, 2017", 5 pgs.
"U.S. Appl. No. 15/062,262, PTO Response to Rule 312 Communication mailed Mar. 7, 2017", 2 pgs.
"U.S. Appl. No. 15/062,262, Response filed Oct. 24, 2016 to Non Final Office Action nailed Jul. 22, 2016", 13 pgs.
"U.S. Appl. No. 15/177,734, Non Final Office Action mailed Feb. 10, 2017", 21 pgs.
"U.S. Appl. No. 15/177,734, Notice of Allowance mailed May 17, 2017", 7 pgs.
"U.S. Appl. No. 15/177,734, Preliminary Amendment filed Jun. 22, 2016", 8 pgs.
"U.S. Appl. No. 15/177,734, Response filed Apr. 19, 2017 to Non Final Office Action mailed Feb. 10, 2017", 22 pgs.
"U.S. Appl. No. 15/211,812, Non Final Office Action mailed Jan. 27, 2017", 5 pgs.
"U.S. Appl. No. 15/211,812, Notice of Allowance mailed May 31, 2017", 5 pgs.
"U.S. Appl. No. 15/211,812, Preliminary Amendment filed Sep. 8, 2016", 8 pgs.
"U.S. Appl. No. 15/211,812, Response filed Apr. 19, 2017 to Non Final Office Action mailed Jan. 27, 2017", 9 pgs.
"U.S. Appl. No. 15/267,793, Non Final Office Action mailed Jun. 14, 2018", 12 pgs.
"U.S. Appl. No. 15/267,793, Notice of Allowability mailed Jan. 17, 2019", 2 pgs.
"U.S. Appl. No. 15/267,793, Notice of Allowance mailed Dec. 21, 2018", 5 pgs.
"U.S. Appl. No. 15/267,793, Response Filed Apr. 11, 2018 to Restriction Requirement Mailed Feb. 16, 2018", 8 pgs.
"U.S. Appl. No. 15/267,793, Response filed Aug. 22, 2018 Non Final Office Action mailed Jun. 14, 2018", 16 pgs.
"U.S. Appl. No. 15/267,793, Restriction Requirement mailed Feb. 16, 2018", 7 pgs.

"U.S. Appl. No. 15/424,328, Non Final Office Action mailed Jun. 23, 2017", 5 pgs.
"U.S. Appl. No. 15/424,328, Notice of Allowance mailed Oct. 16, 2017", 6 pgs.
"U.S. Appl. No. 15/424,328, Preliminary Amendment filed Feb. 28, 2017", 10 pgs.
"U.S. Appl. No. 15/424,328, Response filed Sep. 20, 2017 to Non Final Office Action mailed Jun. 23, 2017", 9 pgs.
"U.S. Appl. No. 15/435,620, Final Office Action mailed Dec. 15, 2017", 9 pgs.
"U.S. Appl. No. 15/435,620, Non Final Office Action mailed Jul. 26, 2017", 10 pgs.
"U.S. Appl. No. 15/435,620, Notice of Allowance mailed Mar. 13, 2018", 5 pgs.
"U.S. Appl. No. 15/435,620, Preliminary Amendment filed Mar. 20, 2017", 7 pgs.
"U.S. Appl. No. 15/435,620, Response filed Feb. 12, 2018 to Final Office Action mailed Dec. 15, 2017", 9 pgs.
"U.S. Appl. No. 15/435,620, Response filed Oct. 25, 2017 to Non Final Office Action mailed Jul. 26, 2017", 13 pgs.
"U.S. Appl. No. 15/616,561, Non Final Office Action mailed Aug. 9, 2018", 8 pgs.
"U.S. Appl. No. 15/616,561, Notice of Allowability mailed Feb. 12, 2019", 2 pgs.
"U.S. Appl. No. 15/616,561, Notice of Allowance mailed Dec. 10, 2018", 7 pgs.
"U.S. Appl. No. 15/616,561, Preliminary Amendment filed Jun. 8, 2017", 7 pgs.
"U.S. Appl. No. 15/616,561, Response filed Nov. 8, 2018 to Non Final Office Action mailed Aug. 9, 2018", 11 pgs.
"U.S. Appl. No. 15/703,678, Non Final Office Action mailed Apr. 8, 2019", 11 pgs.
"U.S. Appl. No. 15/703,678, Notice of Allowance mailed Sep. 17, 2019", 7 pgs.
"U.S. Appl. No. 15/703,678, Preliminary Amendment filed Sep. 28, 2017", 9 pgs.
"U.S. Appl. No. 15/703,678, Response Filed Jan. 3, 2019 to Restriction Requirement Mailed Nov. 5, 2018", 8 pgs.
"U.S. Appl. No. 15/703,678, Response filed Jul. 3, 2019 to Non-Final Office Action mailed Apr. 8, 2019", 20 pgs.
"U.S. Appl. No. 15/703,678, Restriction Requirement mailed Nov. 5, 2018", 6 pgs.
"U.S. Appl. No. 15/703,692, Corrected Notice of Allowability mailed Jul. 8, 2019", 2 pgs.
"U.S. Appl. No. 15/703,692, Non Final Office Action mailed Jan. 14, 2019", 11 pgs.
"U.S. Appl. No. 15/703,692, Notice of Allowance mailed May 7, 2019", 5 pgs.
"U.S. Appl. No. 15/703,692, Preliminary Amendment filed Sep. 28, 2017", 9 pgs.
"U.S. Appl. No. 15/703,692, Response filed Apr. 4, 2019 to Non Final Office Action mailed Jan. 14, 2019", 11 pgs.
"U.S. Appl. No. 15/703,698, Corrected Notice of Allowability mailed Dec. 18, 2018", 2 pgs.
"U.S. Appl. No. 15/703,698, Non Final Office Action mailed Apr. 6, 2018", 7 pgs.
"U.S. Appl. No. 15/703,698, Notice of Allowance mailed Sep. 12, 2018", 5 pgs.
"U.S. Appl. No. 15/703,698, Preliminary Amendment filed Sep. 28, 2017", 8 pgs.
"U.S. Appl. No. 15/703,698, Response filed Jul. 6, 2018 to Non Final Office Action mailed Apr. 6, 2018", 10 pgs.
"U.S. Appl. No. 15/703,713, Non Final Office Action mailed Mar. 27, 2018", 29 pgs.
"U.S. Appl. No. 15/703,713, Notice of Allowance mailed Sep. 25, 2018", 11 pgs.
"U.S. Appl. No. 15/703,713, Response Filed Jun. 15, 2018 to Non-Final Office Action Mailed Mar. 27, 2018", 16 pgs.
"U.S. Appl. No. 15/703,713, Preliminary Amendment filed Sep. 28, 2017", 7 pgs.
"U.S. Appl. No. 15/720,866, Final Office Action mailed Feb. 28, 2020", 10 pgs.

(56)  References Cited

OTHER PUBLICATIONS

"U.S. Appl. No. 15/720,866, Non Final Office Action mailed Sep. 9, 2019", 12 pgs.

"U.S. Appl. No. 15/720,866, Notice of Allowance mailed Sep. 23, 2020", 7 pgs.

"U.S. Appl. No. 15/720,866, PTO Response to Rule 312 Communication mailed Nov. 20, 2020", 2 pgs.

"U.S. Appl. No. 15/720,866, Response filed Jan. 9, 2020 to Non Final Office Action mailed Sep. 9, 2019", 11 pgs.

"U.S. Appl. No. 15/720,866, Response filed May 27, 2020 to Final Office Action mailed Feb. 28, 2020", 13 pgs.

"U.S. Appl. No. 15/720,866, Response filed Jul. 10, 2019 to Restriction Requirement mailed May 14, 2019", 10 pgs.

"U.S. Appl. No. 15/720,866, Response filed Nov. 13, 2017 to Non Final Office Action mailed Sep. 14, 2017", 10 pgs.

"U.S. Appl. No. 15/720,866, Restriction Requirement mailed May 14, 2019", 7 pgs.

"U.S. Appl. No. 15/720,866, Preliminary Amendment filed Nov. 13, 2017", 9 pgs.

"U.S. Appl. No. 15/827,654, Examiner Interview Summary mailed Apr. 26, 2019", 4 pgs.

"U.S. Appl. No. 15/827,654, Final Office Action mailed Feb. 19, 2019", 19 pgs.

"U.S. Appl. No. 15/827,654, Non Final Office Action mailed Sep. 7, 2018", 21 pgs.

"U.S. Appl. No. 15/827,654, Notice of Allowance mailed Jul. 8, 2019", 8 pgs.

"U.S. Appl. No. 15/827,654, Preliminary Amendment filed Dec. 22, 2017", 11 pgs.

"U.S. Appl. No. 15/827,654, Response Filed May 20, 2019 to Final Office Action Mailed Feb. 19, 2019", 17 pgs.

"U.S. Appl. No. 15/827,654, Response filed Jun. 6, 2018 to Restriction Requirement mailed Apr. 6, 2018", 11 pgs.

"U.S. Appl. No. 15/827,654, Response filed to Non Final Office Action mailed Sep. 7, 2018", 24 pgs.

"U.S. Appl. No. 15/827,654, Restriction Requirement mailed Apr. 6, 2018", 6 pgs.

"U.S. Appl. No. 15/890,735, Notice of Allowance mailed Oct. 29, 2019", 11 pgs.

"U.S. Appl. No. 15/915,886, Non Final Office Action mailed Aug. 2, 2019", 9 pgs.

"U.S. Appl. No. 15/915,886, Notice of Allowance mailed Jan. 16, 2020", 9 pgs.

"U.S. Appl. No. 15/915,886, PTO Response to Rule 312 Communication mailed May 8, 2020", 2 pgs.

"U.S. Appl. No. 15/915,886, Response Filed Nov. 4, 2019 to Non-Final Office Action Mailed Aug. 2, 2019", 8 pgs.

"U.S. Appl. No. 15/971,743, Notice of Allowance mailed Aug. 6, 2019", 8 pgs.

"U.S. Appl. No. 16/179,201, Advisory Action mailed Jun. 25, 2021", 3 pgs.

"U.S. Appl. No. 16/179,201, Examiner Interview Summary mailed Feb. 8, 2021", 3 pgs.

"U.S. Appl. No. 16/179,201, Examiner Interview Summary mailed Nov. 9, 2021", 4 pgs.

"U.S. Appl. No. 16/179,201, Examiner Interview Summary mailed Nov. 17, 2021", 3 pgs.

"U.S. Appl. No. 16/179,201, Final Office Action mailed Apr. 20, 2021", 11 pgs.

"U.S. Appl. No. 16/179,201, Non Final Office Action mailed Sep. 22, 2021", 11 pgs.

"U.S. Appl. No. 16/179,201, Non Final Office Action mailed Nov. 2, 2020", 15 pgs.

"U.S. Appl. No. 16/179,201, Notice of Allowance mailed Apr. 21, 2022", 9 pgs.

"U.S. Appl. No. 16/179,201, Response filed Jan. 28, 2021 to Non Final Office Action mailed Nov. 2, 2020", 16 pgs.

"U.S. Appl. No. 16/179,201, Response filed Jun. 18, 2021 to Final Office Action mailed Apr. 20, 2021", 16 pgs.

"U.S. Appl. No. 16/179,201, Response filed Oct. 5, 2020 to Restriction Requirement mailed Aug. 7, 2020", 9 pgs.

"U.S. Appl. No. 16/179,201, Response filed Dec. 3, 2021 to Non Final Office Action mailed Sep. 22, 2021", 11 pgs.

"U.S. Appl. No. 16/179,201, Restriction Requirement mailed Aug. 7, 2020", 10 pgs.

"U.S. Appl. No. 16/179,201, Supplemental Response filed Feb. 19, 2021 to Non-Final Office Action mailed Nov. 2, 2020", 17 pgs.

"U.S. Appl. No. 16/352,287, Final Office Action mailed May 25, 2021", 8 pgs.

"U.S. Appl. No. 16/352,287, Non Final Office Action mailed Dec. 10, 2020", 12 pgs.

"U.S. Appl. No. 16/352,287, Notice of Allowance mailed Jun. 30, 2021", 7 pgs.

"U.S. Appl. No. 16/352,287, Response filed Feb. 22, 2021 to Non Final Office Action mailed Dec. 10, 2020", 14 pgs.

"U.S. Appl. No. 16/352,287, Response filed Jun. 18, 2021 to Final Office Action mailed May 25, 2021", 8 pgs.

"U.S. Appl. No. 16/352,287, Response filed Oct. 12, 2020 to Restriction Requirement mailed Aug. 17, 2020", 8 pgs.

"U.S. Appl. No. 16/352,287, Restriction Requirement mailed Aug. 17, 2020", 6 pgs.

"U.S. Appl. No. 16/389,381, Non Final Office Action mailed Mar. 30, 2020", 9 pgs.

"U.S. Appl. No. 16/389,381, Notice of Allowance mailed Jul. 16, 2020", 5 pgs.

"U.S. Appl. No. 16/389,381, Response filed Jun. 19, 2020 to Non Final Office Action mailed Mar. 30, 2020", 9 pgs.

"U.S. Appl. No. 16/530,423, Final Office Action mailed Nov. 4, 2021", 11 pgs.

"U.S. Appl. No. 16/530,423, Non Final Office Action mailed Mar. 3, 2022", 14 pgs.

"U.S. Appl. No. 16/530,423, Non Final Office Action mailed May 17, 2021", 10 pgs.

"U.S. Appl. No. 16/530,423, Notice of Allowance mailed Jun. 14, 2022", 6 pgs.

"U.S. Appl. No. 16/530,423, Preliminary Amendment filed Aug. 28, 2019", 7 pgs.

"U.S. Appl. No. 16/530,423, Response filed Feb. 4, 2022 to Final Office Action mailed Nov. 4, 2021", 15 pgs.

"U.S. Appl. No. 16/530,423, Response filed Jun. 1, 2022 to Non Final Office Action mailed Mar. 3, 2022", 14 pgs.

"U.S. Appl. No. 16/530,423, Response filed Aug. 11, 2021 to Non Final Office Action mailed May 17, 2021", 15 pgs.

"U.S. Appl. No. 16/596,194, Amendment Under 1.312 Filed Dec. 7, 2021", 9 pgs.

"U.S. Appl. No. 16/596,194, Final Office Action mailed May 20, 2021", 21 pgs.

"U.S. Appl. No. 16/596,194, Non Final Office Action mailed Jan. 22, 2021", 19 pgs.

"U.S. Appl. No. 16/596,194, Notice of Allowance mailed Sep. 9, 2021", 10 pgs.

"U.S. Appl. No. 16/596,194, Preliminary Amendment Filed Nov. 14, 2019", 8 pgs.

"U.S. Appl. No. 16/596,194, PTO Response to Rule 312 Communication mailed Dec. 13, 2021", 2 pgs.

"U.S. Appl. No. 16/596,194, Response filed Apr. 12, 2021 to Non Final Office Action mailed Jan. 22, 2021", 15 pgs.

"U.S. Appl. No. 16/596,194, Response filed Aug. 18, 2021 to Final Office Action mailed May 20, 2021", 15 pgs.

"U.S. Appl. No. 16/675,938, Non Final Office Action mailed Sep. 16, 2021", 5 pgs.

"U.S. Appl. No. 16/675,938, Notice of Allowance mailed Jan. 12, 2022", 8 pgs.

"U.S. Appl. No. 16/675,938, Preliminary Amendment filed Jan. 22, 2020", 7 pgs.

"U.S. Appl. No. 16/675,938, Response filed Dec. 3, 2021 to Non Final Office Action mailed Sep. 16, 2021", 8 pgs.

"U.S. Appl. No. 16/675,938, Supplemental Notice of Allowability mailed Feb. 1, 2022", 2 pgs.

"U.S. Appl. No. 16/715,092, Final Office Action mailed Mar. 16, 2022", 8 pgs.

(56)                    References Cited

OTHER PUBLICATIONS

"U.S. Appl. No. 16/715,092, Non Final Office Action mailed Sep. 22, 2021", 8 pgs.
"U.S. Appl. No. 16/715,092, Preliminary Amendment filed Mar. 19, 2020", 10 pgs.
"U.S. Appl. No. 16/715,092, Response filed Aug. 9, 2021 to Restriction Requirement mailed Jun. 25, 2021", 7 pgs.
"U.S. Appl. No. 16/715,092, Response filed Dec. 10, 2021 to Non Final Office Action mailed Sep. 22, 2021", 14 pgs.
"U.S. Appl. No. 16/715,092, Restriction Requirement mailed Jun. 25, 2021", 6 pgs.
"U.S. Appl. No. 16/743,746, Notice of Allowance mailed Jan. 13, 2022", 14 pgs.
"U.S. Appl. No. 16/743,746, Preliminary Amendment filed Mar. 19, 2020", 8 pgs.
"U.S. Appl. No. 16/743,746, Supplemental Notice of Allowability mailed Jan. 27, 2022", 2 pgs.
"U.S. Appl. No. 16/849,394, Non Final Office Action mailed Jun. 3, 2022", 9 pgs.
"U.S. Appl. No. 16/849,394, Preliminary Amendment filed Jun. 3, 2020", 7 pgs.
"U.S. Appl. No. 17/068,435, Preliminary Amendment filed Nov. 13, 2020", 7 pgs.
"U.S. Appl. No. 17/134,885, Preliminary Amendment filed Jan. 18, 2021", 10 pgs.
"U.S. Appl. No. 17/545,728, Preliminary Amendment filed Jan. 7, 2022", 10 pgs.
"U.S. Appl. No. 17/717,898, Preliminary Amendment filed Apr. 29, 2022", 7 pgs.
"Australian Application Serial No. 2011286306, First Examiner Report mailed Jun. 19, 2013", 4 pgs.
"Australian Application Serial No. 2011286306, Response filed Jun. 3, 2014 to First Examiner Report mailed Jun. 19, 2013", 16 pgs.
"Australian Application Serial No. 2011286307, First Examiner Report mailed Oct. 17, 2013", 2 pgs.
"Australian Application Serial No. 2011286307, Response filed May 21, 2014 to First Examiner Report mailed Oct. 17, 2013", 16 pgs.
"Australian Application Serial No. 2011286308, First Examiner Report mailed Jun. 21, 2013", 4 pgs.
"Australian Application Serial No. 2011286308, Response filed Jun. 6, 2014 First Examiner Report mailed Jun. 21, 2013", 19 pgs.
"Australian Application Serial No. 2011286309, First Examiner Report mailed Jun. 21, 2013", 3 pgs.
"Australian Application Serial No. 2011286309, Response filed Jun. 10, 2014 to First Examiner Report mailed Jun. 21, 2013", 4 pgs.
"Australian Application Serial No. 2011343440, First Examiner Report mailed Feb. 17, 2014", 3 pgs.
"Australian Application Serial No. 2011343440, Response filed Mar. 21, 2014 to Office Action mailed Feb. 17, 2014", 1 pg.
"Australian Application Serial No. 2012271243, Office Action mailed Apr. 1, 2015", 2 pgs.
"Australian Application Serial No. 2012271243, Response filed Apr. 8, 2015 to Office Action mailed Apr. 1, 2015", 4 pgs.
"Australian Application Serial No. 2012271243, Response filed Apr. 15, 2015 to Office Action mailed Apr. 13, 2015", 1 pg.
"Australian Application Serial No. 2012271243, Subsequent Examiners Report mailed Apr. 13, 2015", 2 pgs.
"Australian Application Serial No. 2012341026, First Examiner Report mailed Jul. 14, 2014", 2 pgs.
"Australian Application Serial No. 2012341026, Response filed Nov. 21, 2014 to First Examiner Report mailed Jul. 14, 2014", 1 pg.
"Australian Application Serial No. 2012341026, Statement of Proposed Amendment filed Jun. 18, 2014", 25 pgs.
"Australian Application Serial No. 2012368262, First Examiner Report mailed Nov. 2, 2016", 4 pgs.
"Australian Application Serial No. 2012368262, Response filed Jan. 17, 2017 to Office Action mailed Nov. 2, 2016", 21 pgs.
"Australian Application Serial No. 2012368262, Response filed May 15, 2017 to Subsequent Examiners Report mailed Mar. 16, 2017", 2 pgs.
"Australian Application Serial No. 2012368262, Subsequent Examiners Report mailed Mar. 16, 2017", 3 pgs.
"Australian Application Serial No. 2013238046, First Examiner Report mailed Nov. 26, 2015", 2 pgs.
"Australian Application Serial No. 2013238046, Response filed Feb. 2, 2016 to First Examiner Report mailed Nov. 26, 2015", 1 pg.
"Australian Application Serial No. 2013238054, First Examiner Report mailed Oct. 17, 2016", 4 pgs.
"Australian Application Serial No. 2013238054, Response filed Jan. 18, 2017 to First Examiner Report mailed Oct. 17, 2016", 9 pgs.
"Australian Application Serial No. 2014250709, First Examiner Report mailed Dec. 21, 2015", 3 pgs.
"Australian Application Serial No. 2014250709, Response filed May 4, 2016 to First Examiner Report mailed Dec. 21, 2015", 12 pgs.
"Australian Application Serial No. 2014250709, Subsequent Examiners Report mailed May 31, 2016", 6 pgs.
"Australian Application Serial No. 2014250710, First Examiner Report mailed Dec. 11, 2015", 7 pgs.
"Australian Application Serial No. 2014250710, Response filed Mar. 22, 2016 to First Examiner Report mailed Dec. 11, 2015", 18 pgs.
"Australian Application Serial No. 2014250710, Response filed May 4, 2016 to Subsequent Examiners Report mailed Mar. 23, 2016", 15 pgs.
"Australian Application Serial No. 2014250710, Subsequent Examiners Report mailed Mar. 23, 2016", 3 pgs.
"Australian Application Serial No. 2014250711, First Examiner Report mailed Feb. 12, 2016", 7 pgs.
"Australian Application Serial No. 2014250711, Response filed Apr. 27, 2016 to First Examiner Report mailed Feb. 12, 2016", 32 pgs.
"Australian Application Serial No. 2015201511, First Examination Report mailed Apr. 18, 2016", 2 pgs.
"Australian Application Serial No. 2015201511, Response filed Jun. 30, 2016 to First Examiner Report mailed Apr. 18, 2016", 12 pgs.
"Australian Application Serial No. 2015238820, First Examination Report mailed May 30, 2017", 3 pgs.
"Australian Application Serial No. 2015238820, Response filed Jul. 12, 2017 to First Examination Report mailed May 30, 2017", 12 pgs.
"Australian Application Serial No. 2016225911, First Examiners Report mailed Jun. 2, 2017", 3 pgs.
"Australian Application Serial No. 2016225911, Response filed Aug. 22, 2017 to First Examiners Report mailed Jun. 2, 2017", 18 pgs.
"Australian Application Serial No. 2017235987, First Examination Report mailed Nov. 1, 2018", 4 pgs.
"Australian Application Serial No. 2017251736, First Examiners Report mailed Oct. 31, 2017", 2 pgs.
"Australian Application Serial No. 2018266322, First Examination Report mailed Dec. 19, 2019", 2 pgs.
"Australian Application Serial No. 2020204019, First Examination Report mailed Jun. 18, 2021", 7 pgs.
"Australian Application Serial No. 2020204019, Response filed Jan. 11, 2022 to Subsequent Examiners Report mailed Nov. 16, 2021", 19 pgs.
"Australian Application Serial No. 2020204019, Response filed Aug. 19, 2021 to First Examination Report mailed Jun. 18, 2021", 3 pgs.
"Australian Application Serial No. 2020204019, Response filed Oct. 15, 2021 to Subsequent Examiners Report mailed Sep. 2, 2021", 22 pgs.
"Australian Application Serial No. 2020204019, Subsequent Examiners Report mailed Sep. 2, 2021", 4 pgs.
"Australian Application Serial No. 2020204019, Subsequent Examiners Report mailed Nov. 16, 2021", 3 pgs.
"Bi-Cruciate Stabilized Knee System", Design Rationale, Smith & Nephew Journal, (2006), 20 pgs.
"Brazil Application Serial No. BR1120130016698, Office Action mailed Aug. 27, 2019", (W/ English Translation), 8 pages.

(56)                    References Cited

OTHER PUBLICATIONS

"Brazil Application Serial No. BR1120130016698, Response filed Dec. 9, 2019 to Office Action mailed Aug. 27, 2019", w/ English Claims, 22 pgs.
"Brazil Application Serial No. BR1120130016736, Office Action mailed Aug. 27, 2019", (with English translation), 8 pages.
"Brazil Application Serial No. BR1120130016736, Response filed Dec. 9, 2019 to Office Action mailed Aug. 27, 2019", w/ English Claims, 25 pgs.
"Brazilian Application Serial No. BR1120130016736, Response filed Oct. 5, 2020 to Office Action mailed Jun. 10, 2020", (W/ English Translation of Claims), 91 pgs.
"Canadian Application Serial No. 2,806,321, Office Action mailed Jan. 15, 2018", 3 pgs.
"Canadian Application Serial No. 2,806,321, Response filed Jan. 22, 2018 to Office Action mailed Jan. 15, 2018", 7 pgs.
"Canadian Application Serial No. 2,806,321, Response filed Dec. 6, 2017 to Office Action mailed Jun. 15, 2017", 12 pgs.
"Canadian Application Serial No. 2,806,325, Office Action mailed Mar. 14, 2016", 4 pgs.
"Canadian Application Serial No. 2,806,325, Response filed Sep. 14, 2016 to Office Action mailed Mar. 14, 2016", 17 pgs.
"Canadian Application Serial No. 2,806,326, Examiner's Rule 30(2) Requisition mailed Sep. 20, 2018", 4 pgs.
"Canadian Application Serial No. 2,806,326, Office Action mailed Feb. 8, 2018", 4 pgs.
"Canadian Application Serial No. 2,806,326, Office Action mailed Jun. 19, 2017", 3 pgs.
"Canadian Application Serial No. 2,806,326, Response Filed Mar. 20, 2019 to Examiner's Rule 30(2) Requisition mailed Sep. 20, 2018", 4 pgs.
"Canadian Application Serial No. 2,806,326, Response filed Jul. 20, 2018 to Office Action mailed Feb. 8, 2018", 12 pgs.
"Canadian Application Serial No. 2,821,927, Office Action mailed Jan. 25, 2018", 6 pgs.
"Canadian Application Serial No. 2,821,927, Response filed Jul. 18, 2018 to Office Action mailed Jan. 25, 2018", 10 pgs.
"Canadian Application Serial No. 2,821,927, Voluntary Amendment mailed Jun. 14, 2013", 7 pgs.
"Canadian Application Serial No. 2,824,527, Office Action mailed Mar. 17, 2014", 2 pgs.
"Canadian Application Serial No. 2,824,527, Response filed Sep. 17, 2014 to Office Action mailed Mar. 17, 2014", 14 pgs.
"Canadian Application Serial No. 2,856,070, Preliminary Amendment filed May 25, 2015", 27 pgs.
"Canadian Application Serial No. 2,856,571 Response filed Jan. 22, 2015 to Office Action mailed Jul. 22, 2014", 24 pgs.
"Canadian Application Serial No. 2,856,571, Office Action mailed Jul. 22, 2014", 2 pgs.
"Canadian Application Serial No. 2,863,375, Office Action mailed Apr. 20, 2018", 3 pgs.
"Canadian Application Serial No. 2,863,375, Response filed Oct. 22, 2018 Office Action mailed Apr. 20, 2018", 12 pgs.
"Canadian Application Serial No. 2,868,825, Office Action mailed Dec. 27, 2018", 3 pgs.
"Canadian Application Serial No. 2,956,119, Examiner's Rule 30(2) Requisition mailed Sep. 27, 2018", 4 pgs.
"Canadian Application Serial No. 2,956,119, Office Action mailed Jan. 22, 2018", 3 pgs.
"Canadian Application Serial No. 2,956,119, Response Filed Mar. 27, 2019 to Examiner's Rule 30(2) Requisition mailed Sep. 27, 2018", 7 pgs.
"Canadian Application Serial No. 2,989,184, Office Action mailed Oct. 1, 2018", 4 pgs.
"Canadian Application Serial No. 2,989,184, Response filed Apr. 1, 2019 to Office Action mailed Oct. 1, 2018", 10 pgs.
"Canadian Application Serial No. 3,063,415, Office Action mailed Jul. 13, 2020", 3 pgs.
"Canadian Application Serial No. 3,063,415, Response filed Nov. 12, 2020 to Office Action mailed Jul. 13, 2020", 15 pgs.
"Canadian Application Serial No. 2,806,321, Office Action mailed Jun. 15, 2017", 3 pgs.
"Chinese Application Serial No. 201180045673.3, Office Action mailed Feb. 14, 2016", (W/ English Translation), 17 pgs.
"Chinese Application Serial No. 201180045673.3, Office Action mailed Mar. 29, 2015", (W/ English Translation), 6 pgs.
"Chinese Application Serial No. 201180045673.3, Office Action mailed Aug. 12, 2015", (W/ English Translation), 7 pgs.
"Chinese Application Serial No. 201180045673.3, Response filed Jun. 19, 2015 to Office Action mailed Mar. 29, 2015", (W/ English translation of claims), 11 pgs.
"Chinese Application Serial No. 201180045673.3, Response filed Oct. 27, 2015 to Office Action mailed Aug. 12, 2015", (W/ English translation of claims), 9 pgs.
"Chinese Application Serial No. 201180045681.8, Office Action mailed Jan. 22, 2015", (W/ English Translation), 11 pgs.
"Chinese Application Serial No. 201180045681.8, Response filed May 14, 2015 to Office Action mailed Jan. 22, 2015", W/ English Claims, 17 pgs.
"Chinese Application Serial No. 201180045683.7, Office Action mailed Mar. 9, 2015", (W/ English Translation), 6 pgs.
"Chinese Application Serial No. 201180045683.7, Response filed Jul. 14, 2015 to Office Action mailed Mar. 9, 2015", (W/ English translation of claims), 30 pgs.
"Chinese Application Serial No. 201180045689.4, Office Action mailed Jan. 5, 2015", (W/ English Translation), 4 pgs.
"Chinese Application Serial No. 201180045689.4, Office Action mailed Feb. 2, 2016", w/English Translation, 11 pgs.
"Chinese Application Serial No. 201180045689.4, Office Action mailed Aug. 5, 2015", (W/ English Translation), 11 pgs.
"Chinese Application Serial No. 201180045689.4, Response filed May 1, 2015 to Office Action mailed Jan. 5, 2015", W/ English Claims, 13 pgs.
"Chinese Application Serial No. 201180067430.X, Office Action mailed Aug. 28, 2014", (W/ English Translation), 8 pgs.
"Chinese Application Serial No. 201180067430.X, Response filed Jan. 4, 2015 to Office Action mailed Sep. 26, 2014", (W/ English Translation), 14 pgs.
"Chinese Application Serial No. 201180067757.7, Office Action mailed Mar. 2, 2015", (W/ English Translation), 18 pgs.
"Chinese Application Serial No. 201180067757.7, Office Action mailed Jun. 1, 2016", (W/ English Translation), 10 pgs.
"Chinese Application Serial No. 201180067757.7, Office Action mailed Nov. 16, 2015", (W/ English Translation), 17 pgs.
"Chinese Application Serial No. 201180067757.7, Response filed Jan. 27, 2016 to Office Action mailed Nov. 16, 2015", (W/ English Translation of Claims), 12 pgs.
"Chinese Application Serial No. 201180067757.7, Response filed Jul. 10, 2015 to Office Action mailed Mar. 2, 2015", (W/ English Translation), 13 pgs.
"Chinese Application Serial No. 201180067757.7, Response filed Aug. 11, 2016 to Office Action mailed Jun. 1, 2016", (W/ English Translation Of Claims), 9 pgs.
"Chinese Application Serial No. 201180067757.7, Voluntary Amendment mailed Feb. 14, 2014", (W/ English Translation of Claims), 8 pgs.
"Chinese Application Serial No. 201280067473.2, Office Action mailed Feb. 1, 2016", (W/ English Translation), 4 pgs.
"Chinese Application Serial No. 201280067473.2, Office Action mailed May 20, 2015", (W/ English Translation), 15 pgs.
"Chinese Application Serial No. 201280067473.2, Office Action mailed Nov. 20, 2015", W/ English Translation of Claims, 7 pgs.
"Chinese Application Serial No. 201280067473.2, Response filed Apr. 7, 2016 to Office Action mailed Feb. 1, 2016", (W/ English translation of claims), 11 pgs.
"Chinese Application Serial No. 201280067473.2, Response filed Sep. 7, 2015 to Office Action mailed May 20, 2015", (W/ English translation of claims), 12 pgs.
"Chinese Application Serial No. 201280067473.2, Response filed Dec. 4, 2015 to Office Action mailed Nov. 20, 2015", w/English Claims, 11 pgs.
"Chinese Application Serial No. 201280067481.7, Office Action mailed Sep. 30, 2015", (W/ English Translation), 7 pgs.

(56)     References Cited

OTHER PUBLICATIONS

"Chinese Application Serial No. 201280071940.9, Office Action mailed Jul. 22, 2015", (W/ English Translation), 13 pgs.
"Chinese Application Serial No. 201280071940.9, Preliminary Amendment filed Mar. 23, 2015", W/ English Claims, 11 pgs.
"Chinese Application Serial No. 201380028572.4, Office Action mailed Aug. 13, 2015", (W/ English Translation), 16 pgs.
"Chinese Application Serial No. 201380028683.5, Office Action mailed Jun. 27, 2016", (W/ English Translation), 8 pgs.
"Chinese Application Serial No. 201380028683.5, Office Action mailed Nov. 4, 2015", (W/ English Translation), 16 pgs.
"Chinese Application Serial No. 201380028683.5, Office Action mailed Dec. 30, 2016", (W/ English Translation), 4 pgs.
"Chinese Application Serial No. 201380028683.5, Response filed Feb. 8, 2017 to Office Action mailed Dec. 30, 2016", (W/ English Translation), 13 pgs.
"Chinese Application Serial No. 201380028683.5, Response filed Mar. 18, 2016 to Office Action malled Nov. 4, 2015", (W/ English Translation of Claims), 11 pgs.
"Chinese Application Serial No. 201380028683.5, Response filed Sep. 6, 2016 to Office Action mailed Jun. 27, 2016", (W/ English Translation of Claims), 11 pgs.
"Chinese Application Serial No. 201510394094.X, Office Action mailed May 24, 2017", (W/ English Translation), 11 pgs.
"Chinese Application Serial No. 201510394094.X, Office Action mailed Aug. 30, 2016", (W/ English Translation), 14 pgs.
"Chinese Application Serial No. 201510394094.X, Office Action mailed Nov. 3, 2017", (W/ English Translation), 10 pgs.
"Chinese Application Serial No. 201510394094.X, Response filed Jan. 16, 2017 to Office Action mailed Aug. 30, 2016", (W/ English Translation of Claims), 11 pgs.
"Chinese Application Serial No. 201510394094.X, Response filed Jan. 18, 2018 to Office Action mailed Nov. 3, 2017", (W/ English Claims), 10 pgs.
"Chinese Application Serial No. 201510394094.X, Response filed Jul. 10, 2017 to Office Action mailed May 24, 2017", (W/ English Translation), 10 pgs.
"Chinese Application Serial No. 201510640436.1, Office Action mailed Sep. 28, 2016", (W/ English Translation), 13 pgs.
"Chinese Application Serial No. 201510640436.1, Response filed Feb. 16, 2017 to Office Action mailed Sep. 28, 2016", (W/ English Translation), 18 pgs.
"Chinese Application Serial No. 201610634595.5, Office Action mailed Apr. 20, 2018", (W/ English Translation), 8 pgs.
"Chinese Application Serial No. 201610634595.5, Office Action mailed Jun. 21, 2017", w/English Translation, 9 pgs.
"Chinese Application Serial No. 201610634595.5, Response filed Jun. 4, 2018 to Office Action mailed Apr. 20, 2018", (W/ English Translation of Claims), 8 pgs.
"Chinese Application Serial No. 201610634595.5, Response filed Nov. 3, 2017 to Office Action mailed Jun. 21, 2017", w/English Claims, 8 pgs.
"Chinese Application Serial No. 201610685172.6, Office Action mailed Apr. 10, 2017", (W/ English Translation), 11 pgs.
"Chinese Application Serial No. 201610685172.6, Office Action mailed Sep. 28, 2017", (W/ English Translation), 9 pgs.
"Chinese Application Serial No. 201610685172.6, Response filed Dec. 13, 2017 to Office Action mailed Sep. 28, 2017", (W/ English Claims), 13 pgs.
"Chinese Application Serial No. 201680061268.3, Office Action mailed Apr. 24, 2019", (W/ English Translation), 11 pgs.
"Chinese Application Serial No. 201680061268.3, Response filed Aug. 21, 2019 to Office Action mailed Apr. 24, 2019", (W/ English Claims), 8 pgs.
"Chinese Application Serial No. 201880016775.4, Decision of Rejection mailed Jul. 12, 2021", (W/ English Translation), 13 pgs.
"Chinese Application Serial No. 201880016775.4, Office Action mailed Jan. 22, 2021", with English translation, 15 pages.
"Chinese Application Serial No. 201880031319.7, Office Action mailed May 15, 2020", (W/ English Translation), 12 pgs.

"Chinese Application Serial No. 201880031319.7, Office Action mailed Nov. 18, 2020", (W/ English Translation), 9 pgs.
"Chinese Application Serial No. 201880031319.7, Response filed Jan. 18, 2021 to Office Action mailed Nov. 18, 2020", (W/ English Claims), 16 pgs.
"Chinese Application Serial No. 201880031319.7, Response filed Jul. 22, 2020 to Office Action mailed May 15, 2020", (W/ English Claims), 10 pgs.
"Complete Knee Solution Surgical Technique for the CR-Flex Fixed Bearing Knee", Zimmer Nexgen, (2003), 22 pgs.
"European Application Serial No. 11738918.9, Examination Notification Art. 94(3) mailed Oct. 23, 2014", 5 pgs.
"European Application Serial No. 11738918.9, Preliminary Amendment mailed Sep. 24, 2013", 11 pgs.
"European Application Serial No. 11738918.9, Response filed Mar. 2, 2015 to Examination Notification Art. 94(3) mailed Oct. 23, 2014", 14 pgs.
"European Application Serial No. 11738919.7, Examination Notification Art. 94(3) mailed Jul. 7, 2014", 4 pgs.
"European Application Serial No. 11738919.7, Preliminary Amendment filed Nov. 4, 2013", 25 pgs.
"European Application Serial No. 11738919.7, Response filed Nov. 13, 2014 to Examination Notification Art. 94(3) mailed Jul. 7, 2014", 14 pgs.
"European Application Serial No. 11738920.5, Communication Pursuant to Article 94(3) EPC mailed Mar. 15, 2016", 4 pgs.
"European Application Serial No. 11738920.5, Preliminary Amendment Sep. 24, 2013", 9 pgs.
"European Application Serial No. 11738920.5, Response filed Jul. 25, 2016 to Communication Pursuant to Article 94(3) EPC mailed Mar. 15, 2016", 6 pgs.
"European Application Serial No. 11738920.5, Response filed Sep. 24, 2013 to Communication pursuant to Rules 161(2) and 162 EPC mailed Mar. 15, 2013", 22 pgs.
"European Application Serial No. 11758060.5, Communication Pursuant to Article 94(3) EPC mailed Jul. 12, 2016", 3 pgs.
"European Application Serial No. 11758060.5, Communication Pursuant to Article 94(3) EPC mailed Dec. 11, 2015", 4 pgs.
"European Application Serial No. 11758060.5, Preliminary Amendment filed Nov. 4, 2013", 15 pgs.
"European Application Serial No. 11758060.5, Response filed Apr. 21, 2016 to Communication Pursuant to Article 94(3) EPC mailed Dec. 11, 2015", 16 pgs.
"European Application Serial No. 11758060.5, Response filed Nov. 15, 2016 to Communication Pursuant to Article 94(3) EPC mailed Jul. 12, 2016", 23 pgs.
"European Application Serial No. 11802835.6, Communication Pursuant to Article 94(3) EPC mailed Dec. 11, 2017", 4 pgs.
"European Application Serial No. 11802835.6, Response filed Apr. 23, 2018 to Office Action mailed Dec. 11, 2017", 16 pgs.
"European Application Serial No. 11808493.8, Communication Pursuant to Article 94(3) EPC mailed Dec. 7, 2015", 4 pgs.
"European Application Serial No. 11808493.8, Examination Notification Art. 94(3) mailed Feb. 20, 2015", 6 pgs.
"European Application Serial No. 11808493.8, Response filed Feb. 26, 2014 to Communication pursuant to Rules 161(1) and 162 EPC mailed Aug. 16, 2013", 14 pgs.
"European Application Serial No. 11808493.8, Response filed Apr. 18, 2016 to Communication Pursuant to Article 94(3) EPC mailed Dec. 7, 2015", 15 pgs.
"European Application Serial No. 11808493.8, Response filed Jul. 2, 2015 to Examination Notification Art. 94(3) mailed Feb. 20, 2015", 13 pgs.
"European Application Serial No. 11815029.1, Communication Pursuant to Article 94(3) EPC mailed Sep. 29, 2016", 4 pgs.
"European Application Serial No. 11815029.1, Extended European Search Report mailed Dec. 10, 2013", 8 pgs.
"European Application Serial No. 11815029.1, Response filed Apr. 10, 2017 to Communication Pursuant to Article 94(3) EPC mailed Sep. 29, 2016", 22 pgs.
"European Application Serial No. 11815029.1, Response filed Jul. 21, 2014 Extended European Search Report mailed Dec. 10, 2013", 15 pgs.

(56)          References Cited

OTHER PUBLICATIONS

"European Application Serial No. 12718882.9, Communication Pursuant to Article 94(3) EPC mailed Dec. 1, 2015", 11 pgs.
"European Application Serial No. 12718882.9, Response filed Feb. 10, 2015 to Communication Pursuant to Rules 161(1) and 162 EPC mailed Jul. 31, 2014", 11 pgs.
"European Application Serial No. 12718882.9, Response filed Apr. 11, 2016 to Communication Pursuant to Article 94(3) EPC mailed Dec. 1, 2015", 12 pgs.
"European Application Serial No. 12718883.7, Communication Pursuant to Article 94(3) EPC mailed Dec. 2, 2015", 4 pgs.
"European Application Serial No. 12718883.7, Communication Pursuant to Rules 161(1) and 162 EPC mailed Jul. 31, 2014", 2 pgs.
"European Application Serial No. 12718883.7, Intention to Grant mailed May 20, 2016", 5 pgs.
"European Application Serial No. 12718883.7, Response filed Feb. 10, 2015 to Communication Pursuant to Rules 161(1) and 162 EPC mailed Jul. 31, 2014", 16 pgs.
"European Application Serial No. 12718883.7, Response filed Apr. 12, 2016 to Communication Pursuant to Article 94(3) EPC mailed Dec. 2, 2015", 30 pgs.
"European Application Serial No. 12719236.7 Response filed Feb. 9, 2015 to Communication Pursuant to Rules 161(1) and 162 EPC mailed Jul. 30, 2014", 10 pgs.
"European Application Serial No. 12719236.7, Decision to Grant mailed Feb. 18, 2016", 3 pgs.
"European Application Serial No. 12719236.7, Office Action mailed Aug. 27, 2015", 7 pgs.
"European Application Serial No. 12720352.9 Response filed Feb. 9, 2015 to Communication Pursuant to Rules 161(1) and 162 EPC mailed Jul. 30, 2014", 10 pgs.
"European Application Serial No. 12756058.9, Communication Pursuant to Article 94(3) EPC mailed Feb. 18, 2019", 4 pgs.
"European Application Serial No. 12756058.9, Office Action mailed Jan. 17, 2017", 5 Pgs.
"European Application Serial No. 12756058.9, Preliminary Amendment filed Apr. 20, 2015", 12 pgs.
"European Application Serial No. 12756058.9, Response filed May 26, 2017 to Office Action mailed Jan. 17, 2017", 16 pgs.
"European Application Serial No. 12756058.9, Response filed Jun. 28, 2019 to Communication Pursuant to Article 94(3) EPC mailed Feb. 18, 2019", 21 pgs.
"European Application Serial No. 12756869.9 Response filed Feb. 10, 2015 to Communication Pursuant to Rule 161(1) and 162 EPC mailed Jul. 31, 2014", 14 pgs.
"European Application Serial No. 12756869.9, Examination Notification Art. 94(3) mailed Jul. 2, 2015", 4 pgs.
"European Application Serial No. 12756869.9, Response filed Nov. 12, 1205 to Examination Notification Art. 94(3) mailed Jul. 2, 2015", 28 pgs.
"European Application Serial No. 13716636.9, Communication Pursuant to Article 94(3) EPC mailed Nov. 16, 2015", 4 pgs.
"European Application Serial No. 13716636.9, Communication Pursuant to Article 94(3) EPC mailed Nov. 17, 2016", 4 pgs.
"European Application Serial No. 13716636.9, Communication Pursuant to Article 94(3) EPC mailed Jun. 6, 2016", 5 pgs.
"European Application Serial No. 13716636.9, Communication pursuant to Rules 161(1) and 162 EPC mailed Dec. 12, 2014", 2 pgs.
"European Application Serial No. 13716636.9, Response filed Mar. 24, 2016 to Communication Pursuant to Article 94(3) EPC mailed Nov. 16, 2015", 18 pgs.
"European Application Serial No. 13716636.9, Response filed Mar. 27, 2017 to Communication Pursuant to Article 94(3) EPC mailed Nov. 17, 2016", 15 pgs.
"European Application Serial No. 13716636.9, Response filed Jun. 22, 2015 to Communication pursuant to Rules 161(1) and 162 EPC mailed Dec. 12, 2014", 10 pgs.

"European Application Serial No. 13716636.9, Response filed Oct. 17, 2016 to Communication Pursuant to Article 94(3) EPC mailed Jun. 6, 2016", 5 pgs.
"European Application Serial No. 14190180.1, Extended European Search Report mailed Sep. 24, 2015", 8 pgs.
"European Application Serial No. 15160934.4, Communication Pursuant to Article 94(3) EPC mailed Apr. 26, 2018", 5 pgs.
"European Application Serial No. 15160934.4, Extended European Search Report mailed Jun. 1, 2016", 8 pgs.
"European Application Serial No. 15160934.4, Response filed Aug. 30, 2018 to Communication Pursuant to Article 94(3) EPC mailed Apr. 26, 2018", 63 pgs.
"European Application Serial No. 15160934.4, Response filed Dec. 21, 2016 to Extended European Search Report mailed Jun. 1, 2016", 5 pgs.
"European Application Serial No. 15174394.5, Extended European Search Report mailed Mar. 21, 2016", 8 pgs.
"European Application Serial No. 15174394.5, Response filed Nov. 18, 2016 to Extended European Search Report mailed Mar. 21, 2016", 12 pgs.
"European Application Serial No. 15191781.2, Communication Pursuant to Article 94(3) EPC mailed Jan. 8, 2018", 4 pgs.
"European Application Serial No. 15191781.2, Extended European Search Report mailed Mar. 1, 2017", 8 pgs.
"European Application Serial No. 15191781.2, Response filed May 17, 2018 to Communication Pursuant to Article 94(3) EPC mailed Jan. 8, 2018", 58 pgs.
"European Application Serial No. 15191781.2, Response filed Sep. 28, 2017 to Extended European Search Report mailed Mar. 1, 2017", 14pgs.
"European Application Serial No. 16156228.5, Extended European Search Report mailed May 11, 2017", 5 pgs.
"European Application Serial No. 16183635.8, Extended European Search Report mailed Jun. 30, 2017", 9 pgs.
"European Application Serial No. 16183635.8, Response filed Mar. 27, 2018 to Extended European Search Report mailed Jun. 30, 2017", 8 pgs.
"European Application Serial No. 16189084.3, Communication Pursuant to Article 94(3) EPC mailed Jul. 1, 2021", 6 pgs.
"European Application Serial No. 16189084.3, Extended European Search Report mailed Oct. 9, 2017", 9 pgs.
"European Application Serial No. 16189084.3, Response filed May 10, 2018 to Extended European Search Report mailed Oct. 9, 2017", 20 pgs.
"European Application Serial No. 16189084.3, Response filed Nov. 8, 2021 to Communication Pursuant to Article 94(3) EPC mailed Jul. 1, 2021", 61 pgs.
"European Application Serial No. 16770657.1, Communication Pursuant to Article 94(3) EPC mailed May 20, 2019", 3 pgs.
"European Application Serial No. 16770657.1, Response filed Sep. 30, 2019 to Communication Pursuant to Article 94(3) EPC mailed May 20, 2019", 26 pgs.
"European Application Serial No. 16770657.1, Response filed Nov. 26, 2018 to Office Action mailed May 14, 2018", 17 pgs.
"European Application Serial No. 17157909.7, Extended European Search Report mailed Jul. 17, 2018", 7 pgs.
"European Application Serial No. 17157909.7, Response Filed Feb. 15, 2019 to Extended European Search Report mailed Jul. 17, 2018", 37 pgs.
"European Application Serial No. 17163432.2, Extended European Search Report mailed May 14, 2018", 6 pgs.
"European Application Serial No. 17163440.5, Extended European Search Report mailed Jan. 3, 2019", 16 pgs.
"European Application Serial No. 17163440.5, Partial European Search Report mailed Jul. 23, 2018", 15 pgs.
"European Application Serial No. 17163440.5, Response filed Jul. 22, 2019 to Extended European Search Report mailed Jan. 3, 2019", 14 pgs.
"European Application Serial No. 17168095.2, Extended European Search Report mailed Jun. 8, 2018", 8 pgs.
"European Application Serial No. 17168095.2, Response Filed Jan. 17, 2019 Extended (European Search Report mailed Jun. 8, 2018", 29 pgs.

(56)                    References Cited

OTHER PUBLICATIONS

"European Application Serial No. 17168308.9, Extended European Search Report mailed Jun. 13, 2018" 8 pgs.
"European Application Serial No. 17168308.9, Response Filed Jan. 17, 2019 to Extended European Search Report mailed Jun. 13, 2018", 24 pgs.
"European Application Serial No. 18206326.3, Extended European Search Report mailed Apr. 15, 2019", 10 pgs.
"European Application Serial No. 18206326.3, Response filed Nov. 22, 2019 to Extended European Search Report mailed Apr. 15, 2019", 15 pgs.
"European Application Serial No. 18711801.3, Response to Communication pursuant to Rules 161(1) and 162 EPC filed May 7, 2020", 14 pgs.
"European Application Serial No. 18726670.5, Response to Communication pursuant to Rules 161(1) and 162 EPC filed Jul. 20, 2020", 9 pgs.
"European Application Serial No. 19171990.5, Extended European Search Report mailed Oct. 16, 2019", 8 pgs.
"European Application Serial No. 19171990.5, Response filed May 13, 2020 to Extended European Search Report mailed Oct. 16, 2019", 31 pgs.
"European Application Serial No. 20175535.2, Extended European Search Report mailed Aug. 18, 2021", 16 pgs.
"European Application Serial No. 20175535.2, Partial European Search Report mailed May 18, 2021", 18 pgs.
"European Application Serial No. 20175535.2, Response Filed Mar. 15, 2022 to Extended European Search Report mailed Aug. 18, 2021", 31 pgs.
"European Application Serial No. 21177256.1, Extended European Search Report mailed May 17, 2022", 9 pgs.
"European Application Serial No. 21178298.2, Extended European Search Report mailed Mar. 1, 2022", 9 pgs.
"Gender Solutions Natural Knee Flex System: Because Men and Women are Different", Zimmer, Inc., (2007, 2009), 6 pg.
"Gender Solutions Natural Knee Flex System: Surgical Technique", Zimmer, Inc., (2007, 2008, 2009), 36 pgs.
"Gender Solutions Natural-Knee Flex System", Zimmer, Inc., (2007, 2009), 6 pgs.
"Indian Application Serial No. 1544/DELNP/2013, Office Action mailed May 21, 2019", (W/ English Translation), 10 pgs.
"Indian Application Serial No. 1544/DELNP/2013, Response filed Nov. 18, 2019 to Office Action mailed May 21, 2019", (W/ English Translation), 34 pgs.
"Indian Application Serial No. 1545/DELNP/2013, Office Action mailed Dec. 9, 2019", (with English translation), 8 pages.
"Indian Application Serial No. 1545/DELNP/2013, Response filed Jun. 9, 2020 to Office Action mailed Dec. 9, 2019", (W/ English Claims), 78 pgs.
"International Application Serial No. PCT/US2011/045077, International Preliminary Report on Patentability mailed Jul. 5, 2012", 23 pgs.
"International Application Serial No. PCT/US2011/045077, International Search Report and Written Opinion mailed Jan. 9, 2012", 15 pgs.
"International Application Serial No. PCT/US2011/045078, International Preliminary Report on Patentability mailed Feb. 7, 2013", 11 pgs.
"International Application Serial No. PCT/US2011/045078, International Search Report and Written Opinion mailed Jan. 9, 2012", 14 pgs.
"International Application Serial No. PCT/US2011/045080, International Preliminary Report on Patentability mailed Feb. 7, 2013", 13 pgs.
"International Application Serial No. PCT/US2011/045080, International Search Report mailed Jan. 9, 2012", 7 pgs.
"International Application Serial No. PCT/US2011/045080, Written Opinion mailed Jan. 9, 2012", 11 pgs.
"International Application Serial No. PCT/US2011/045082, International Preliminary Report on Patentability mailed Feb. 7, 2013", 11 pgs.
"International Application Serial No. PCT/US2011/045082, International Search Report mailed Jan. 9, 2012", 5 pgs.
"International Application Serial No. PCT/US2011/045082, Written Opinion mailed Jan. 9, 2012", 10 pgs.
"International Application Serial No. PCT/US2011/045083, International Preliminary Report on Patentability mailed Feb. 7, 2013", 8 pgs.
"International Application Serial No. PCT/US2011/045083, International Search Report mailed Dec. 7, 2011", 2 pgs.
"International Application Serial No. PCT/US2011/045083, Written Opinion mailed Dec. 7, 2011", 6 pgs.
"International Application Serial No. PCT/US2011/051021, International Preliminary Report on Patentability mailed Mar. 21, 2013", 8 pgs.
"International Application Serial No. PCT/US2011/051021, International Search Report mailed Nov. 23, 2011", 12 pgs.
"International Application Serial No. PCT/US2011/051021, Written Opinion mailed Nov. 23, 2011", 7 pgs.
"International Application Serial No. PCT/US2011/064435, International Preliminary Report on Patentability mailed Jun. 27, 2013", 9 pgs.
"International Application Serial No. PCT/US2011/064435, Search Report mailed Jun. 21, 2012", 5 pgs.
"International Application Serial No. PCT/US2011/064435, Written Opinion mailed Jun. 21, 2012", 7 pgs.
"International Application Serial No. PCT/US2011/065683, International Preliminary Report on Patentability mailed Jun. 27, 2013", 11 pgs.
"International Application Serial No. PCT/US2011/065683, International Search Report mailed Apr. 24, 2012", 12 pgs.
"International Application Serial No. PCT/US2011/065683, Written Opinion mailed Apr. 24, 2012", 10 pgs.
"International Application Serial No. PCT/US2012/035679, International Preliminary Report on Patentability mailed May 30, 2014", 8 pgs.
"International Application Serial No. PCT/US2012/035679, International Search Report mailed Jun. 8, 2012", 4 pgs.
"International Application Serial No. PCT/US2012/035679, Written Opinion mailed Jun. 8, 2012", 7 pgs.
"International Application Serial No. PCT/US2012/035680, International Preliminary Report on Patentability mailed May 30, 2014", 13 pgs.
"International Application Serial No. PCT/US2012/035680, Search Report mailed Oct. 9, 2012", 7 pgs.
"International Application Serial No. PCT/US2012/035680, Written Opinion mailed Oct. 9, 2012", 11 pgs.
"International Application Serial No. PCT/US2012/035683, International Preliminary Report on Patentability mailed May 30, 2014", 9 pgs.
"International Application Serial No. PCT/US2012/035683, International Search Report and Written Opinion mailed Jun. 5, 2012", 12 pgs.
"International Application Serial No. PCT/US2012/035684, International Preliminary Report on Patentability mailed May 30, 2014", 14 pgs.
"International Application Serial No. PCT/US2012/035684, International Search Report mailed Aug. 8, 2012", 9 pgs.
"International Application Serial No. PCT/US2012/035684, Written Opinion mailed Jun. 8, 2012", 12 pgs.
"International Application Serial No. PCT/US2012/052132, International Preliminary Report on Patentability mailed Jun. 5, 2014", 12 pgs.
"International Application Serial No. PCT/US2012/052132, International Search Report mailed Jan. 10, 2013", 5 pgs.
"International Application Serial No. PCT/US2012/052132, Invitation to Pay Additional Fees and Partial Search Report mailed Nov. 15, 2012", 7 pgs.
"International Application Serial No. PCT/US2012/052132, Written Opinion mailed Jan. 10, 2013", 10 pgs.

(56)                    References Cited

OTHER PUBLICATIONS

"International Application Serial No. PCT/US2012/052340, International Preliminary Report on Patentability mailed Aug. 14, 2014", 8 pgs.
"International Application Serial No. PCT/US2012/052340, Search Report mailed Oct. 12, 2012", 4 pgs.
"International Application Serial No. PCT/US2012/052340, Written Opinion mailed Oct. 12, 2012", 6 pgs.
"International Application Serial No. PCT/US2013/034286, International Preliminary Report on Patentability mailed Oct. 9, 2014", 8 pgs.
"International Application Serial No. PCT/US2013/034286, International Search Report mailed Jun. 25, 2013", 6 pgs.
"International Application Serial No. PCT/US2013/034286, Written Opinion mailed Jun. 25, 2013", 6 pgs.
"International Application Serial No. PCT/US2013/034293, International Preliminary Report on Patentability mailed Oct. 9, 2014", 9 pgs.
"International Application Serial No. PCT/US2013/034293, International Search Report mailed Jun. 25, 2013", 6 pgs.
"International Application Serial No. PCT/US2013/034293, Written Opinion mailed Jun. 25, 2013", 7 pgs.
"International Application Serial No. PCT/US2016/052163, International Preliminary Report on Patentability Mailed Apr. 5, 2018", 10 pgs.
"International Application Serial No. PCT/US2016/052163, International Search Report mailed Jan. 20, 2017", 7 pgs.
"International Application Serial No. PCT/US2016/052163, Invitation to Pay Add'l Fees and Partial Search Report mailed Nov. 7, 2016", 7 pgs.
"International Application Serial No. PCT/US2016/052163, Written Opinion mailed Jan. 20, 2017", 8 pgs.
"International Application Serial No. PCT/US2018/021571, International Preliminary Report on Patentability mailed Sep. 19, 2019", 8 pgs.
"International Application Serial No. PCT/US2018/021571, International Search Report mailed Jun. 7, 2018", 6 pgs.
"International Application Serial No. PCT/US2018/021571, Written Opinion mailed Jun. 7, 2018", 6 pgs.
"International Application Serial No. PCT/US2018/031177, International Preliminary Report on Patentability mailed Nov. 21, 2019", 8 pgs.
"International Application Serial No. PCT/US2018/031177, International Search Report mailed Jul. 31, 2018", 6 pgs.
"International Application Serial No. PCT/US2018/031177, Written Opinion mailed Jul. 31, 2018", 6 pgs.
"Intramedullary Instrumentation Surgical Technique for the NexGen Cruciate Retaining & Legacy Posterior Stabilized Knee", Zimmer, Inc. Nexgen Complete Knee Solution, 97-5973-102, Rev. 1, (1995, 1997, 1998), 36 pgs.
"Japanese Application Serial No. 2015-162707, Office Action mailed Jun. 28, 2016", (W/ English Translation), 8 pgs.
"Japanese Application Serial No. 2013-521854, Notice of Reason for Rejection mailed Sep. 16, 2014", (W/ English Translation), 6 pgs.
"Japanese Application Serial No. 2013-521854, Response filed Dec. 16, 2014 to Notice of Reason for Rejection mailed Sep. 16, 2014", W/ English Claims, 11 pgs.
"Japanese Application Serial No. 2013-521855, Amendment filed Jul. 22, 2014", (W/ English Translation), 20 pgs.
"Japanese Application Serial No. 2013-521855, Office Action mailed Mar. 24, 2015", W/ English Translation, 8 pgs.
"Japanese Application Serial No. 2013-521856, Notice of Allowance mailed Jan. 5, 2016", w/English Translation, 6 pgs.
"Japanese Application Serial No. 2013-521856, Office Action mailed Sep. 1, 2015", (W/ English Translation), 5 pgs.
"Japanese Application Serial No. 2013-521856, Response filed Dec. 1, 2015 to Office Action mailed Sep. 1, 2015", w/English Translation, 9 pgs.

"Japanese Application Serial No. 2013-521857, Notice of Allowance mailed Feb. 9, 2016", w/English Translation, 6 pgs.
"Japanese Application Serial No. 2013-521857, Notice of Reasons for Rejection mailed Aug. 18, 2015", (W/ English Translation), 6 pgs.
"Japanese Application Serial No. 2013-521857, Preliminary Amendment filed May 18, 2014", (W/ English translation of claims), 9 pgs.
"Japanese Application Serial No. 2013-521857, Response filed Jan. 25, 2016 to Notice of Reasons for Rejection mailed Aug. 18, 2015", (W/ English Translation), 17 pgs.
"Japanese Application Serial No. 2013-544655, Office Action mailed Mar. 8, 2016", (W/ English Translation), 8 pgs.
"Japanese Application Serial No. 2013-544655, Office Action mailed Sep. 29, 2015", (W/ English Translation), 7 pgs.
"Japanese Application Serial No. 2013-544655, Response filed Jan. 4, 2016 to Office Action mailed Sep. 29, 2015", (English Translation of Claims), 14 pgs.
"Japanese Application Serial No. 2013-544655, Response filed Jul. 14, 2016 to Office Action mailed Mar. 8, 2016", (w/ English Translation of Claims), 13 pgs.
"Japanese Application Serial No. 2013-544858, Request for Examination filed Feb. 4, 2014", (With English Translation), 14 pgs.
"Japanese Application Serial No. 2014-121515, Notice of Reasons for Rejection mailed Jan. 5, 2016", (W/ English Translation), 9 pgs.
"Japanese Application Serial No. 2014-121515, Office Action mailed Jun. 2, 2015", (W/ English Translation), 10 pgs.
"Japanese Application Serial No. 2014-121515, Response filed May 11, 2016 to Notice of Reasons for Rejection mailed Jan. 5, 2016", (W/ English Translation Of Claims), 11 pgs.
"Japanese Application Serial No. 2014-121515, Response filed Aug. 20, 2015 to Office Action mailed Jun. 2, 2015", (W/ English Translation Of Claims), 6 pgs.
"Japanese Application Serial No. 2014-542297, Office Action mailed May 31, 2016", (W/ English Translation Of Claims), 6 pgs.
"Japanese Application Serial No. 2014-542297, Office Action mailed Jun. 30, 2015", (W/ English Translation), 10 pgs.
"Japanese Application Serial No. 2014-542297, Office Action mailed Nov. 24, 2015", (W/ English Translation), 10 pgs.
"Japanese Application Serial No. 2014-542297, Response filed Feb. 23, 2016 to Office Action mailed Nov. 24, 2015", (W/ English Translation Of Claims), 15 pgs.
"Japanese Application Serial No. 2014-542297, Response filed Jun. 8, 2016 to Office Action mailed May 31, 2016", (W/ English Translation Of Claims), 14 pgs.
"Japanese Application Serial No. 2014-542297, Response filed Sep. 28, 2015 to Office Action mailed Jun. 30, 2015", (W/ English Translation Of Claims), 16 pgs.
"Japanese Application Serial No. 2014-542301, Office Action mailed May 12, 2015", (W/ English Translation), 6 pgs.
"Japanese Application Serial No. 2014-542301, Response filed Aug. 10, 2015 to Office Action mailed May 12, 2015", (W/ English translation of claims), 21 pgs.
"Japanese Application Serial No. 2014-554709, Office Action mailed Jul. 5, 2016", (W/ English Translation), 6 pgs.
"Japanese Application Serial No. 2014-554709, Preliminary Amendment filed Jul. 29, 2015", (W/ English translation of claims), 8 pgs.
"Japanese Application Serial No. 2014-554709, Response filed Dec. 19, 2016 to Office Action mailed Jul. 5, 2016", (W/ English Translation of Claims), 11 pgs.
"Japanese Application Serial No. 2015-162707, Office Action mailed Nov. 29, 2016", (W/ English Translation), 3 pgs.
"Japanese Application Serial No. 2015-162707, Response filed Jan. 26, 2017 to Office Action mailed Nov. 27, 2016", (W/ English Translation), 16 pgs.
"Japanese Application Serial No. 2015-199496, Office Action mailed Sep. 6, 2016", (W/ English Translation), 5 pgs.
"Japanese Application Serial No. 2015-199496, Response filed Dec. 5, 2016 to Office Action mailed Sep. 6, 2016", (W/ English Translation of Claims), 9 pgs.
"Japanese Application Serial No. 2015-503563, Office Action mailed Dec. 20, 2016", (W/ English Translation), 10 pgs.

(56)  References Cited

OTHER PUBLICATIONS

"Japanese Application Serial No. 2015-503563, Response Filed Mar. 13, 2017 to Office Action Mailed Dec. 20, 2016", (W/ English Translation), 9 pgs.

"Japanese Application Serial No. 2016-145390, Office Action mailed Apr. 25, 2017", (W/ English Translation), 5 pgs.

"Japanese Application Serial No. 2016-145390, Response filed Jul. 3, 2017 to Office Action mailed Apr. 25, 2017", (W/ English Translation of Claims), 16 pgs.

"Japanese Application Serial No. 2017-161246, Office Action mailed May 15, 2018", (W/ English Translation), 6 pgs.

"Japanese Application Serial No. 2019-562605, Notification of Reasons for Refusal mailed Jun. 16, 2020", (W/ English Translation), 7 pgs.

"Japanese Application Serial No. 2019-562605, Notification of Reasons for Refusal mailed Nov. 10, 2020", (W/ English Translation), 5 pgs.

"Japanese Application Serial No. 2019-562605, Response filed Feb. 9, 2021 to Notification of Reasons for Refusal mailed Nov. 10, 2020", (W/ English Claims), 19 pgs.

"Japanese Application Serial No. 2019-562605, Response filed Sep. 15, 2020 to Notification of Reasons for Refusal mailed Jun. 16, 2020", (W/ English Claims), 15 pgs.

"Japanese Application Serial No. 2021-097369, Notification of Reasons for Rejection mailed Jun. 14, 2022", w/ English Translation, 11 pgs.

"Journey II XR, Bi-Cruciate Retaining Knee System", Smith & Nephew, Surgical Technique, (2015), 40 pgs.

"Legacy Implant Options", Nexgen Complete Knee Solution, (2002), 8 pgs.

"LPS-Flex Fixed Bearing Knee: Surgical Technique", Zimmer, Inc., (2004, 2007, 2008), 16 pgs.

"Mexican Application Serial No. 2016/001734, Response filed Aug. 31, 2021 to Office Action mailed Jun. 7, 2021", (W/ English Translation of Claims), 29 pgs.

"Mexican Application Serial No. MX/a/2013/000988, Office Action mailed Mar. 18, 2015", w/English Claims, 17 pgs.

"Mexican Application Serial No. MX/a/2013/000988, Response filed Jun. 1, 2015 to Office Action mailed Mar. 18, 2015", (W/ English Translation), 12 pgs.

"Mexican Application Serial No. MX/A/2013/000988. Office Action Mailed Jun. 5, 2015", w/ summary in English, 6 pgs.

"Mexican Application Serial No. MX/A/2013/000990, Final Office Action mailed Feb. 4, 2016", w/ summary in English, 4 pgs.

"Mexican Application Serial No. MX/A/2013/000990, Office Action mailed Feb. 19, 2015", (W/ English Translation), 4 pgs.

"Mexican Application Serial No. MX/A/2013/000990, Response filed Apr. 29, 2015 to Office Action mailed Feb. 19, 2015", W/ English Claims, 18 pgs.

"MIS Minimally Invasive Solution, The M/G Unicompartmental Knee Minimally Invasive Surgical Technique", Zimmer, Inc. Nexgen Complete Knee Solution, 97-5791-02, (Aug. 14, 2008), 27 pgs.

"Multi-Reference 4-in-1 Femoral Instrumentation Surgical Technique for NexGen Cruciate Retaining & NexGen Legacy Posterior Stabilized Knees", Zimmer, Inc. Nexgen Complete Knee Solution, 97-5973-402 Rev. 1, (1998, 2000), 18 pgs.

"Natural-Knee II Primary System Surgical Technique", Zimmer, Inc., (2005), 48 pgs.

"Nexgen Complete Knee Solution", Extramedullary/Intramedullary Tibial Resector: Surgical Technique, Zimmer, Inc. 97-5997-002-00 Rev. 2, (2000, 2008, 2009), 28 pgs.

"Nexgen Complete Knee Solution", Extramedullary/Intramedullary Tibial Resector: Surgical Technique, Zimmer, Inc. 97-5997-02 Rev 1, (2000), 26 pgs.

"Nexgen Complete Knee Solution for the Legacy Knee LPS-Flex Fixed Bearing Knee", Zimmer Surgical Technique, 97-5964-102-00, (2004, 2007), 12 pgs.

"NexGen Complete Knee Solution, Intramedullary Instrumentation Surgical Technique for the NexGen Cruciate Retaining & Legacy Posterior Stabilized Knee", Zimmer, Inc., (1995, 1997, 1998), 1-33.

"NexGen Implant Options Surgeon-Specific", Zimmer Inc., (2000), 16 pgs.

"NexGen LPS Fixed Knee: Surgical Technique", Zimmer Inc., (2002, 2008), 44 pgs.

"NexGen LPS-Flex Mobile and LPS-Mobile Bearing Knees", Zimmer, Inc., (2007, 2008), 4 pgs.

"NexGen Trabecular Metal Modular Plates", Zimmer Inc., (2007), 19 pgs.

"Persona "Medial Congruent Articular Surface" System Overview", Zimmer, Inc., (2015), 6 pgs.

"Persona "The Personalized Knee System"", Medial Congruent Sales Training, Zimmer, Inc., (Jul. 2015), 53 pgs.

"Persona "The Personalized Knee System" Medial Congruent Advanced Bearings", Zimmer, Inc., (2015), 2 pgs.

"Persona "The Personalized Knee System" Medial Congruent Articular Surface Design Rationale", Zimmer, Inc., (2015), 20 pgs.

"Persona "The Personalized Knee System" Persona Medial Congruent", Mar. 24-28, 2015 at the American Academy of Orthopaedic Surgeons (AAOS) Annual Meeting., (Mar. 2015), 1 pg.

"Persona "The Personalized Knee System" Surgical Technique", Zimmer, Inc., (2015), 72 pgs.

"Persona Medial Congruent Articular Surface", Sales Training, Zimmer Biomet, (Jan. 2016), 71 pgs.

"PFC Sigma Knee System with Rotating Platform Technical/ Monograph", Depuy PFC Sigma RP, 0611-29-050 (Rev. 3), (1999), 70 pgs.

"Primary/Revision Surgical Technique for NexGen Rotating Hinge Knee (RHK)", Zimmer, Inc. Nexgen Complete Knee Solution, 97-5880-02, (2002), 116 pgs.

"Revision Instrumentation Surgical Technique for Legacy Knee Constrained Condylar Knee", Zimmer, Inc. Nexgen Complete Knee Solution, 97-5994-202, (2001), 61 pgs.

"Russian Application Serial No. 2013106942, Office Action mailed Apr. 16, 2015", W/ English Translation, 5 pgs.

"Russian Application Serial No. 2013106942, Response filed Jul. 15, 2015 Office Action mailed Apr. 16, 2015", (W/ English translation of claims), 146 pgs.

"Russian Application Serial No. 2013106943, Office Action mailed Jul. 1, 2015", (W/ English Translation), 6 pgs.

"Russian Application Serial No. 2013106943, Office Action mailed Dec. 28, 2015", w/ partial English Translation, 6 pgs.

"Russian Application Serial No. 2013106943, Response filed Apr. 28, 2016 to Office Action mailed Dec. 28, 2015", (W/ English translation of claims), 19 pgs.

"Russian Application Serial No. 2013106943, Response filed Oct. 30, 2015 to Office Action mailed Jul. 1, 2015", (W/ English translation of claims), 21 pgs.

"South African Application Serial No. 2013/01327, Amendment filed Apr. 24, 2014", W/ English Translation, 4 pgs.

"South African Application Serial No. 2013/01328, Amendment filed Apr. 24, 2014", W/ English Translation, 4 pgs.

"Surgical Technique for Cruciate Retaining Knees and Revision Instrumentation Surgical Technique for Cruciate Retaining Augmentable Knees", Zimmer, Inc. Nexgen Complete Knee Solution, 97-5970-202, (2002), 130 pgs.

"Surgical Technique for the CR-Flex Fixed Bearing Knee", NexGen Complete Knee Solution, Zimmer, Inc., (2003), 22 pgs.

"Surgical Technique for the Legacy Knee LPS-Flex Fixed Bearing Knee", Zimmer, Inc. Nexgen Complete Knee Solution, 97-5964-02, Rev. 1, (2000, 2002), 15 pgs.

"Surgical Technique for the Legacy Posterior Stabilized Knees", Zimmer, Inc. Nexgen Complete Knee Solution, 97-5996-02, (2002), 43 pgs.

"Surgical Technique—Nexgen Complete Knee Solution for the Legacy Knee LPS-Flex Fixed Bearing Knee", Zimmer, Inc., (2004, 2007), 12 pgs.

"The Zimmer Institute Surgical Technique MIS Quad-Sparing Surgical Technique for Total Knee Arthroplasty", NExGen Complete Knee Solution, (2004), 55 pgs.

"Tibial Baseplate: Pocket Guide (United States Version)", Zimmer, Inc.,, (2009), 17 pgs.

"Trabecular Metal Monoblock Tibial Components", Zimmer, Inc., (2007), 4 pgs.

(56)                    References Cited

OTHER PUBLICATIONS

"Trabecular Metal Monoblock Tibial Components Surgical Technique Addendum", Nexgen Zimmer, Inc., (2005, 2007), 12 pgs.

"Trabecular Metal Tibial Tray: Surgical Technique", NexGen Zimmer, Inc., (2007, 2009), 16 pgs.

"Turkish Application Serial No. 11808493.8, Working Requirements mailed Feb. 17, 2020", 3 pgs.

"Turkish Application Serial No. 12718882.9, Working Requirements mailed Feb. 13, 2020", 3 pgs.

"Vanguard® ID Total Knee, Surgical Technique", Zimmer Biomet; 0682.1-GLBL-en-REV0317, (2017), 36 pgs.

"Zimmer MIS Intramedullary Instrumentation Surgical Technique For NexGen Cruciate Retaining & NexGen Legacy Posterior Stabilized Knees", printed 2005, 2009, Zimmer, Inc., (2009), 45 pgs.

"Zimmer Nexgen Cruciate Retaining (CR) and Legacy Knee Posterior Stabilized (LPS) Trabecular Metal Monoblock Tibias", Zimmer, Inc Surgical Technique Addendum, 97-7253-34, Rev. 3, (2004), 11 pgs.

"Zimmer NexGen CR-Flex and LPS-Flex Knees Surgical Technique with posterior Referencing Instrumentation.", Zimmer Inc., (2010, 2011), 48 pgs.

"Zimmer NexGen LCCK Surgical Technique for use with LCCK 4-in-1 Instrumentation", Zimmer, Inc.; copyright 2009, 2010, 2011, (May 2011), 52 pgs.

"Zimmer NexGen MIS Modular Tibial Plate and Keel Cemented Surgical Technique"; Zimmer Inc., (2006, 2011), 26 pgs.

"Zimmer NexGen MIS Tibial Component", Brochure-97-5950-001-00 7.5mm, (2005, 2006), 8 pgs.

"Zimmer NexGen MIS Tibial Component Cemented Surgical Technique", Zimmer, Inc, #97-5950-002-00 Rev.1 1.5ML, (2005), 14 pgs.

"Zimmer NexGen MIS Tibial Component Cemented Surgical Technique", Zimmer Inc., (2005, 2006, 2008, 2009, 2010), 16 pgs.

"Zimmer NexGen Trabecular Metal Augments—Abbreviated Surgical Technique", Zimmer, Inc., (2004, 2006), 6 pgs.

"Zimmer NexGen Trabecular Metal Augments Surgical Technique for LCCK & Rotating Hing Knee Trabecular Metal Augments", Zimmer, Inc. 97-5448-02, Rev. 1, (2004), 6 pgs.

"Zimmer NexGen Trabecular Metal Primary Patella Surgical Technique", Zimmer. Inc., 97-7255-112-00, (2005), 10 pgs.

"Zimmer NexGen Trabecular Metal Tibial Tray", Surgical Technique, Zimmer, Inc., (2007, 2009), 16 pgs.

"Zimmer Patient Specific Instruments", Surgical Techniques for NexGen Complete Knee Solution Zimmer, Inc., (2010), 16 pgs.

Annayappa, Ramesh, "Tibial Prosthesis", U.S. Appl. No. 13/189,328, filed Jul. 22, 2011, 82 pgs.

Annayappa, Ramesh, et al., "Tibial Prosthesis", U.S. Appl. No. 13/189,324, filed Jul. 22, 2011, 50 pgs.

Bellemans, Johan, et al., "Is Neutral Mechanical Alignment Normal for All Patients?", Clinical Orthopaedics and Related Research; DOI 10.1007/s11999-011-1936-5, (Jun. 9, 2011), 9 pgs.

Ding, M., et al., "Age-related variations in the microstructure of human tibial cancellous bone", Journal of Orthopaedic Research, 20(3), (2002), 615-621.

Ding, M., et al., "Changes in the three-dimensional microstructure of human tibial cancellous bone in early osteoarthritis", Journal of Bone & Joint Surgery (British), 85-B(6), (Aug. 2003), 906-912.

Doyle, et al., "Comparative Analysis of Human Trabecular Bone and Polyurethane Foam", Purdue University., (Accessed online Jul. 24, 2013), 1 pg.

Dunbar, M. J., et al., "Fixation of a Trabecular Metal Knee Arthroplasty Component: A Prospective Randomized Study", The Journal of Bone & Joint Surgery (American), vol. 91-A(7), (Jul. 2009), 1578-1586.

Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.

Freeman, M.A.R., et al., "The Movement of the Knee Studied by Magnetic Resonance Imaging", Advanced Bearings—Clinical Orthopedics & Related Research 2003, (2003), 1 pg.

Hofmann, Aaron A, et al., "Posterior Stabilization in Total Knee Arthroplasty with Use of an Ultracongruent Polyethylene", The Journal of Arthroplasty vol. 15, No. 5, (2000), 576-583.

Hutt, Jonathan, et al., "Functional joint line obliquity after kinematic total knee arthroplasty", International Orthopaedics; DOI 10.1007/s00264-015-2733-7, (Mar. 21, 2015), 6 pgs.

Hvid, Ivan, et al., "Trabecular bone Strength Patterns at the Proximal Tibial Epiphysis", Journal of Orthopaedic Research, vol. 3, No. 4, (1985), 464-472.

Klostermann, et al., "Distribution of bone mineral density with age and gender in the proximal tibia", Clinical Biomechanics 19, (2004), pp. 370-376.

Lorenz, Stephan, et al., "Radiological evaluation of the anterolateral and posteromedial bundle insertion sites of the posterior cruciate ligament", Knee Surg Sports Traumatol Arthosc, vol. 17, (2009), 683-690.

Moorman, Claude, et al., "Tibial Insertion of the Posterior Cruciate Ligament: A Sagittal Plane Analysis Using Gross, Histologic, and Radiographic Methods", Arthroscopy: The Journal of Arthroscopic and Related Surgery, vol. 24, No. 3, (Mar. 2008), 269-275.

Parisi, Raymond C, "Motion Facilitating Tibial Components for a Knee Prosthesis", U.S. Appl. No. 13/229,103, filed Sep. 9, 2011, 46 pgs.

Partovi, Hamid, "Flow-Through Latch and Edge-Triggered Flip-Flop Hybrid Elements", Proceedings of the IEEE International Solid-State Circuits Conference, Digest of Technical Papers and Slide Supplement, NexGen Inc., Milpitas, CA, (1996), 40 pgs.

Siggelkow, Eik, et al., "Impact of Tibia Bearing Surface and Femoral Component Design on Flexion Kinematics During Lunge", Mar. 28-31, 2015 at the Orthopaedic Research Society (ORS) Annual Meeting (Poster #1645), (Mar. 2015), 1 pg.

Siggelkow, Eik, et al., "Impact of Tibia Bearing Surface Design on Deep Knee Bend Kinematics", Mar. 24-28, 2015 at the AAOS Conference (Poster #P142), (Mar. 2015), 1 pg.

Stilling, et al., "Superior fixation of pegged trabecular metal over screw-fixed pegged porous titanium fiber mesh", Acta Orthopaedica., (2011), 177-186.

Victor, Jan M. K., et al., "Constitutional Varus Does Not Affect Joint Line Orientation in the Coronal Plane", Joint Line Orientation in the Coronal Plane; 472; DOI 10.1007/s11999-013-2898-6, (Jun. 4, 2013), pp. 98-104.

Wentorf, Mary S. S, "Asymmetric Tibial Components for a Knee Prosthesis", U.S. Appl. No. 13/189,338, filed Jul. 22, 2011, 58 pgs.

Wentorf, Mary S. S, "Asymmetric Tibial Components for a Knee Prosthesis", U.S. Appl. No. 13/189,339, filed Jul. 22, 2011, 52 pgs.

Wentorf, Mary S. S, "Asymmetric Tibial Components for a Knee Prosthesis", U.S. Appl. No. 13/189,336, filed Jul. 22, 2011, 60 pgs.

"U.S. Appl. No. 17/068,435, Non Final Office Action mailed Jun. 15, 2023", 13 pgs.

"U.S. Appl. No. 17/068,435, Notice of Allowance mailed Oct. 17, 2023", 5 pgs.

"U.S. Appl. No. 17/068,435, Response filed Sep. 12, 2023 to Non Final Office Action mailed Jun. 15, 2023", 11 pgs.

"U.S. Appl. No. 17/545,728, Final Office Action mailed Feb. 20, 2024", 17 pgs.

"U.S. Appl. No. 17/545,728, Non Final Office Action mailed Sep. 22, 2023", 16 pgs.

"U.S. Appl. No. 17/545,728, Response filed Dec. 12, 2023 to Non Final Office Action mailed Sep. 22, 2023", 16 pgs.

"U.S. Appl. No. 18/228,322, Preliminary Amendment filed Aug. 16, 2023", 6 pgs.

"Chinese Application Serial No. 202110590378.1, Office Action mailed Dec. 26, 2023", w/ English Translation, 15 pgs.

"European Application Serial No. 18726670.5, Response filed Apr. 25, 2023 to Communication Pursuant to Article 94(3) EPC mailed Dec. 15, 2022", 35 pgs.

"European Application Serial No. 21177256.1, Communication Pursuant to Article 94(3) EPC mailed Jun. 7, 2023", 4 pgs.

(56)          References Cited

OTHER PUBLICATIONS

"European Application Serial No. 21177256.1, Response filed Oct. 17, 2023 to Communication Pursuant to Article 94(3) EPC mailed Jun. 7, 2023", 10 pgs.
"European Application Serial No. 21178298.2, Communication Pursuant to Article 94(3) EPC mailed Nov. 29, 2023", 5 pgs.
"European Application Serial No. 21178298.2, Response filed Feb. 29, 2024 to Communication Pursuant to Article 94(3) EPC mailed Nov. 29, 2023", 21 pgs.
"U.S. Appl. No. 17/134,885, Non Final Office Action mailed Nov. 21, 2024", 9 pgs.
"U.S. Appl. No. 17/134,885, Notice of Allowance mailed Feb. 25, 2025", 5 pgs.
"U.S. Appl. No. 17/134,885, PTO Response to Rule 312 Communication mailed Jul. 15, 2025", 2 pgs.
"U.S. Appl. No. 17/134,885, Response filed Feb. 12, 2025 to Non Final Office Action mailed Nov. 21, 2024", 12 pgs.
"U.S. Appl. No. 17/545,728, Appeal Brief filed Sep. 9, 2024", 25 pgs.
"U.S. Appl. No. 17/545,728, Notice of Allowance mailed Nov. 8, 2024", 17 pgs.
"U.S. Appl. No. 17/717,898, Non Final Office Action mailed Jun. 10, 2025", 23 pgs.
"U.S. Appl. No. 17/717,898, Response filed Sep. 8, 2025 to Non Final Office Action mailed Jun. 10, 2025", 19 pgs.
"U.S. Appl. No. 18/081,481, Final Office Action mailed Apr. 8, 2025", 6 pgs.
"U.S. Appl. No. 18/081,481, Non Final Office Action mailed Oct. 9, 2024", 9 pgs.
"U.S. Appl. No. 18/081,481, Notice of Allowance mailed Jul. 15, 2025", 7 pgs.
"U.S. Appl. No. 18/081,481, Response filed Jan. 7, 2025 to Non Final Office Action mailed Oct. 9, 2024", 14 pgs.
"U.S. Appl. No. 18/081,481, Response filed Jun. 2, 2025 to Final Office Action mailed Apr. 8, 2025", 14 pgs.
"U.S. Appl. No. 19/038,621, Preliminary Amendment filed Jan. 28, 2025".
"Chinese Application Serial No. 202110590378.1, Response Filed Mar. 18, 2024 to Office Action mailed Dec. 26, 2023", W/ English Claims, 19 pgs.
"European Application Serial No. 24215248.6, Extended European Search Report mailed Mar. 18, 2025", 4 pgs.
"European Application Serial No. 24215248.6, Response Filed Aug. 27, 2025 to Extended European Search Report mailed Mar. 18, 2025", 8 pgs.
"European Application Serial No. 25162292.4, Extended European Search Report mailed May 20, 2025", 7 pgs.
"European Application Serial No. 25163024.0, Extended European Search Report mailed Jun. 25, 2025", 4 pgs.
"European Application Serial No. 25177136.6, Extended European Search Report mailed Sep. 3, 2025", 9 pgs.
"International Application Serial No. PCT US2011 045080, International Search Report mailed Feb. 29, 2012", 3 pgs.
"International Application Serial No. PCT US2011 045080, Written Opinion mailed Feb. 29, 2012", 5 pgs.
"International Application Serial No. PCT US2011 045080, International Preliminary Report on Patentability mailed Apr. 11, 2013", 7 pgs.
"U.S. Appl. No. 17/717,898, Final Office Action mailed Dec. 10, 2025", 13 pgs.

IMPLANTS FOR ADDING JOINT INCLINATION TO A KNEE ARTHROPLASTY

CLAIM OF PRIORITY

This application is a continuation of U.S. patent application Ser. No. 16/179,201, filed on Nov. 2, 2018, which claims the benefit of U.S. Provisional Patent Application Ser. No. 62/587,192, filed on Nov. 16, 2017, the benefit of priority of each of which is claimed hereby, and each of which is incorporated by reference herein in its entirety.

TECHNICAL FIELD

The present disclosure relates to knee arthroplasty. More particularly, the present disclosure relates to implants for use during a knee arthroplasty procedure, and to systems for using the same.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Various types of arthroplasties are known including a total knee arthroplasty (TKA), where all of the articulating compartments of the joint are repaired with prosthetic components.

Joint replacement prostheses commonly comprise two bone engaging components that articulate via a bearing component. In a total knee arthroplasty prosthesis, the bone engaging components are a femoral component, comprising an anterior surface with patella track and two femoral condyles, and a tibial component, comprising a substantially planar surface (commonly called a tray or baseplate). Additionally, the tibial component can have and a post, keel or other stabilizing feature. The femoral and tibial components articulate via the bearing component mounted on the tray of the tibial component. The bearing component may be fully or partially fixed with respect to the tibial component, and commonly comprises a single piece of high density polyethylene.

Overview

The present inventor has recognized that prior techniques for adding joint inclination into knee arthroplasty procedures by having a different thicknesses for portions of the bearing component (but with a no varus-valgus inclination for either portion) there is a risk of loss of congruency between the femoral component and the bearing component. Such congruency loss can result in edge or point loading of the femoral component on the bearing component, which could result in plastic deformation including possible volumetric polyethylene wear and possible revision.

Thus, the present inventor proposes an orthopedic knee prosthesis including a bearing component and/or a tibial baseplate that are configured to add joint inclination to a knee arthroplasty procedure. With regards to the bearing component, joint inclination can be accomplished by having different thicknesses for different portions of the bearing component and an inclination (e.g., 5°) for both portions.

Such inclination for the portions can substantially match one another according to some examples such that an overall inclination for the joint can be provided. With regards to the tibial baseplate, joint inclination can be accomplished by having a wedge shaped component (i.e., a medial portion of the tibial baseplate can have a different thickness than a lateral portion) so as to form an angle along its proximal surface. This configuration can add the joint inclination to the knee arthroplasty. Such a configuration for the bearing component and/or the tibial baseplate (examples are shown in reference to FIGS. 5-7) can minimize congruency loss between the femoral component and the bearing component.

The bearing component of the present invention can be monolithic, comprising a single component, or can be made of a bearing component that comprises separate distinct portions, e.g., medial and lateral portions. The bearing component can add joint inclination to the knee arthroplasty by varying the thicknesses of the medial and lateral portions relative to one another and by having an inclination for the articular surfaces of both the lateral and medial portions. A tibial baseplate of the present invention can additionally, or alternatively, include a wedge shape so as to form an angle along its proximal surface that can add the joint inclination to the knee arthroplasty. The joint inclination can be either varus or valgus as desired and for simplicity is referred to simply as varus-valgus herein. In some examples, the joint inclination can also be anterior-posterior and/or proximal-distal in addition to, or in alternative to, the varus-valgus inclinations shown in reference to FIGS. 5-7.

The knee prosthesis described in the application can facilitate expedient and effective surgical implantation, and can include trial families of bearing components and/or tibial baseplates from which the surgeon may choose intra-operatively. These trials for joint arthroplasty may otherwise be known as instruments and are not implanted within a patient's anatomy but rather are temporarily placed in the joint to simulate implants. These trials can have differing configurations so as to produce different degrees of joint inclination (varus-valgus, etc.). These trial families can also include a range of component sizes, different component designs (e.g., multi-portion bearing components, monolithic bearing components, etc.).

As used herein the term "varus-valgus" means either varus-to-valgus or valgus-to-varus. Similarly, the terms "proximal-distal", "medial-lateral" and "anterior-posterior" refer to either possible direction of reference for each term. Thus, for example, "proximal-distal" means either "proximal-to-distal" or "distal-to-proximal". The present disclosure includes both implants as well as trial components. Thus, the term "bearing component" as used herein covers both a bearing used with an implant and a bearing trial. Similarly, the term "tibial baseplate" as used herein covers bath a trial baseplate and an implant baseplate.

To further illustrate the knee prostheses and systems disclosed herein, a non-limiting list of examples is provided here:

Example 1 is a bearing component for a knee arthroplasty, the bearing component can optionally comprise any one or combination of: a medial compartment having an medial articular surface with a medial articular track and having a first thickness as measured at the medial articular track between the medial articular surface a medial distal surface; and a lateral compartment having a lateral articular surface with a lateral articular track and having a second thickness as measured at the lateral articular track between the lateral articular surface a lateral distal surface; wherein the medial articular surface at the medial articular track and the lateral articular surface at the lateral articular track each have an inclination so as to form an acute angle with respect to a resected proximal surface of a tibia.

In Example 2, the subject matter of Example 1 optionally includes the inclination is in a varus-valgus and proximal-distal direction only.

In Example 3, the subject matter of any one or more of Examples 1-2 optionally includes the bearing component is a monolithic single piece construct forming both the medial compartment and the lateral compartment.

In Example 4, the subject matter of any one or more of Examples 1-3 optionally include the bearing component comprises a two-piece bearing having the medial compartment separated from the lateral compartment.

In Example 5, the subject matter of any one or more of Examples 1-4 optionally include the inclination occurs at dwell points of the medial and lateral articular tracks.

In Example 6, the subject matter of any one or more of Examples 1-5 optionally include the inclination occurs for only a portion of an anterior-posterior extent of at least one of the medial articular track and the lateral articular track.

In Example 7, the subject matter of any one or more of Examples 1-6 optionally include the inclination occurs for substantially an entirety of an anterior-posterior extent of at least one of the medial articular track and the lateral articular track.

In Example 8, the subject matter of any one or more of Examples 1-7 optionally include the knee arthroplasty comprises one of a partial knee arthroplasty or a total knee arthroplasty.

In Example 9 is a tibial baseplate for a knee arthroplasty, the tibial baseplate can optionally comprise any one or any combination of: a distal surface configured to interface with and mount on a resected proximal surface of a tibia; a proximal surface opposing the distal surface and configured to couple with a bearing component, the proximal surface having an inclination in a varus-valgus direction so as to form an acute angle with respect to at least one of the resected proximal surface of the tibia and the distal surface.

In Example 10, the subject matter of Example 9 optionally includes a medial portion; a lateral portion opposing the medial portion, wherein a thickness of the lateral portion as measured between the proximal surface and the distal surface along a medial-lateral extent of the lateral portion that differs from a thickness of the medial portion as measured between the proximal surface and the distal surface along a medial-lateral extent of the medial portion.

In Example 11, the subject matter of Example 10 optionally includes the medial portion comprises a first component and the lateral portion comprises a second component, and wherein the first component is separate from the second component.

In Example 12, the subject matter of any one or more of Examples 9-11 optionally include the tibial baseplate is separated into at least two components comprising at least a medial component and a lateral component.

Example 13 is a system for a knee arthroplasty can optionally comprise any one or any combination of: a plurality of trial tibial baseplates, each of the plurality of trial tibial baseplates are configured to seat on one or more resected portions of the tibia, wherein at least some of the plurality of trial tibial baseplates have a proximal surface with an inclination in a varus-valgus direction relative to a distal surface thereof so as to form an acute angle therebetween, and wherein the at least some of the plurality of trial tibial baseplates are differently configured relative to one another to provide for a different degree for the acute angle;

and a plurality of trial bearing components each configured to couple with one or more of the plurality of trial tibial baseplates, wherein at least some of the trial bearing components each comprise: a medial compartment having an medial articular surface with a medial articular track and having a first thickness as measured at the medial articular track between the medial articular surface a medial distal surface, and a lateral compartment having a lateral articular surface with a lateral articular track and having a second thickness as measured at the lateral articular track between the lateral articular surface a lateral distal surface, wherein the medial articular surface at the medial articular track and the lateral articular surface at the lateral articular track each have an inclination so as to form an acute angle with respect to a resected proximal surface of a tibia, wherein the at least some of the plurality of bearing components are differently configured relative to one another to provide for a different degree for the acute angle.

In Example 14, the subject matter of Example 13 optionally includes the inclination of the at least some of the plurality of bearing components is in a varus-valgus and proximal-distal direction only.

In Example 15, the subject matter of any one or more of Examples 13-14 optionally include the at least some of the plurality of bearing components each are a monolithic single piece construct forming both the medial compartment and the lateral compartment.

In Example 16, the subject matter of any one or more of Examples 13-15 optionally include the at least some of the plurality of bearing components each comprise a two-piece bearing having the medial compartment separated from the lateral compartment.

In Example 17, the subject matter of any one or more of Examples 13-16 optionally include the inclination of the at least some of the plurality of bearing components occurs at dwell points of the medial and lateral articular tracks.

In Example 18, the subject matter of any one or more of Examples 13-17 optionally include the inclination of the at least some of the plurality of bearing components occurs for only a portion of an anterior-posterior extent of at least one of the medial articular track and the lateral articular track.

In Example 19, the subject matter of any one or more of Examples 13-18 optionally include the inclination of the at least some of the plurality of bearing components occurs for substantially an entirety of an anterior-posterior extent of at least one of the medial articular track and the lateral articular track.

In Example 20, the subject matter of any one or more of Examples 13-19 optionally include the knee arthroplasty comprises one of a partial knee arthroplasty, a bi-compartmental knee arthroplasty or a total knee arthroplasty.

In Example 21, the subject matter of any one or combination of Examples 1-20 can be optionally be used alone or in various combinations without limitation.

These and other examples and features of the present devices, systems, and methods will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, like numerals can be used to describe similar elements throughout the several views. The drawings illustrate generally, by way of example, but not by way of limitation, various examples discussed in the present document.

DETAILED DESCRIPTION

The present disclosure relates to implantable prostheses, trial instruments, and systems that can be used in knee replacement procedures such as total knee arthroplasty (TKA), and other suitable knee replacement procedures such as a partial knee arthroplasty like a bicompartmental knee arthroplasty wherein both medial and lateral tibiofemoral compartments are being replaced. TKA surgery, for example, can involve the implantation of prosthetic components meant to restore the functionality provided by a natural knee. Typical TKA components include a tibial baseplate, a femoral component, and a bearing component disposed between the tibial baseplate and the femoral component. In a bicompartmental knee arthroplasty, both a medial condyle and a lateral condyle of the femur and the tibia are resected to remove the medial articular surface and the lateral articular surface. Similar to a unicompartmental knee arthroplasty procedure, the bicompartmental knee arthroplasty maintains some portions of the knee in an un-resected state such as the intercondylar eminence or patellofemoral compartment. Bicompartmental knee arthroplasty can use the tibial baseplate, femoral component and the bearing component similar to TKA components but with modified construction.

The present disclosure provides knee prostheses and systems that include bearing components and/or tibial baseplates in which the components are configured to provide joint inclination to the TKA, bicompartmental knee arthroplasty, etc.

Before knee replacement surgery, a surgeon can preoperatively assess a patient's native joint line using any suitable method, such as, for example, by imaging technology (e.g., computed tomography (CT scan), x-ray, magnetic resonance imaging etc.). In order to prepare the tibia and femur for receipt of a knee prostheses including components of the present disclosure, any suitable methods or apparatuses for implantation of the knee joint prosthesis components can be used. During this process the surgeon can identify a patient's native joint line (indicated as 122 in FIG. 1) using the results from the digital imagining technology.

Several different approaches for a TKA procedure exist including a first technique that utilizes mechanical alignment of the knee prostheses and a second technique that utilizes kinematic alignment of the knee prostheses. The present methods and/or apparatuses of this disclosure can be useable with either the former technique or the latter technique. If used with the kinematic technique, the present apparatuses can be configured to take into account the relatively larger degree of native or natural varus joint inclination that a patient may present with and that may further result from that technique for the tibial baseplate, bearing component, and femoral component.

Figure 1:
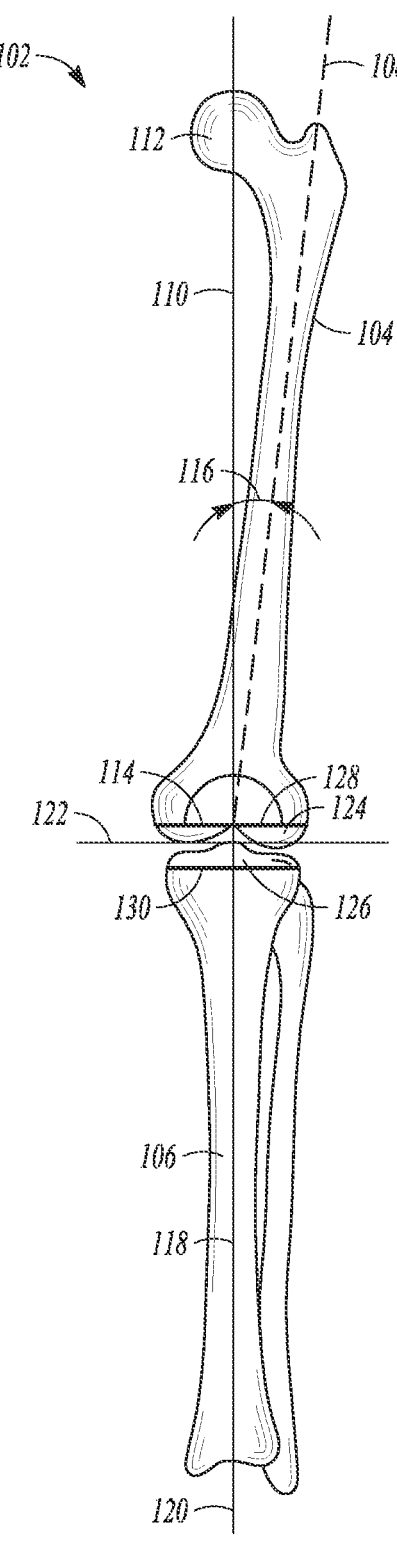
FIGS. 1-2 illustrate knee joint structures providing suitable environments in which a tibial prosthesis system, as constructed in accordance with at least one example of the present application, can be used.
Figure 2:
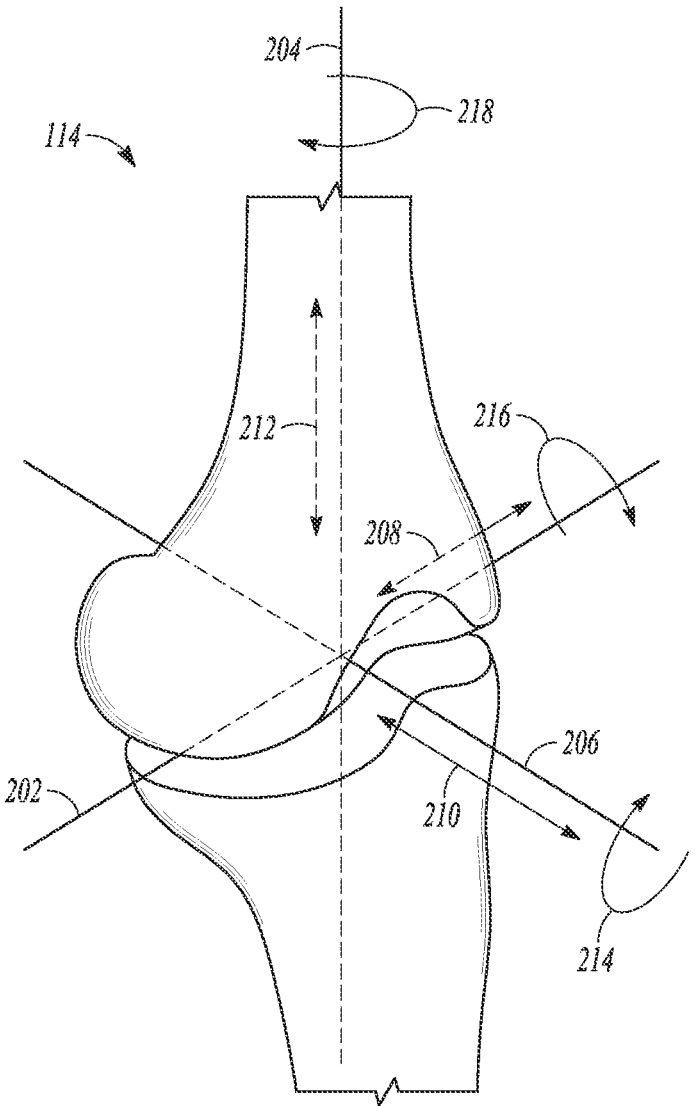

Mechanical alignment considers a three-dimensional (3D) alignment of the limb and the knee, including: aligning the femoral component perpendicular to the mechanical axis of the femur in the coronal plane by adjusting its varus-valgus alignment; aligning the tibial component perpendicular to the mechanical axis of the tibia in the coronal plane by adjusting its varus-valgus alignment; and, allowing the other five degrees of freedom to be adjusted by the surgeon's surgical technique. Namely, the considerations include adjusting the anterior-posterior, medial-lateral, proximal-distal, internal-external rotation, and flexion-extension axes of the femoral component. The considerations for the tibial component placement include a surgeon adjusting the anterior-posterior, medial-lateral, proximal-distal, internal-external rotation, and posterior slope. Kinematic alignment considers these same six degrees of freedom with respect to the knee, however the varus-valgus alignment of the femoral and tibial components may not be set perpendicular to the mechanical axes of the patient's anatomy. The intention of kinematic alignment is the restoration of the normal 3D orientation of three axes that describe normal knee kinematics. The primary goals of a kinematically aligned. TKA are (1) positioning the femoral and tibial components of a knee prosthesis such that the angles and levels of the distal and posterior femoral and tibial joint lines are restored to the patient's natural joint line (which may include the varus-valgus angle of the femoral and tibial components not being perpendicular to their respective mechanical axes), (2) restoration of the patient's natural or constitutional alignment prior to the patient having developed osteoarthritis, and (3) restoration of the patient's natural soft tissue laxity and envelope. FIGS. 1 and 2 illustrate several features of knee joint structures and orientations that are used in mechanical and kinematic alignment.

In FIG. 1, a frontal view of a lower limb 102, including a femur 104 and a tibia 106, is shown to illustrate various lower limb axes. The femur 104 has an anatomic axis 108 that coincides generally with its intramedullary canal. The femur 104 also has a mechanical axis 110, or load axis, running from the center of a femoral head 112 to the center of a knee joint 114. The angle 116 extending between these two axes varies among the patient population, but is generally on the order of between 5-7 degrees, inclusive. Like the femur 104, the tibia 106 also has an anatomic axis coinciding generally with its intramedullary canal. The mechanical axis 118 of the tibia 106 runs from the center of the knee joint 114 to the center of an ankle region 120 and is generally collinear with its anatomic axis.

A patient's native joint line 122, about which the knee joint 114 flexes and extends, has an approximate degree of inclination to a line through medial and lateral femoral condyles 124 and to a tibial plateau 126. Although illustrated as perpendicular in FIG. 1, the joint line 122 can extend at a varus or valgus angle (usually of a few degrees) relative to the mechanical axes 110 and 118 of the femur 104 and tibia 106, respectively and thereby not be perpendicular to these noted mechanical axes of the femur and tibia. Normally, during a mechanically aligned total knee replacement procedure, portions of a distal end of the femur 104 and/or a proximal end of the tibia 106 are resected to be perpendicular to the mechanical axes 110 of the femur and 118 of the tibia. Thereby placing the patient's joint line 122 approximately perpendicular to the femoral mechanical axis 110 and the tibial mechanical axis 118. The resected cut planes of the femur and tibia are indicated at 128 and 130, respectively. During a kinematically aligned total knee replacement procedure, portions of a distal end of the femur 104 and/or a proximal end of the tibia 106 are resected to be not perpendicular to the mechanical axes 110 of the femur and 118 of the tibia. In this kinematically aligned total knee procedure, the resected cut planes of the femur and tibia, 128 and 130 respectively, are resected to be parallel to the patient's normal joint line, 122, which may have some degree of inclination, or angle.

With the systems and apparatuses of the present application the proximal end of the tibia 106 need not be resected to be parallel or approximately parallel to the match the patient's native joint line 122. Therefore, with the present systems and apparatuses, line 130 need not be parallel to joint line 122. Thus, the present methods and apparatuses can reduce surgical time as time consuming matching of the tibial resection 130 to the joint line 122 is not necessary. Rather, with the present systems and apparatuses, a resection to form line 130 can simply be performed to mechanically match the tibial axis 118 and the bearing component and/or the tibial baseplate can then be selected to add a desired joint inclination for the implant assembly. This joint inclination can substantially match the patient's native joint line (e.g., joint line 122). It is also contemplated that differing medial and lateral soft-tissue tensions can be provided for the knee via the configuration of bearing component and/or the tibial baseplate that provides for the joint inclination.

FIG. 2 illustrates a closer view of the knee joint 114 and its coordinate system, in which a medial-lateral axis 202 corresponds approximately to the joint line 122 (FIG. 1), a proximal-distal axis 204 corresponds approximately to the mechanical axes 110 and 118 (FIG. 1) or approximately to the anatomic axis 108 (FIG. 1). An anterior-posterior axis 206 is approximately normal to the other two axes. Position along each of these axes can be depicted by arrows, which can represent the medial-lateral 208, anterior-posterior 210, and proximal-distal 212 positioning of inserted prosthesis components. Rotation about each of these axes can also be depicted by arrows. Rotation about the proximal-distal axis 204 can correspond anatomically to external rotation of a femoral component, while rotation about the anterior-posterior axis 206 and medial-lateral axis 202 can correspond to varus-valgus angle and extension plane slope of a component, respectively.

As discussed above, kinematic alignment techniques matched the proximal tibial cut 130 (FIG. 1) to the joint line

122 (FIG. 1) and mechanical alignment techniques matched the proximal tibial cut 130 to perpendicular to the tibial axis 118 (FIG. 1). The position and angle of the proximal tibial cut 130 (FIG. 1) can affect one or more of a varus-valgus angle 214, extension plane angle 216, external rotation 218, or joint extension gap. Similarly, prior techniques matched the distal femoral cut 128 (FIG. 1) to be perpendicular to the mechanical axis 110 (FIG. 1) or perpendicular to the anatomic axis 108. The position and angle of the distal femoral cut 128 (FIG. 1) can affect one or more of the extension gap, the varus-valgus angle 214, or the extension plane angle 216. However, the present systems and apparatuses simplify the technique and reduce the need for consideration of such angles and/or gaps. This is because a surgeon can now use the present bearings or tibial baseplates to add an appropriate amount of varus-valgus angle 214 to adjust to the patient's native joint line or to tension the knee differently medially compared to laterally.

Figures 3A, 3B, 3C:
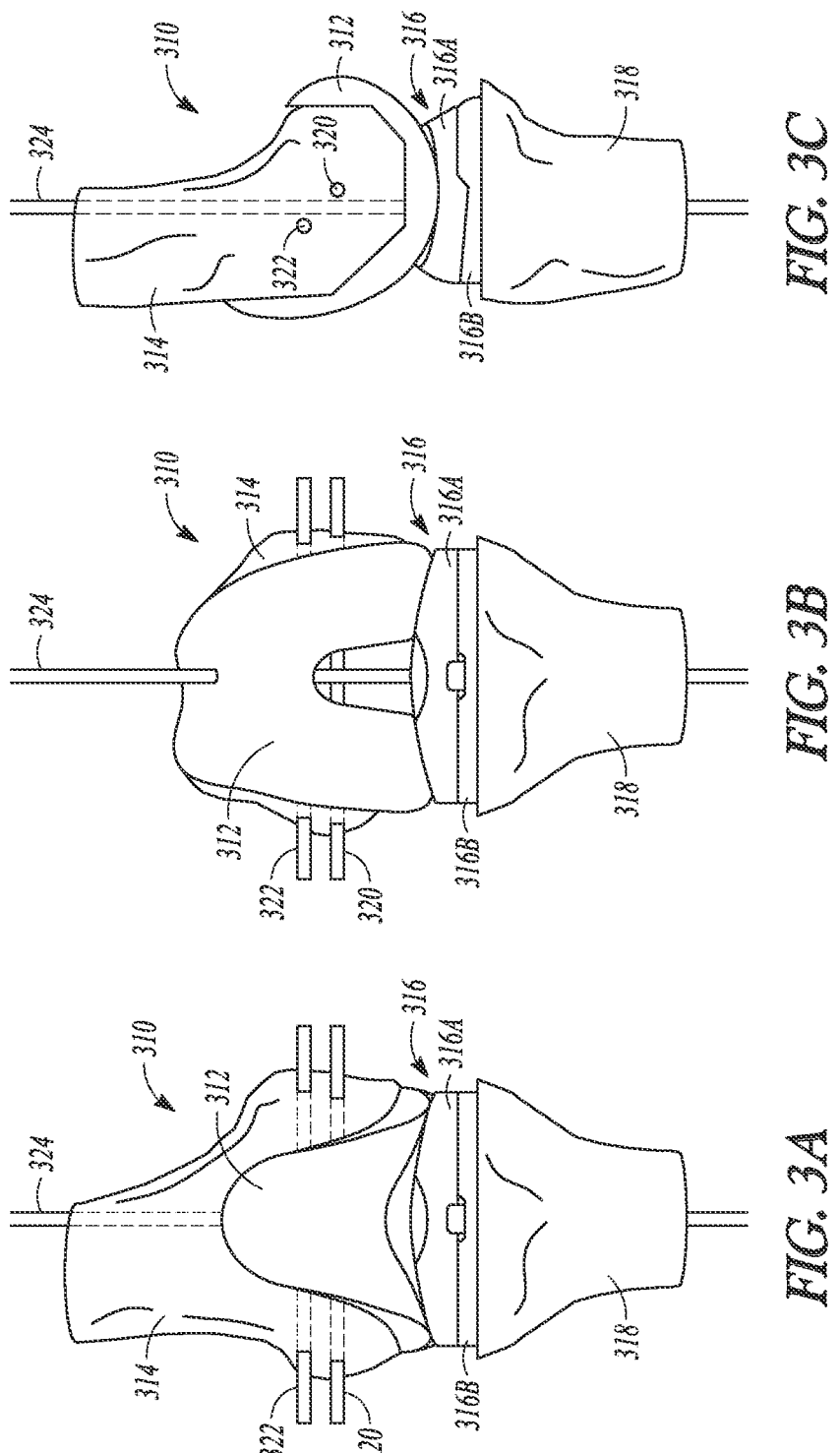
FIG. 3A is a frontal or coronal plane view of a knee joint with an implanted knee prosthesis according to an example of the present application.
FIG. 3B is a coronal view of the knee joint and knee prosthesis of FIG. 3A in 90 degrees flexion according to an example of the present application.
FIG. 3C is a side or sagittal plane view of the knee joint and knee prosthesis of FIGS. 3A and 3B in full extension according to an example of the present application.

The kinematically aligned TKA can include a determination of three kinematic axes as illustrated and described in reference to FIGS. 3A-3C. FIGS. 3A-3C show various views of a knee prosthesis 310 implanted on a knee joint and illustrate the three kinematic axes of the knee joint in a kinematically aligned TKA. The knee prosthesis 310 includes a femoral component 312 implanted on a femur 314 and a tibial component 316 implanted on a tibia 318. The tibial component 316 can include both a bearing component 316a (in FIG. 3A) and a tibial baseplate 316b (in FIG. 3A). A first kinematic axis 320 can be a transverse axis in the femur 314 about which the tibia 318 flexes and extends. The first kinematic axis 320 can be determined by projecting the lateral and medial femoral condyles of the femur 314 onto one another and fitting circles of equal radii over each other. The first kinematic axis 320 passes through a center of the circles. A second kinematic axis 322 can be a second transverse axis, parallel to the first kinematic axis 320, about which a patella of the knee joint flexes and extends. The second kinematic axis 322 can be located anterior and proximal to the first kinematic axis 320. A third kinematic axis 324 is an axis perpendicular to the first 320 and second 322 axes about which the tibia 318 internally and externally rotates on the femur 314.

The femoral component, such as 312 (in FIG. 3A), of the present application can be any suitable femoral component known or contemplated in the art. The femoral component can comprise an anterior surface with patella track and two femoral condyles, for example. By way of example, the construction of the femoral component is variously described in U.S. Pat. Nos. 8,858,643, 9,072,607, 8,690,954, 8,764,838, 8,932,365 and United States Application Publication No. 2012/0323336, the disclosures of which are incorporated by reference in their entirety.

Some exemplary surgical procedures and associated techniques and surgical instruments that may be used during method of implantation of prostheses of the present application are disclosed in "Zimmer LPS-Flex Fixed Bearing Knee, Surgical Technique," "NEXGEN COMPLETE KNEE SOLUTION, Surgical Technique for the CR-Flex Fixed Bearing Knee", "Zimmer NexGen Complete Knee Solution Extramedullary/Intramedullary Tibial Resector, Surgical Technique" (collectively the "Zimmer Surgical Techniques"), and "Vanguard® ID Total Knee Surgical Technique" the entireties of which are hereby expressly incorporated herein by reference. Additional surgical procedures are disclosed in application Ser. No. 14/809,810, entitled "INSTRUMENTS AND METHODS IN PERFORMING KINEMATICALLY-ALIGNED TOTAL KNEE ARTHRO- PLASTY" filed Jul. 27, 2015, Ser. No. 13/819,528, entitled "FEMORAL PROSTHESIS WITH MEDIALIZED PATELLAR GROOVE", filed Sep. 9, 2011, and Ser. No. 12/695, 804, entitled "APPARATUS AND METHOD FOR THE EXTRAMEDULLARY LOCATION OF THE MECHANICAL AXIS OF A FEMUR", filed Jan. 28, 2011 and the entire disclosures of which are incorporated herein by reference and are co-owned by the Applicant.

In application Ser. No. 13/819,528, a methodology is discussed whereby the mechanical axis and the anatomic axis are identified by the surgeon. Knowledge of these axes can be used in planning resections, implant orientation, etc. It is recognized that the mechanical axis extends from the center of femoral head to the center of the knee joint and is the weight bearing axis of femur. The anatomical axis extends along the longitudinal axis of shaft of femur. A surgeon may find anatomical axis by, e.g., obtaining preoperative images (such as CT scans, magnetic resonance imagining, X-rays or the like) and estimating the longitudinal axis of the shaft of femur based on sight and appearance. During a surgical procedure, a surgeon may find anatomical axis by inserting an intramedullary rod into the intramedullary canal of femur. Once the rod is so inserted, the axis of the rod is substantially coincident with the axis of femur. To find mechanical axis, a surgeon may again use preoperative images to estimate the location of axis by sight. Alternatively, the surgeon may use a rod-based system in conjunction with manipulation of the leg to find axis. Additionally, surgeons can template the proximal tibial angle using digital x-rays or other imaging technology to determine the axes and other anatomy of the knee joint as previously described with regard to FIGS. 1 and 2. Furthermore, surgeons can measure the angle of one or both of the tibia and femur removed upon resection such as with a calipers or another instrument and use this angle to derive the axes and other anatomy of the knee joint as previously described with regard to FIGS. 1 and 2.

According to some examples, the present application provides the basis for a prosthetic trial system having interchangeable components. The prosthetic trial system can include a plurality of trial tibial baseplates, each of which are able to seat on one or more portions of the tibia. These plurality of baseplates can be differently configured (e.g., provided with different thicknesses, sizes, and/or inclinations relative to one another). In some examples, some or all of the trial tibial baseplates can be configured with no inclination. This can be because the thickness of a medial portion of each tibial baseplate can be substantially the same the thickness of a lateral portion. In other examples, some or all of the trial tibia) baseplates can be configured with different inclinations (e.g., between 0.5° and 9°, inclusive) that can result from the medial portion having a different thickness than the thickness of the lateral portion. These inclinations can allow the system to achieve a plurality of different joint inclinations when coupled to a standard bearing component having no inclination or alternatively could allow a surgeon to add or lessen an amount of tension in the medial and/or lateral compartments of a knee joint fitted with a prosthesis.

The prosthetic trial system can additionally or alternatively also include a plurality of trial bearing components, which can be placed between a femoral component and one of the trial tibial baseplates Each of the plurality of trial bearing components can provide for relatively different joint inclinations (e.g., with an acute angle between 0.5° and 9°, inclusive) for the system. The different joint inclinations can be achieved by varying the thicknesses of the medial and lateral portions of the trial tibial baseplate relative to one another and by having an inclination for the articular surfaces of both the lateral and medial portions. Accordingly, a surgeon can optimally select the configuration of the tibial component and/or the bearing component so as to obtain the desired joint inclination. Such desired joint inclination can be one that best matches the natural joint line (e.g., joint line 122 of FIG. 1), for example or alternatively could allow a surgeon to add or lessen an amount of tension in the medial and/or lateral compartments of a knee joint fitted with a prosthesis.

In view of the above systems, the trialing process can include recreation by the surgeon of the natural joint line of the patient by selecting independent bearing components (e.g., a separate medial component and a separate lateral component) that contain both appropriate thicknesses and inclinations. In other examples, the trialing process can include tensioning of the joint a desired amount and selecting the independent bearing components that contain both appropriate thicknesses and inclinations to match the tensioning of the joint. In yet other examples, the trialing process can include selecting the independent bearing components that contain both appropriate thicknesses and inclinations to achieve a desired tension medially v. laterally. In yet further examples, a monolithic trial bearing component and/or a trial tibial baseplate having a desired inclination can be utilized in alternative to the independent bearing component discussed above.

Figure 4:
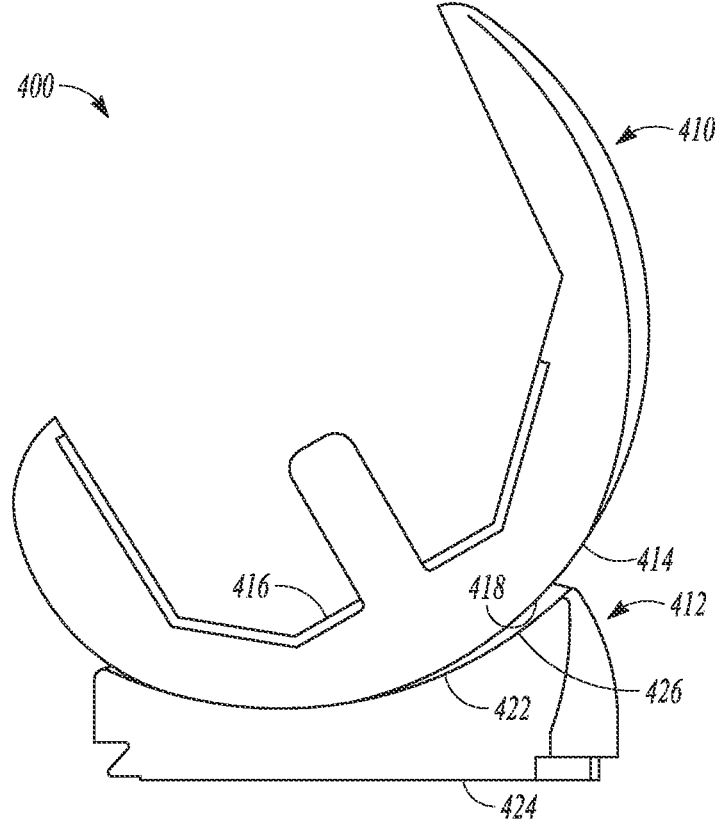
FIG. 4 shows a femoral component assembled with a bearing component in accordance with an example of the present application.

FIG. 4 shows an assembly 400 of a femoral component 410 with a bearing component 412 for a TKA according to one example. As shown in FIG. 4, a femoral component 410 can include articular surfaces 414 and proximal surfaces 416. As shown in FIG. 4, the articular surfaces 414 can include a medial condyle 418 and a lateral condyle (not shown in FIG. 4). The bearing component 412 can include articular surfaces 422 and a distal surface 424. The articular surfaces 422 can include a medial compartment 426 (also referred to as a medial portion or medial part herein) and a lateral compartment 428 (shown in FIG. 4A, also referred to as a lateral portion or lateral part herein).

The bearing component 412 can be constructed for use as a meniscal bearing component of a TKA, and therefore, can be constructed of suitable biocompatible materials such as high density polyethylene or the like.

As shown in the example of FIG. 4, the bearing component 412 can be compatible with and configured for operable use with the femoral component 410. In particular, the articular surfaces 422 of the bearing component 412 can be configured to receive the articular surfaces 414 of the femoral component 410 thereon and can be configured with some conformity to allow for movement of the femoral component 410 relative thereto in a manner that simulates the kinematics of a natural knee (e.g., allow for rollback of the femoral component 410 in flexion including anterior-posterior translation).

Figure 4A:
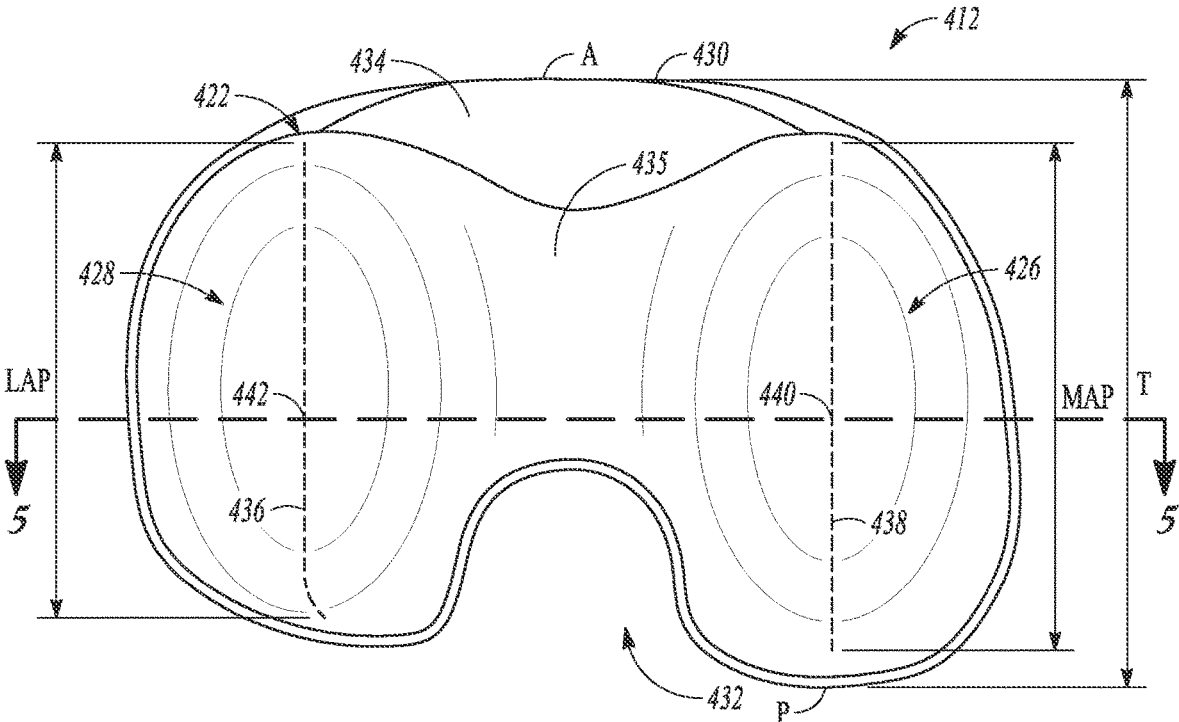
FIG. 4A shows a plan view of a proximal surface of the bearing component of FIG. 4 in accordance with an example of the present application.

The proximal surfaces 416 of the femoral component 410 can be configured to receive and couple to resected distal surfaces of the femur. The articular surfaces 414 can have conformity with the articular surfaces 422 to allow for the articulation as described above. As shown in FIG. 4A, the medial compartment 426 and the lateral compartment 428 (shown in FIG. 4A) can be configured for articulation with the medial condyle 418 and the lateral condyle (not shown in FIG. 4) of the femoral component 410, respectively. The articular surfaces 422 can be arranged opposing the distal surface 424. The distal surface 424 can be shaped to interface with a proximal surface of a tibial baseplate (subsequently shown in the examples of FIGS. 5-7) that can be affixed or otherwise mounted to a resected proximal surface of the tibia (not shown).

FIG. 4A shows a plan view of a proximal portion of the bearing component 412. FIG. 4A shows an example where the bearing component 412 is monolithic (single piece) in construction having both the medial compartment 426 and the lateral compartment 428. However, as previously described and subsequently illustrated, bearing components of multi-piece construction (two-pieces comprising a medial portion and a lateral portion, three-piece, etc.) are also contemplated. As shown in FIG. 4A, the bearing component 412 can include the articular surfaces 422, a periphery 430, a posterior cutout 432 and an anterior relief space 434. The articular surfaces 422 can include the medial compartment 426, the lateral compartment 428 and an intercondylar eminence 435.

As previously described, the articular surfaces 422 can be contacted by the condyles (not shown) of a femoral component when operably assembled in the knee. The condyles of the femoral component can contact the medial and lateral compartments 426, 428. More particularly, the medial compartment 426 and the lateral compartment 428 can be configured (e.g. are concave so as to be dish shaped) for articulation with the medial condyle and the lateral condyle of the femoral component, respectively (as shown in FIG. 4). The articular surfaces 422 (sometimes referred to as simply a proximal surface or proximal surfaces herein) can be generally opposed by a distal surface of the bearing component 412. The periphery 430 can comprise sidewalls connecting with the distal surface and the articular surface 422. The medial compartment 426 can differ in configuration from the lateral compartment 428 as will be explained in further detail subsequently. For example, the medial compartment 426 can have a different thickness, in-plan size and shape relative to the lateral compartment 428. In some examples, the anterior-posterior curvature of the lateral compartment 428 can differ from that of the medial compartment 426. However, as is shown in subsequent FIG-URES an inclination of the medial compartment 426 along at least a portion of its articular track can be substantially the same as an inclination of the lateral compartment 428 along at least a portion of its articular track.

As shown in the example of FIG. 4A, the lateral compartment 428 can have a lateral articular track 436 having a lateral anterior-posterior extent $L_{AP}$. The lateral articular track 436 can comprise a plurality of distal-most points along the articular surface 422 of the lateral compartment 428 that are contacted by the lateral femoral condyle during rollback of the femoral component. Similarly, the medial compartment 426 can have a medial articular track 438 having a medial anterior-posterior extent $M_{AP}$ that differs from the lateral anterior-posterior extent $L_{AP}$. The medial articular track 438 can comprise a plurality of distal-most points along the articular surface 422 of the medial compartment 426 that are contacted by the medial femoral condyle during rollback of the femoral component.

For convenience, the present discussion refers to points, tracks or lines of contact between the bearing component 412 and the femoral component along the articular tracks 436, 438. However, it is of course appreciated that each potential point or line of contact (i.e., any of the points along one of the articular tracks 436, 438) is not truly a point or line, but rather an area of contact. These areas of contact may be relatively larger or smaller depending on various factors, such as prosthesis materials, the amount of pressure applied at the interface between the bearing component 412 and the femoral component, relative shapes of the bearing component 412 relative to the femoral component, and the like. Moreover, it is appreciated that some of the factors affecting the size of the contact area may change dynamically during prosthesis use, such as the amount of applied pressure at the femoral/tibial interface during walking, climbing stairs or crouching, for example. For purposes of the present discussion, a contact point may be taken as the point at the geometric center of the area of contact. The geometric center, in turn, refers to the intersection of all straight lines that divide a given area into two parts of equal moment about each respective line. Stated another way, a geometric center may be said to be the average (i.e., arithmetic mean) of all points of the given area. Similarly, a line or track is the central line of contact passing through and bisecting an elongate area of contact.

Both the medial compartment 426 and the lateral compartment 428 can include dwell points 440 and 442. The dwell points 440 and 442 can comprise distal-most points along the medial articular track 438 and the lateral articular track 436, respectively. The dwell points can comprise the points on the articular surface 422 where the inclination(s) of the bearing component 412 are measured according to some examples. Although the dwell points 440 and 442 are shown as being disposed a relatively similar anterior-posterior location in the example of FIG. 4A, in other examples the anterior-posterior location (as indicated by distance T measured from anterior point A to posterior point P) of the dwell point 440 can differ from that of the dwell point 442.

According to some examples, the articular tracks 436, 438 can comprise the points on the articular surface 422 where the inclination(s) of the bearing component 412 are measured. In further examples, the dwell points 440 and 442 can comprise the points on the articular surface 422 where the inclination(s) of the bearing component 412 are measured. Alternatively, in yet further examples, the inclination(s) can be measured relative to a long axis of the tibia (approximated by the center of the tibia plateau) as will explained in further detail subsequently.

As shown in FIG. 4A, the posterior cutout 432 is sized and positioned to accommodate a posterior cruciate ligament upon implantation of the bearing component 412. The intercondylar eminence 435 can comprise an intercondylar ridge of the articular surface 422 that can be disposed between the medial and lateral compartments 426, 428. The intercondylar eminence 435 can extend generally anterior-posterior from the posterior cutout 432 to the anterior relief space 434. Thus, the intercondylar ridge defined by the intercondylar eminence 435 can be disposed between the medial and lateral dished medial and lateral compartments 426, 428 and occupies the available anterior-posterior space therebetween.

Figure 5:
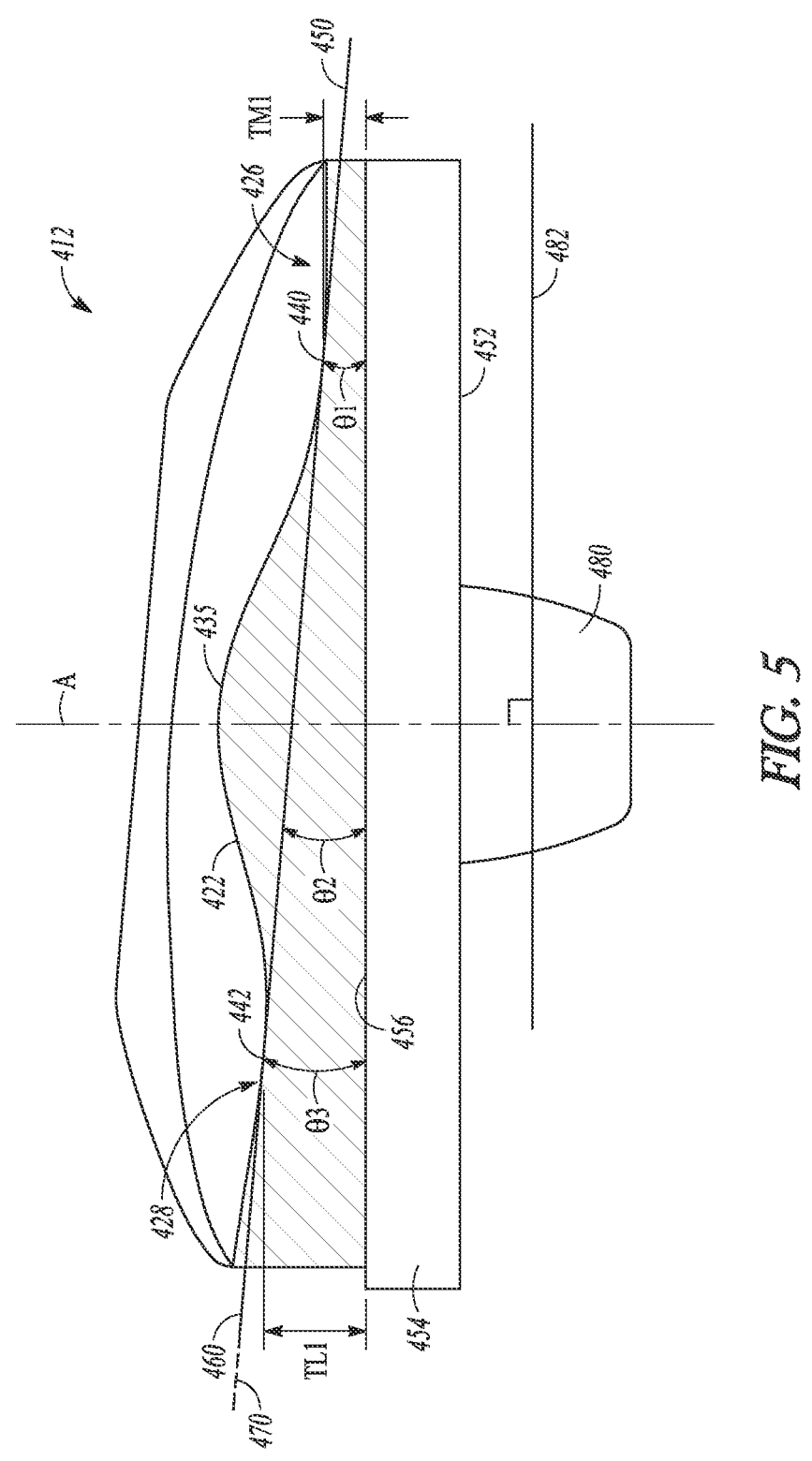
FIG. 5 shows a cross-sectional view of the bearing component of FIGS. 4 and 4A taken along a coronal plane and showing an inclination of the articular surfaces of the bearing component in accordance with an example of the present application.

FIG. 5 is a highly schematic cross-section of the bearing component 412 along line 5-5 of FIG. 4A, the line 5-5 corresponding to a coronal plane of the bearing component 412. As previously discussed with respect to FIG. 4A, the bearing component 412 of FIG. 5 has a monolithic construction and includes the medial compartment 426, the lateral compartment 428 and the intercondylar eminence 435.

As shown in FIG. 5, the medial compartment 426 can have a first inclination 450 (as indicated by a tangent line) as measured at the dwell point 440 of the medial compartment 426 relative to the resected tibial surface (approximated by a distal surface 452 of a tibial baseplate 454). Similarly, the lateral compartment 428 can have a second inclination 460 (as indicated by a tangent line) as measured at the dwell point 442 of the lateral compartment 428 relative to the resected tibial surface (approximated by the distal surface 452 of the tibial baseplate 454). The medial compartment 426 can have a thickness TM1 at the point where the first inclination 450 is measured. The thickness TM1 can differ from a corresponding thickness TL1 of the lateral compartment 428. The thickness TL1 of the lateral compartment 428 can be determined at the point where the second inclination 460 is measured. The first inclination 450 can form an acute angle θ1 with one or more of the resected tibial surface, the distal surface 452 and a proximal surface 456 of the tibial baseplate 454. The acute angle θ1 can be between 1° and 9°, inclusive according to one example. Similarly, the second inclination 460 can form an acute angle θ2 with one or more of the resected tibial surface, the distal surface 452 and a proximal surface 456 of the tibial baseplate 454. The acute angle θ2 can be between 1° and 9°, inclusive according to one example. An overall inclination 470 can form an acute angle θ3 that can be between 1° and 9°, inclusive according to one example.

As shown in the example of FIG. 5, the first inclination 450 can be substantially the same as the second inclination 460 to provide the overall inclination 470 (indicated by dashed line) of the articular surfaces 422 of the bearing component 412 relative to one or more of the proximal surface 456, the distal surface 452, and the resected tibial surface. Although the example of FIG. 5 describes the inclinations as being measured at the dwell points, the inclinations can be measured at any point on the articular track and/or relative to other features (e.g., the long axis of the tibia) according to further examples. As discussed above the inclination of the articular surface 422 at the medial compartment 426 and/or the lateral compartment 428 can also be determined by a tangent line that passes through the articular track for that compartment such as at the dwell point. The angle of the tangent line relative to the resected tibial surface in the coronal plane can approximate the inclination. According to a further example, inclination of the articular surface 422 at the medial compartment 426 and/or the lateral compartment 428 can also be determined relative to the long axis of the tibia. The long axis of the tibia can be approximated by a longitudinal axis A of a distal feature 480 such as a keel of the tibial baseplate 454. The distal feature 480 is configured to seat in the diaphysis and/or metaphysis, which corresponds to the long axis of the tibia. Thus, the longitudinal axis A of the distal feature 480 can approximate the long axis. The inclination(s) can be measured from a line 482 that intersects the longitudinal axis A in a transverse manner.

Additionally, the inclination(s) may be present for only a portion of the anterior-posterior extent of the medial and/or lateral articular tracks (refer to discussion above with regard to FIG. 4A) according to some examples. According to further examples, the inclinations can be present for the entire anterior-posterior extent of the medial and/or lateral articular tracks.

As discussed above, the present apparatuses, systems and techniques can 1) allow a surgeon to easily add joint inclination if the proximal cut surface of the tibia is cut perpendicular to the long axis of the tibia or alternatively 2) also allow for no point loading of the femur on the bearing because of the inclination (versus potential for point loading by providing for overall joint inclination with thicker medial or lateral sides that lack varus-valgus inclination for either portion).

Figure 6:
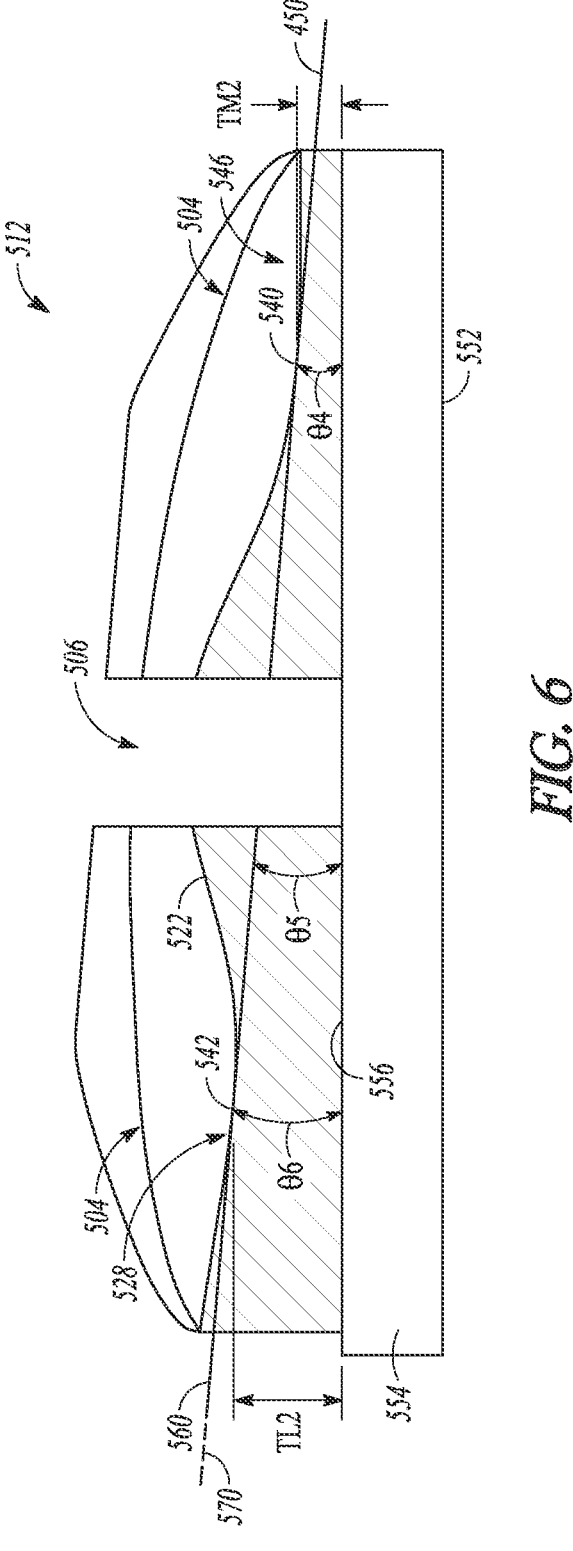
FIG. 6 shows another example of a bearing component in a cross-section taken along a coronal plane showing the inclination of the articular surfaces of the bearing component in accordance with an example of the present application.

FIG. 6 shows another example of a bearing component 512 that comprises first and second bearing elements 502 and 504 that are separate from on another by a gap 506. The first bearing element 502 can be configured to comprise a medial compartment 526 having a similar or identical construction to that of the medial compartment 426 previously described. Similarly, the second bearing element 504 can be configured to comprise a lateral compartment 528 having a similar or identical construction to that of the lateral compartment 428 previously described.

As shown in FIG. 6, the medial compartment 526 can have a first inclination 550 as measured at the dwell point 540 of the medial compartment 526 relative to the resected tibial surface (approximated by a distal surface 552 of a tibial baseplate 554). Similarly, the lateral compartment 528 can have a second inclination 560 as measured at the dwell point 542 of the lateral compartment 528 relative to the resected tibial surface (approximated by the distal surface 552 of the tibial baseplate 554). The medial compartment 526 can have a thickness TM2 at the point where the first inclination 550 is measured. The thickness TM2 can differ from a corresponding thickness TL2 of the lateral compartment 528. The thickness TL2 of the lateral compartment 528 can be determined at the point where the second inclination 560 is measured.

The first inclination 550 can form an acute angle θ4 with one or more of the resected tibial surface, the distal surface 552 and a proximal surface 556 of the tibial baseplate 554. The acute angle θ4 can be between 1° and 9°, inclusive, according to one example. Similarly, the second inclination 560 can form an acute angle θ5 with one or more of the resected tibial surface, the distal surface 552 and the proximal surface 556 of the tibial baseplate 554. The acute angle θ5 can be between 1° and 9°, inclusive, according to one example.

As shown in the example of FIG. 6, the first inclination 550 can be substantially the same as the second inclination 560 to provide an overall inclination 570 (indicated by dashed line) of the articular surfaces 522 of the bearing component 412 relative to one or more of the resected tibial surface, the distal surface 552 and the proximal surface 556. The overall inclination 570 can form an acute angle θ6 that can be between 1° and 9°, inclusive, according to one example. Although the example of FIG. 6 describes the inclinations as being measured at the dwell points, the inclinations can be measured at any point on the articular track, in other manners and/or relative to other features (e.g., the long axis of the tibia) in the manner previously discussed with reference to FIG. 5.

Figure 7:
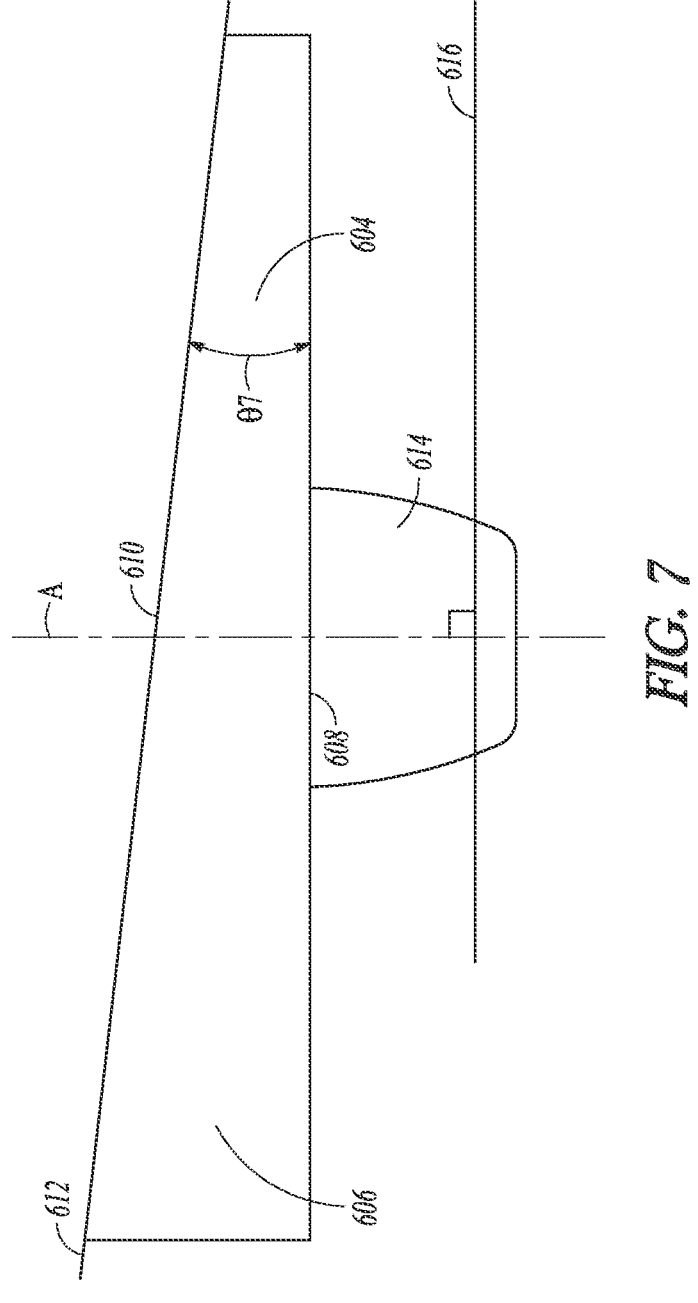
FIG. 7 shows a tibial baseplate shown in cross-section in a coronal plane, the proximal surface has an inclination relative to a distal surface of the tibial baseplate in accordance with an example of the present application.

FIG. 7 shows an alternative for providing an inclination for an implant assembly. In FIG. 7, a tibial baseplate 602 is shown. The tibial baseplate 602 has a medial portion 604, a lateral portion 606, a distal surface 608 and a proximal surface 610.

The distal surface 608 can be configured to interface with and mount on a resected surface of the tibia (not shown). The proximal surface 610 can be spaced from the distal surface 608 and can be configured to couple with a bearing component (not shown). The bearing component can be of conventional design and need not be inclined in the manner of bearing components of FIGS. 4-6.

The tibial baseplate 602 can be wedge shaped such that the proximal surface 610 is oriented at a desired inclination 612 (indicated by line) relative to the resected surface of the tibia (not shown but corresponding to the distal surface 608). The inclination 612 can form an acute angle θ7 with the distal surface 608. More particularly, the medial portion 604 can have a thickness along its medial-lateral extent that differs from a thickness of the lateral portion 606 along its medial-lateral extent.

The tibial baseplate 602 can include a distal feature 614 such as a keel similar to the one previously described in reference to FIG. 5. The distal feature 614 can couple to the distal surface 608 and can extend therefrom. According to one example, the inclination 612 can also be determined relative to the long axis of the tibia that can be approximated by a longitudinal axis A of the distal feature 614. The distal feature 614 is configured to seat in the diaphysis and/or intramedullary canal, which corresponds to the long axis of the tibia. Thus, the longitudinal axis A of the distal feature 614 can approximate the long axis. The inclination 612 can be measured from a line 616 that intersects the longitudinal axis A in a transverse manner. It can also be contemplated that the tibial component 602 could be similarly separated into medial and lateral components such as with a bicompartmental procedure whereby a gap separates the two. This gap, for example, can be comprised of bony anatomy, high density polyethylene, or other contemplated materials or patient anatomy.

The embodiments of the bearing components and tibial trays shown and described herein illustrate components for either left or a tight knee prosthesis. Right and left knee prosthesis configuration are mirror images of one another about a sagittal plane. Thus, it will be appreciated that the aspects of the prosthesis described herein are equally applicable to a left or a right knee configuration.

As used herein, "proximal" refers to a direction generally toward the head of a patient, and "distal" refers to the opposite direction of proximal, i.e., away from the head of a patient. As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior." Similarly, the terms "medial" and "lateral" should be given their generally understood anatomical interpretation. "Medial" refers to the inner part of the knee prosthesis (when in the implanted orientation) and "lateral" refers to the outer part "Medial" refers to the opposite direction of "lateral." "Varus" is defined as relating to, or being synonymous with "medial" or being relatively more medially disposed than a midline or other feature or component. "Valgus" is defined as relating to, or being synonymous with "lateral" or being relatively more laterally disposed than a midline or other feature or component.

"Congruence" "conformity" or "correspond" or similar terminology or tenses thereof in the context of knee prostheses refers to the similarity of curvature between the femoral articular surface of the femoral implant (e.g., the femoral condyles) and the correspondingly shaped tibial articular surface of a tibial implant. In some cases, the femoral articular surface can be convex while the tibial articular surface can be concave. A convex surface may be considered to be highly conforming to a corresponding concave surface where the two surfaces have similar or identical convex and concave geometries, such that the convex surface "nests" or inter-fits with the concave surface in a manner that allows for articulation of at least one component relative to another.

The above Detailed Description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more."

In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:
1. A system for a knee arthroplasty comprising:
a trial tibial baseplate configured to couple to one or more resected proximal surfaces of a tibia of a patient; and
a plurality of trial bearing components each configured to couple with the trial tibial baseplate, wherein at least some of the trial bearing components each comprise:
a medial compartment having a medial articular surface with a medial articular track and having a first thickness as measured at the medial articular track between the medial articular surface and a medial distal surface, and
a lateral compartment having a lateral articular surface with a lateral articular track and having a second thickness as measured at the lateral articular track between the lateral articular surface and a lateral distal surface, wherein the medial articular surface at the medial articular track and the lateral articular surface at the lateral articular track each have an inclination so as to form an acute angle with respect to the one or more resected proximal surfaces of the tibia, wherein the at least some of the plurality of bearing components are differently configured relative to one another to provide for a different degree for the acute angle.

2. The system of claim 1, wherein the at least some of the plurality of bearing components each are a monolithic single piece construct forming both the medial compartment and the lateral compartment.

3. The system of claim 1, wherein the at least some of the plurality of bearing components each comprise a two-piece bearing having the medial compartment separated from the lateral compartment.

4. The system of claim 1, wherein the inclination of the at least some of the plurality of bearing components occurs at dwell points of the medial and lateral articular tracks.

5. The system of claim 1, wherein the inclination of the at least some of the plurality of bearing components occurs for only a portion of an anterior-posterior extent of at least one of the medial articular track and the lateral articular track.

6. The system of claim 1, wherein the inclination of the at least some of the plurality of bearing components occurs for substantially an entirety of an anterior-posterior extent of at least one of the medial articular track and the lateral articular track.

7. The system of claim 1, wherein the inclination of the at least some of the plurality of bearing components is in one of a varus-valgus or proximal-distal direction only.

8. The system of claim 1, wherein the inclination of the at least some of the plurality of bearing components is in a varus-valgus and a proximal-distal direction.

9. A system for a knee arthroplasty comprising:

a plurality of trial tibial baseplates, each of the plurality of trial tibial baseplates are configured to couple to one or more resected proximal surfaces of a tibia, wherein at least some of the plurality of trial tibial baseplates have a proximal surface with an inclination in a varus-valgus direction relative to a distal surface thereof so as to form an acute angle therebetween, and wherein the at least some of the plurality of trial tibial baseplates are differently configured relative to one another to provide for a different degree for the acute angle; and a plurality of trial bearing components each configured to couple with one or more of the plurality of trial tibial baseplates, wherein at least some of the trial bearing components each comprise:

a medial compartment having a medial articular surface with a medial articular track and having a first thickness as measured at the medial articular track between the medial articular surface and a medial distal surface, and a lateral compartment having a lateral articular surface with a lateral articular track and having a second thickness as measured at the lateral articular track between the lateral articular surface and a lateral distal surface, wherein the medial articular surface at the medial articular track and the lateral articular surface at the lateral articular track each have an inclination so as to form an acute angle with respect to the one or more resected proximal surface of the tibia, wherein the at least some of the plurality of bearing components are differently configured relative to one another to provide for a different degree for the acute angle.

10. The system of claim 9, wherein the inclination of the at least some of the plurality of bearing components is in one of a varus-valgus or proximal-distal direction only.

11. The system of claim 9, wherein the inclination of the at least some of the plurality of bearing components is in a varus-valgus and a proximal-distal direction.

12. The system of claim 9, wherein the at least some of the plurality of bearing components each are a monolithic single piece construct forming both the medial compartment and the lateral compartment.

13. The system of claim 12, wherein the at least some of the plurality of bearing components each comprise a two-piece bearing having the medial compartment separated from the lateral compartment.

14. The system of claim 9, wherein the inclination of the at least some of the plurality of bearing components occurs at dwell points of the medial and lateral articular tracks.

15. The system of claim 9, wherein the inclination of the at least some of the plurality of bearing components occurs for only a portion of an anterior-posterior extent of at least one of the medial articular track and the lateral articular track.

16. The system of claim 9, wherein the inclination of the at least some of the plurality of bearing components occurs for substantially an entirety of an anterior-posterior extent of at least one of the medial articular track and the lateral articular track.

17. The system of claim 9, wherein the knee arthroplasty comprises one of a partial knee arthroplasty, a bi-compartmental knee arthroplasty or a total knee arthroplasty.

18. The system of claim 9, wherein for at least one of the plurality of the trial tibial baseplates, the at least one of the plurality of the trial tibial baseplate includes:

a medial portion;

a lateral portion opposing the medial portion, wherein a thickness of the lateral portion as measured between the proximal surface and the distal surface along a medial-lateral extent of the lateral portion that differs from a thickness of the medial portion as measured between the proximal surface and the distal surface along a medial-lateral extent of the medial portion.

* * * * *